United States Patent
Rennie et al.

(10) Patent No.: US 10,472,363 B2
(45) Date of Patent: Nov. 12, 2019

(54) SGC STIMULATORS

(71) Applicant: Cyclerion Therapeutics, Inc., Cambridge, MA (US)

(72) Inventors: Glen Robert Rennie, Somerville, MA (US); Rajesh R. Iyengar, West Newton, MA (US); Thomas Wai-Ho Lee, Lexington, MA (US); Paul Allan Renhowe, Sudbury, MA (US); Joon Jung, Newton, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/693,758

(22) Filed: Sep. 1, 2017

(65) Prior Publication Data

US 2018/0065971 A1    Mar. 8, 2018

Related U.S. Application Data

(60) Provisional application No. 62/482,486, filed on Apr. 6, 2017, provisional application No. 62/468,598, filed on Mar. 8, 2017, provisional application No. 62/423,445, filed on Nov. 17, 2016, provisional application No. 62/382,942, filed on Sep. 2, 2016.

(51) Int. Cl.
| | | |
|---|---|---|
| *C07D 487/04* | (2006.01) | |
| *A61K 31/437* | (2006.01) | |
| *C07D 473/00* | (2006.01) | |
| *A61K 31/52* | (2006.01) | |
| *C07D 471/04* | (2006.01) | |
| *A61K 31/4985* | (2006.01) | |

(52) U.S. Cl.
CPC .......... *C07D 487/04* (2013.01); *A61K 31/437* (2013.01); *A61K 31/4985* (2013.01); *A61K 31/52* (2013.01); *C07D 471/04* (2013.01); *C07D 473/00* (2013.01)

(58) Field of Classification Search
CPC ............................ C07D 487/04; A61K 31/437
See application file for complete search history.

(56) References Cited

U.S. PATENT DOCUMENTS

| | | | |
|---|---|---|---|
| 6,632,815 B2 | 10/2003 | Zhu et al. | |
| 6,720,317 B1 | 4/2004 | Zhu et al. | |
| 6,844,367 B1 | 1/2005 | Zhu et al. | |
| 8,748,442 B2* | 6/2014 | Kim .................. | A61K 31/4155 514/269 |
| 9,061,030 B2* | 6/2015 | Kim .................... | C07D 401/04 |
| 9,309,235 B2* | 4/2016 | Im ....................... | C07D 413/14 |
| 9,481,689 B2* | 11/2016 | Nakai .................. | C07D 413/14 |
| 9,586,937 B2* | 3/2017 | Nakai .................. | C07D 413/14 |
| 2004/0186148 A1 | 9/2004 | Shankar et al. | |

FOREIGN PATENT DOCUMENTS

| | | |
|---|---|---|
| WO | 2001064643 A2 | 9/2001 |
| WO | 2003059346 A1 | 7/2003 |
| WO | 2005020921 A2 | 3/2005 |
| WO | 2010069684 A1 | 6/2010 |
| WO | 2010088518 A2 | 8/2010 |
| WO | 2012/080729 A2 | 6/2012 |
| WO | 2015/187470 A1 | 12/2015 |
| WO | 2016044446 A2 | 3/2016 |
| WO | 2016/081668 A1 | 5/2016 |
| WO | 2016087342 A1 | 6/2016 |
| WO | 2016/191334 A1 | 12/2016 |
| WO | 2016/191335 A1 | 12/2016 |
| WO | 2017002120 A1 | 1/2017 |

OTHER PUBLICATIONS

International Search Report and Written Opinion, PCT/US2017/049834, dated Nov. 6, 2017.
Aissa et al., Targeting NO/cGMP Signaling in the CNS for Neurodegeneration and Alzheimer's Disease. Curr Med Chem. 2016;23(24):2770-2788.
Csiszar et al., Hypertension impairs neurovascular coupling and promotes microvascular injury: role in exacerbation of Alzheimer's disease. Geroscience. 2017;39:359-372.
De La Torre, Is Alzheimer's disease a neurodegenerative or a vascular disorder? Data, dogma, and dialectics. Lancet Neural. Mar. 2004;3(3):184-190.
Di Marco et al., Vascular dysfunction in the pathogenesis of Alzheimer's disease—A review of endothelium-mediated mechanisms and ensuing vicious circles. Neurobiol Dis. Oct. 2015;82:593-606.
Griebenow et al., Identification of acidic heterocycle-substituted 1H-pyrazolo[3,4-b]pyridines as soluble guanylate cyclase stimulators. Bioorg Med Chem Lett. Mar. 1, 2013;23(5):1197-1200.

(Continued)

*Primary Examiner* — Golam M Shameem
(74) *Attorney, Agent, or Firm* — McCarter & English, LLP; Steven G. Davis; Xin Zhang

(57) ABSTRACT

The present disclosure relates to stimulators of soluble guanylate cyclase (sGC), pharmaceutical formulations comprising them and their uses thereof, alone or in combination with one or more additional agents, for treating various diseases, wherein an increase in the concentration of nitric oxide (NO) or an increase in the concentration of cyclic Guanosine Monophosphate (cGMP), or both, or an upregulation of the NO pathway is desirable. The compounds are of Formula I:

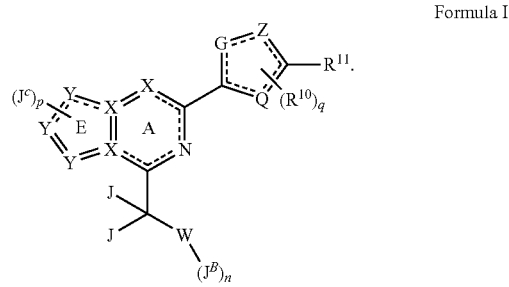

Formula I

2 Claims, 5 Drawing Sheets

(56) References Cited

OTHER PUBLICATIONS

Hutson et al., The selective phosphodiesterase 9 (PDE9) inhibitor PF-04447943 (6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one) enhances synaptic plasticity and cognitive function in rodents. Neuropharmacology. Sep. 2011;61(4):665-676.

Katusic et al., Endothelial nitric oxide: protector of a healthy mind. Eur Heart J. Apr. 2014;35(14):888-894.

Kleiman et al., Phosphodiesterase 9A regulates central cGMP and modulates responses to cholinergic and monoaminergic perturbation in vivo. J Pharmacol Exp Ther. May 2012;341(2):396-409.

Lourenço et al., Neurovascular-neuroenergetic coupling axis in the brain: master regulation by nitric oxide and consequences in aging and neurodegeneration. Free Radic Biol Med. Jul. 2017;108:668-682.

Puzzo et al., Amyloid-beta peptide inhibits activation of the nitric oxide/cGMP/cAMP-responsive element-binding protein pathway during hippocampal synaptic plasticity. J Neurosci. Jul. 20, 2005;25(29):6887-6897.

Qin, Modulating nitric oxide signaling in the CNS for Alzheimer's disease therapy. Future Med Chem. Aug. 2013;5(12):1451-1468.

Roberts et al., Acidic triazoles as soluble guanylate cyclase stimulators. Bioorg Med Chem Lett. Nov. 1, 2011;21(21):6515-6518.

Thatcher et al., Nitric Oxide Mimetic Molecules as Therapeutic Agents in Alzheimer's Disease. Current Alzheimer Research. 2005;2:1-12.

Toda et al., Cerebral blood flow regulation by nitric oxide: recent advances. Pharmacol Rev. Mar. 2009;61(1):62-97.

Verhoest et al., Design and discovery of 6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one (PF-04447943), a selective brain penetrant PDE9A inhibitor for the treatment of cognitive disorders. J Med Chem. Nov. 8, 2012;55(21):9045-9054.

* cited by examiner

SGC STIMULATORS

RELATED APPLICATIONS

This application claims the benefit of the filing date, under 35 U.S.C. § 119(e), of U.S. Provisional Application No. 62/382,942, filed on Sep. 2, 2016; U.S. Provisional Application No. 62/423,445, filed on Nov. 17, 2016; U.S. Provisional Application No. 62/468,598, filed on Mar. 8, 2017; and U.S. Provisional Application No. 62/482,486 filed on Apr. 6, 2017. The entire contents of each of the above-referenced applications are incorporated herein by reference.

FIELD OF THE INVENTION

The present disclosure relates to stimulators of soluble guanylate cyclase (sGC), pharmaceutical formulations comprising them and their uses thereof, alone or in combination with one or more additional agents, for treating various diseases, wherein an increase in the concentration of nitric oxide (NO) or an increase in the concentration of cyclic Guanosine 3',5'-Monophosphate (cGMP) or both, or an upregulation of the NO pathway is desirable.

BACKGROUND OF THE INVENTION

Soluble guanylate cyclase (sGC) is the primary receptor for nitric oxide (NO) in vivo. sGC can be activated via both NO-dependent and NO-independent mechanisms. In response to this activation, sGC converts guanosine 5'-triphosphate (GTP) into the secondary messenger cyclic GMP (cGMP). The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III) which regulates smooth muscle relaxation and blood pressure. Experimental and clinical evidence indicates that reduced concentrations, bioavailability and/or responsiveness to endogenously produced NO contributes to the development of disease.

NO-independent, heme-dependent, sGC stimulators, have several important differentiating characteristics, when compared to other types of sGC modulators, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed.

Compounds that stimulate sGC in an NO-independent manner offer considerable advantages over other current alternative therapies that either target the aberrant NO pathway or that are directed at diseases wherein upregulation of the NO pathway is beneficial. There is a need to develop novel stimulators of sGC. These compounds are useful for treating various diseases, wherein the diseases or disorders are ones that would benefit from sGC stimulation or from an increase in the concentration of nitric oxide (NO) or cyclic guanosine 3',5'-monophosphate (cGMP) or both, or wherein an upregulation of the NO pathway is desirable.

SUMMARY OF THE INVENTION

The present invention is directed to compounds of Formula I, or pharmaceutically acceptable salts thereof,

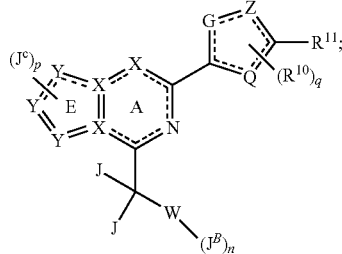

Formula I wherein:
rings E and A form the core of the molecule and are aromatic; each instance of X and Y is independently selected from N or C; wherein a maximum of 4 instances of X and Y are simultaneously N;
W is either
i) absent, with $J^B$ connected directly to the carbon atom bearing two J groups, each J is independently selected from hydrogen or methyl, n is 1 and $J^B$ is a $C_{1-7}$ alkyl chain optionally substituted by up to 9 instances of fluorine; or
ii) a ring B that is a phenyl, a $C_{3-7}$ cycloalkyl ring or a 5 or 6-membered heteroaryl ring, containing 1 or 2 ring nitrogen atoms;
   wherein when ring B is the phenyl or 5 or 6-membered heteroaryl ring; each J is independently selected from hydrogen or methyl; n is an integer selected from 0 to 3; and each $J^B$ is independently selected from halogen, —CN, a $C_{1-6}$ aliphatic, —$OR^B$ or a $C_{3-8}$ cycloaliphatic ring; and
   wherein when ring B is the $C_{3-7}$ cycloalkyl ring; each J is hydrogen; n is an integer selected from 0 to 3 and each $J^B$ is independently selected from halogen, —CN, a $C_{1-6}$ aliphatic or —$OR^{B1}$;
   wherein each $J^B$ that is a $C_{1-6}$ aliphatic and each $J^B$ that is a $C_{3-8}$ cycloaliphatic ring is optionally and independently substituted with up to 3 instances of $R^3$;
each $R^B$ is independently selected from a $C_{1-6}$ aliphatic or a $C_{3-8}$ cycloaliphatic ring; said $R^B$ optionally and independently substituted with up to 3 instances of $R^{3a}$;
each $R^{B1}$ is independently selected from hydrogen, a $C_{1-6}$ aliphatic or a $C_{3-8}$ cycloaliphatic ring; wherein each of said $C_{1-6}$ aliphatic and each of said $C_{3-8}$ cycloaliphatic ring is optionally and independently substituted with up to 3 instances of $R^{3b}$;
each $R^3$, $R^{3a}$ and $R^{3b}$ is, in each instance, independently selected from halogen, —CN, $C_{1-4}$ alkyl, $C_{1-4}$ haloalkyl, —$O(C_{1-4}$ alkyl) or —$O(C_{1-4}$ haloalkyl);
p is an integer selected from 1, 2 or 3;
each $J^C$ is independently selected from hydrogen, halogen, $C_{1-4}$ aliphatic, $C_{1-4}$ alkoxy or —CN; wherein each said $C_{1-4}$ aliphatic and $C_{1-4}$ alkoxy is optionally and independently substituted by up to 3 instances of $C_{1-4}$ alkoxy, $C_{1-4}$ haloalkoxy, —OH or halogen;
Q, G and Z are each independently N, S or O, wherein at least two of Q, G and Z are N;
q is 0, 1 or 2;

$R^{10}$ is $C_{1-6}$ alkyl optionally and independently substituted with 0-3 occurrences of $R^{15}$, phenyl optionally and independently substituted with 0-3 occurrences of $R^{15}$, 5- or 6-membered heteroaryl optionally and independently substituted with 0-3 occurrences of $R^{15}$, $C_{3-8}$ cycloalkyl optionally and independently substituted with 0-3 occurrences of $R^{15}$ or 3-8 membered heterocyclyl optionally and independently substituted with 0-3 occurrences of $R^{15}$; wherein each of said 5- to 6-membered heteroaryl ring and each of said 3-8 membered heterocyclyl contains up to 3 ring heteroatoms independently selected from N, O or S;

$R^{11}$ is H, —$NR^{a2}R^{b2}$, —$C(O)NR^{a2}R^{b2}$, —$C(O)R^{15a}$, —$SO_2R^{b2}$, —$SR^{b2}$, halo, —$OCF_3$, —CN, hydroxyl, $C_{2-6}$ alkenyl optionally and independently substituted with 0-2 occurrences of $R^{b2}$, $C_{2-6}$ alkynyl optionally and independently substituted with 0-2 occurrences of $R^{b2}$; $C_{1-6}$ alkyl optionally and independently substituted with 0-3 occurrences of $R^{15}$, $C_{1-6}$ alkoxy optionally and independently substituted with 0-5 occurrences of $R^{15}$, phenyl optionally and independently substituted with 0-3 occurrences of $R^{15}$, 5- to 6-membered heteroaryl optionally and independently substituted with 0-3 occurrences of $R^{15}$, $C_{3-8}$ cycloalkyl optionally and independently substituted with 0-3 occurrences of $R^{15}$ or 3-8 membered heterocyclyl optionally and independently substituted with 0-3 occurrences of $R^{15}$; wherein each of said 5- to 6-membered heteroaryl and each of said 3-8 membered heterocyclyl contains up to 3 ring heteroatoms independently selected from N, O or S; or when $R^{10}$ is a substituent of Z, $R^{10}$ and $R^{11}$, taken together with Z and the carbon to which $R^{11}$ is attached, form a 3-10 membered heterocyclic ring optionally and independently substituted with 0-3 occurrences of $R^{15}$; wherein each of said 3-10 membered heterocyclyl contains up to 3 ring heteroatoms independently selected from N, O or S;

$R^{15}$ is halo, —$OR^{b2}$, —$SR^{b2}$, —$NR^{a2}R^{b2}$, —$C(O)R^{b2}$, —$C(O)NR^{a2}R^{b2}$, —$NR^{b2}C(O)OR^{b2}$, —$OC(O)NR^{a2}R^{b2}$, $C_{2-4}$ alkenoxy, $C_{3-8}$ cycloalkyl optionally and independently substituted with 0-3 occurrences of $R^{18}$, phenyl optionally and independently substituted with 0-3 occurrences of $R^{18}$, 5- or 6-membered heteroaryl optionally and independently substituted with 0-3 occurrences of $R^{18}$ or 3-10 membered heterocyclyl optionally and independently substituted with 0-3 occurrences of $R^{18}$; wherein each of said 5- or 6-membered heteroaryl ring and each of said 3-10 membered heterocyclyl contains up to 3 ring heteroatoms independently selected from N, O or S;

$R^{15a}$ is $C_{3-8}$ cycloalkyl optionally and independently substituted with 0-3 occurrences of $R^{18}$, phenyl optionally and independently substituted with 0-3 occurrences of $R^{18}$, 5- or 6-membered heteroaryl optionally and independently substituted with 0-3 occurrences of $R^{18}$ or 3-10 membered heterocyclyl optionally and independently substituted with 0-3 occurrences of $R^{18}$; wherein each of said 5- or 6-membered heteroaryl ring and each of said 3-10 membered heterocyclyl contains up to 3 ring heteroatoms independently selected from N, O or S;

each $R^{18}$ is independently selected from halo, hydroxyl, $C_{1-6}$ alkyl, $C_{1-6}$ alkoxy, $C_{1-6}$ haloalkyl or phenyl;

$R^{a2}$ is hydrogen, —$C(O)R^{b2}$, $C_{1-6}$ alkyl or $C_{1-6}$ haloalkyl; and $R^{b2}$ is hydrogen, $C_{1-6}$ alkyl or $C_{1-6}$ haloalkyl.

The invention is also directed to a pharmaceutical composition comprising a compound according to Formula I, or a pharmaceutically acceptable salt thereof, and at least one pharmaceutically acceptable excipient or carrier. The invention is also directed to a pharmaceutical formulation or dosage form comprising the pharmaceutical composition.

The invention also provides a method of treating or preventing a disease, health condition or disorder in a subject in need thereof, comprising administering, alone or in combination therapy, a therapeutically effective amount of a compound of Formula I or a pharmaceutically acceptable salt thereof to the subject; wherein the disease is one that benefits from sGC stimulation or from an increase in the concentration of NO or cGMP or both, or from an upregulation of the NO pathway.

DETAILED DESCRIPTION OF THE INVENTION

Figure 1:
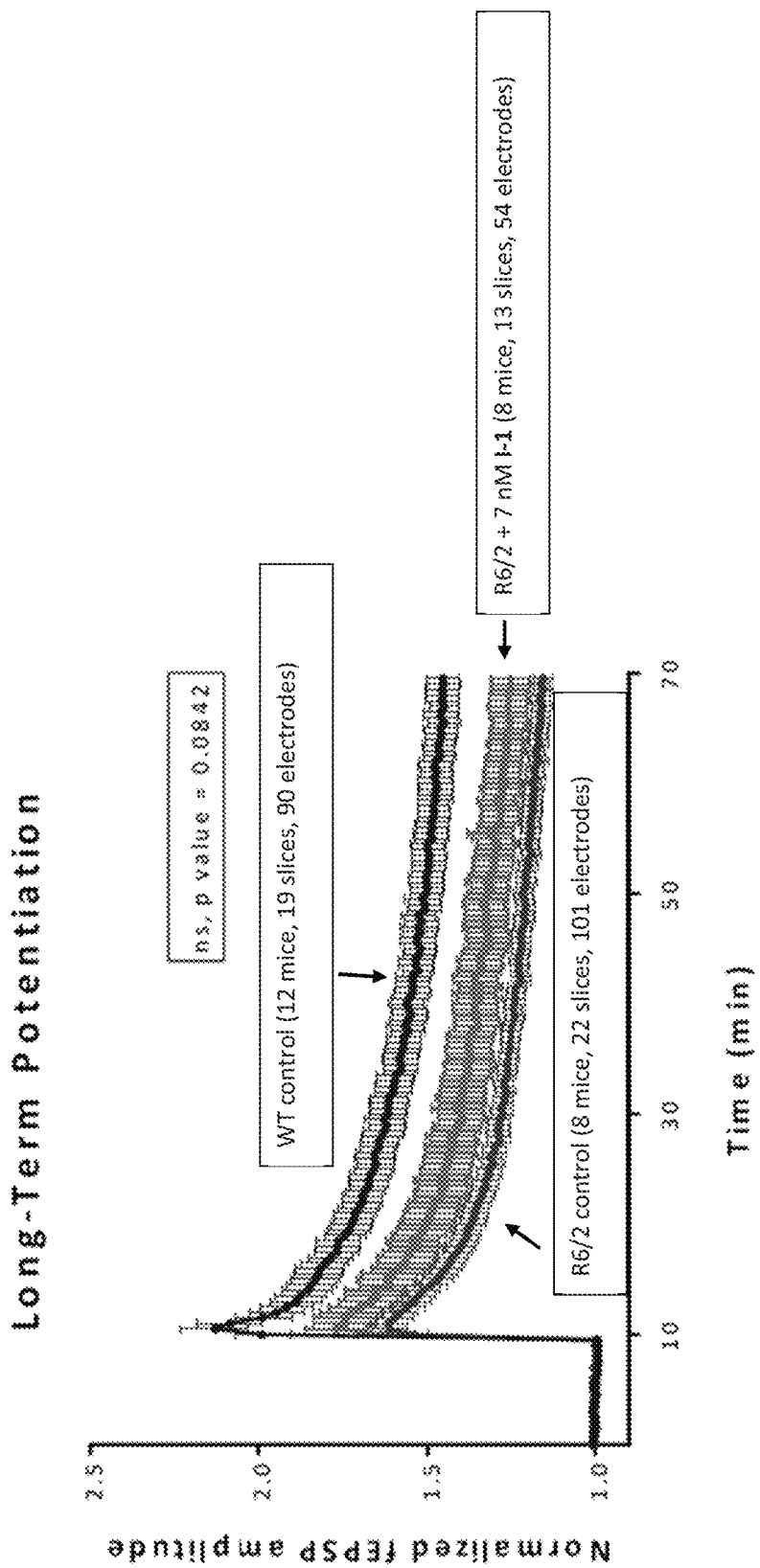
FIG. 1 is a plot of the long-term potentiation of wild type (WT) mice hippocampal slices (top curve), R6/2 mice hippocampal slices (bottom curve), and R6/2 mice hippocampal slices treated with 7 nM Compound I-1 (middle curve).

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

As described herein, compounds of Formula I may be optionally substituted with one or more substituents, such as illustrated generally below, or as exemplified by particular classes, subclasses and species of the invention. The phrase "optionally substituted" is used interchangeably with the phrase "substituted or unsubstituted." In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position unless otherwise specified. The term "optionally and independently" may be used to describe this situation. As an example, one substituent disclosed herein is $R^{10}$, which may be, among other options, $C_{1-6}$ alkyl optionally and independently substituted with 0-3 occurrences of $R^{15}$. In this instance, the $C_{1-6}$ alkyl may be "optionally substituted": it may be unsubstituted (i.e., 0 occurrences of $R^{15}$) or substituted (i.e., 1, 2, or 3 occurrences of $R^{15}$). When there are multiple occurrences of $R^{15}$ (e.g., 2), each $R^{15}$ may be the same substituent (e.g., two fluoro atoms) or different (e.g., —OH and chloro). As will be apparent to one of ordinary skill in the art, groups such as —H, halogen, —NO$_2$, —CN, —OH, —NH$_2$ or —OCF$_3$ would not be substitutable groups.

The phrase "up to", as used herein, refers to zero or any integer number that is equal or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. A group having from 0-3 atoms could have 0, 1, 2, or 3 atoms. When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound is one that is not substantially altered when kept at a temperature of 25° C. or less, in the absence of moisture or other chemically reactive conditions, for at least a week. A chemically feasible compound is a compound that can be prepared by a person skilled in the art based on the disclosures herein supplemented, if necessary, relevant knowledge of the art.

A compound, such as the compounds of Formula I or Table I or other compounds herein disclosed, may be present in its free form (e.g. an amorphous form, or a crystalline form or a polymorph). Under certain conditions, compounds may also form co-forms. As used herein, the term co-form is synonymous with the term multi-component crystalline form. The formation of a salt is determined by how large the difference is in the pKas between the partners that form the mixture. For purposes of this disclosure, compounds include pharmaceutically acceptable salts, even if the term "pharmaceutically acceptable salts" is not explicitly noted.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are also within the scope of the invention.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of the present invention (e.g., those labeled with $^3H$ and $^{14}C$) are useful in compound and/or substrate tissue distribution assays. Tritiated (i.e., $^3H$) and carbon-14 (i.e., $^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "aliphatic" or "aliphatic group" or "aliphatic chain", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 or 1-2 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like. An aliphatic group will be represented by the term "$C_{x-y}$ aliphatic"; wherein x and y are the minimum and the maximum number of carbon atoms forming the aliphatic chain.

The term "alkyl" (as in "alkyl chain" or "alkyl group"), as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl (sec-butyl), t-butyl, pentyl, hexyl, heptyl, octyl and the like. An alkyl group will be represented by the term "$C_{x-y}$ alkyl"; wherein x and y are the minimum and the maximum number of carbon atoms forming the alkyl chain.

The term "alkenyl" (as in "alkenyl chain" or "alkenyl group"), refers to a linear or branched-chain monovalent hydrocarbon radical with at least one site of unsaturation, i.e., a carbon-carbon, $sp^2$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like. An alkenyl group will be represented by the term "$C_{x-y}$ alkenyl"; wherein x and y are the minimum and the maximum number of carbon atoms forming the alkenyl chain.

The term "alkynyl" (as in "alkynyl chain" or "alkynyl group"), refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like. An alkynyl group will be represented by the term "$C_{x-y}$ alkynyl"; wherein x and y are the minimum and the maximum number of carbon atoms forming the alkynyl chain.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic". In some instances the term could be used in the phrase "aromatic carbocycle", and in this case it would refers to an "aryl group" as defined below.

The term "cycloaliphatic" (or "non-aromatic carbocycle", "non-aromatic carbocyclyl", "non-aromatic carbocyclic" or "cycloaliphatic ring") refers to a cyclic hydrocarbon that is completely saturated or that contains one or more units of unsaturation but which is not aromatic, and which has a single point of attachment to the rest of the molecule. In one embodiment, the term "cycloaliphatic" refers to a monocyclic $C_{3-12}$ hydrocarbon. A cycloaliphatic ring will be represented by the term "$C_{x-y}$ cycloaliphatic"; wherein x and y are the minimum and the maximum number of carbon atoms forming the cycloaliphatic ring. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

"Cycloalkyl" or "cycloalkyl ring", as used herein, refers to a ring system in which is completely saturated and which has a single point of attachment to the rest of the molecule. In one embodiment, the term "cycloalkyl" refers to a monocyclic $C_{3-12}$ saturated hydrocarbon. Suitable cycloalkyl groups include, but are not limited to, cyclopropyl, cyclobutyl, cyclopentyl, cyclohexyl, cycloheptyl, cycloheptenyl, norbornyl, cyclooctyl, cyclononyl, cyclodecyl, cycloundecyl, cyclododecyl, and the like. A cycloalkyl ring will be represented by the term "$C_{x-y}$ cycloalkyl"; wherein x and y are the minimum and the maximum number of carbon atoms forming the cycloalkyl ring.

"Heterocycle" (or "heterocyclyl" or "heterocyclic or "heterocyclic ring"), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term could be used in the phrase "aromatic heterocycle", and in this case it would refer to a "heteroaryl group" as defined below. In some embodiments, the heterocycle has 3-10 ring members in which one or more ring members is a heteroatom independently selected from oxygen or nitrogen. In other embodiments, a heterocycle may be a monocycle having 3-7 ring members (2-6 carbon atoms and 1-4 heteroatoms).

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl.

The term "heteroaryl" (or "heteroaromatic" or "heteroaryl group" or "aromatic heterocycle" or "heteroaryl ring") used alone or as part of a larger moiety as in "heteroarylalkyl" or "heteroarylalkoxy" refers to a ring which is aromatic and contains one or more heteroatoms, has between 5 and 6 ring members and which has a single point of attachment to the rest of the molecule. Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl.

The term "ring atom" refers to an atom such as C, N, O or S that is part of the ring of an aromatic ring, a cycloaliphatic ring, a heterocyclic or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, including any oxidized form of nitrogen, sulfur, the quaternized form of any basic nitrogen, or a substitutable nitrogen of a heterocyclic or heteroaryl ring, for example N (as in 3,4-dihydro-2H-pyrrolyl), NH (as in pyrrolidinyl) or NR$^+$ (as in N-substituted pyrrolidinyl).

In some embodiments, two independent occurrences of a variable may be taken together with the atom(s) to which each variable is bound to form a 5-8-membered aryl or heteroaryl ring or a 3-8-membered cycloaliphatic ring or heterocyclyl. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, cycloaliphatic or aryl ring, wherein the group is attached to the rest of the molecule by a single point of attachment; and b) two independent occurrences of a substituent that are bound to different atoms and are taken together with both of those atoms to form a heterocyclyl, heteroaryl, cycloaliphatic or aryl ring, wherein the ring that is formed has two points of attachment with the rest of the molecule.

It will be appreciated that a variety of other rings can be formed when two independent occurrences of a substituent are taken together with the atom(s) to which each substituent is bound and that the examples detailed above are not intended to be limiting.

As described herein, a bond drawn from a substituent to the center of one ring within a multiple-ring system (as shown below), represents substitution of the substituent at any substitutable position in any of the rings within the multiple ring system. For example, formula D3 represents possible substitution in any of the positions shown in formula D4:

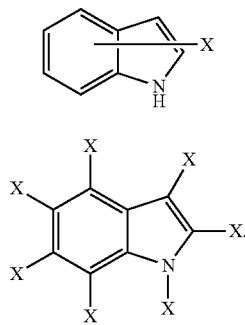

This also applies to multiple ring systems fused to optional ring systems (which would be represented by dotted lines). For example, in Formula D5, X is an optional substituent both for ring A and ring B.

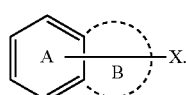

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

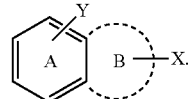

As used herein, the term "alkoxy" refers to an alkyl group, as previously defined, attached to the molecule, or to another chain or ring, through an oxygen ("alkoxy" i.e., —O-alkyl) atom.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be —CFHCH$_2$CHF$_2$ and a $C_{1-2}$ haloalkoxy could be —OC(Br)HCHF$_2$. This term includes perfluorinated alkyl groups, such as —CF$_3$ and —CF$_2$CF$_3$.

As used herein, the term "cyano" refers to —CN or —C≡N.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example a $C_{1-3}$ cyanoalkyl could be —C(CN)$_2$CH$_2$CH$_3$ and a $C_{1-2}$ cyanoalkenyl could be =CHC(CN)H$_2$.

As used herein, an "amino" group refers to —NH$_2$.

The terms "aminoalkyl", "aminoalkenyl", "aminoaliphatic", and "aminoalkoxy" mean alkyl, alkenyl, aliphatic or alkoxy, as the case may be, substituted with one or more amino groups. For example a $C_{1-3}$ aminoalkyl could be —CH(NH$_2$)CH$_2$CH$_2$NH$_2$ and a $C_{1-2}$ aminoalkoxy could be —OCH$_2$CH$_2$NH$_2$.

The term "hydroxyl" or "hydroxy" refers to —OH.

The terms "hydroxyalkyl", "hydroxyalkenyl", "hydroxyaliphatic", and "hydroxyalkoxy" mean alkyl, alkenyl, aliphatic or alkoxy, as the case may be, substituted with one or more —OH groups. For example a $C_{1-3}$ hydroxyalkyl could be —CH$_2$(CH$_2$OH)CH$_3$ and a $C_4$ hydroxyalkoxy could be —OCH$_2$C(CH$_3$)(OH)CH$_3$.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to =O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g. —CH$_2$—C(O)—CH$_3$. When an "oxo' group is listed as a possible substituent on a ring or another moiety or group (e.g. an alkyl chain) it will be understood that the bond between the oxygen in said oxo group and the ring, or moiety it is attached to will be a double bond, even though sometimes it may be drawn generically with a single line. For example, in the example depicted below, J$^D$ attached to the ring may be selected from a number of different substituents. When $J^D$ is oxo, it will be understood that the bond between $J^D$ and the ring is a double bond. When $J^D$ is a halogen, it will be understood that the bond between $J^D$ and the ring is a single bond. In some instances, for example when the ring contains an unsaturation or it has aromatic character, the compound may exist in two or more possible tautomeric forms. In one of them the bond between the oxo group and the ring will be a double bond. In the other one, a hydrogen bond will be exchanged between atoms and substituents in the ring, so that the oxo becomes a hydroxy and an additional double bond is formed in the ring. Whereas the compound is depicted as D7 or D8, both will be taken to represent the set of all possible tautomers for that particular compound.

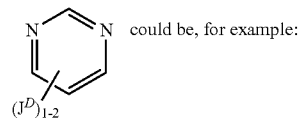

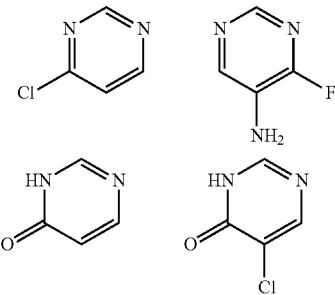

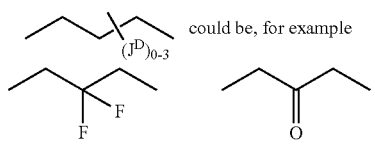

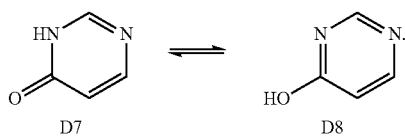

In all other situations, a "linker", as used herein, refers to a divalent group in which the two free valences are on different atoms (e.g. carbon or heteroatom) or are on the same atom but can be substituted by two different substituents. For example, a methylene group can be $C_1$ alkyl linker (—$CH_2$—) which can be substituted by two different groups, one for each of the free valences (e.g. as in Ph-$CH_2$-Ph, wherein methylene acts as a linker between two phenyl rings). Ethylene can be $C_2$ alkyl linker (—$CH_2CH_2$—) wherein the two free valences are on different atoms. The amide group, for example, can act as a linker when placed in an internal position of a chain (e.g. —CONH—). The compounds of the invention are defined herein by their chemical structures and/or chemical names. Where a compound is referred to by both a chemical structure and a chemical name, and the chemical structure and chemical name conflict, the chemical structure is determinative of the compound's identity.

COMPOUND EMBODIMENTS

The present invention is directed to compounds of Formula I, or pharmaceutically acceptable salts thereof,

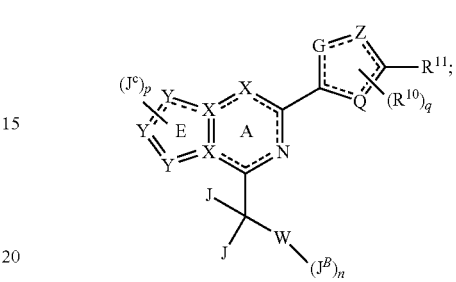

Formula I wherein:
rings E and A form the core of the molecule and are aromatic; each instance of X and Y is independently selected from N or C; wherein a maximum of 4 instances of X and Y are simultaneously N;
W is either
i) absent, with $J^B$ connected directly to the carbon atom bearing two J groups, each J is independently selected from hydrogen or methyl, n is 1 and $J^B$ is a $C_{1-7}$ alkyl chain optionally substituted by up to 9 instances of fluorine; or
ii) a ring B that is a phenyl, a $C_{3-7}$ cycloalkyl ring or a 5 or 6-membered heteroaryl ring, containing 1 or 2 ring nitrogen atoms;
wherein when ring B is the phenyl or 5 or 6-membered heteroaryl ring; each J is independently selected from hydrogen or methyl; n is an integer selected from 0 to 3; and each $J^B$ is independently selected from halogen, —CN, a $C_{1-6}$ aliphatic, —$OR^B$ or a $C_{3-8}$ cycloaliphatic ring; and
wherein when ring B is the $C_{3-7}$ cycloalkyl ring; each J is hydrogen; n is an integer selected from 0 to 3 and each $J^B$ is independently selected from halogen, —CN, a $C_{1-6}$ aliphatic or —$OR^{B1}$;
wherein each $J^B$ that is a $C_{1-6}$ aliphatic and each $J^B$ that is a $C_{3-8}$ cycloaliphatic ring is optionally and independently substituted with up to 3 instances of $R^3$;
each $R^B$ is independently selected from a $C_{1-6}$ aliphatic or a $C_{3-8}$ cycloaliphatic ring; said $R^B$ optionally and independently substituted with up to 3 instances of $R^{3a}$;
each $R^{B1}$ is independently selected from hydrogen, a $C_{1-6}$ aliphatic or a $C_{3-8}$ cycloaliphatic ring; wherein each of said $C_{1-6}$ aliphatic and each of said $C_{3-8}$ cycloaliphatic ring is optionally and independently substituted with up to 3 instances of $R^{3b}$;
each $R^3$, $R^{3a}$ and $R^{3b}$ is, in each instance, independently selected from halogen, —CN, $C_{1-4}$ alkyl, $C_{1-4}$ haloalkyl, —O($C_{1-4}$ alkyl) or —O($C_{1-4}$ haloalkyl);
p is an integer selected from 1, 2 or 3;
each $J^C$ is independently selected from hydrogen, halogen, $C_{1-4}$ aliphatic, $C_{1-4}$ alkoxy or —CN; wherein each said $C_{1-4}$ aliphatic and each said $C_{1-4}$ alkoxy is optionally and independently substituted by up to 3 instances of $C_{1-4}$ alkoxy, $C_{1-4}$ haloalkoxy, —OH or halogen;
Q, G and Z are each independently N, S or O, wherein at least two of Q, G and Z are N;
q is 0, 1 or 2;

$R^{10}$ is $C_{1-6}$ alkyl optionally and independently substituted with 0-3 occurrences of $R^{15}$, phenyl optionally and independently substituted with 0-3 occurrences of $R^{15}$, 5- or 6-membered heteroaryl optionally and independently substituted with 0-3 occurrences of $R^{15}$, $C_{3-8}$ cycloalkyl optionally and independently substituted with 0-3 occurrences of $R^{15}$ or 3-8 membered heterocyclyl optionally and independently substituted with 0-3 occurrences of $R^{15}$; wherein each of said 5- to 6-membered heteroaryl ring and each of said 3-8 membered heterocyclyl contains up to 3 ring heteroatoms independently selected from N, O or S;

$R^{11}$ is H, $-NR^{a2}R^{b2}$, $-C(O)NR^{a2}R^{b2}$, $-C(O)R^{15a}$, $-SO_2R^{b2}$, halo, $-OCF_3$, $-CN$, hydroxyl, $C_{2-6}$ alkenyl optionally and independently substituted with 0-2 occurrences of $R^{b2}$, $C_{2-6}$ alkynyl optionally and independently substituted with 0-2 occurrences of $R^{b2}$; $C_{1-6}$ alkyl optionally and independently substituted with 0-5 occurrences of $R^{15}$, $C_{1-6}$ alkoxy optionally and independently substituted with 0-3 occurrences of $R^{15}$, phenyl optionally and independently substituted with 0-3 occurrences of $R^{15}$, 5- or 6-membered heteroaryl optionally and independently substituted with 0-3 occurrences of $R^{15}$, $C_{3-8}$ cycloalkyl optionally and independently substituted with 0-3 occurrences of $R^{15}$ or 3-8 membered heterocyclyl optionally and independently substituted with 0-3 occurrences of $R^{15}$; wherein each of said 5- to 6-membered heteroaryl and each of said 3-8 membered heterocyclyl contains up to 3 ring heteroatoms independently selected from N, O or S; or when $R^{10}$ is a substituent of Z, $R^{10}$ and $R^{11}$, taken together with Z and the carbon to which $R^{11}$ is attached form a 3 to 10-membered heterocyclic ring optionally and independently substituted with 0-3 occurrences of $R^{15}$; wherein each of said 3 to 10 membered heterocyclyl contains up to 3 ring heteroatoms independently selected from N, O or S;

$R^{15}$ is halo, $-OR^{b2}$, $-SR^{b2}$, $-NR^{a2}R^{b2}$, $-C(O)R^{b2}$, $-C(O)NR^{a2}R^{b2}$, $-NR^{b2}C(O)OR^{b2}$, $-OC(O)NR^{a2}R^{b2}$, $C_{2-4}$ alkenoxy, $C_{3-8}$ cycloalkyl optionally and independently substituted with 0-3 occurrences of $R^{18}$, phenyl optionally and independently substituted with 0-3 occurrences of $R^{18}$, 5- or 6-membered heteroaryl optionally and independently substituted with 0-3 occurrences of $R^{18}$ or 3-10 membered heterocyclyl optionally and independently substituted with 0-3 occurrences of $R^{18}$; wherein each of said 3-10 membered heterocyclyl contains up to 3 ring heteroatoms independently selected from N, O or S;

$R^{15a}$ is $C_{3-8}$ cycloalkyl optionally and independently substituted with 0-3 occurrences of $R^{18}$, phenyl optionally and independently substituted with 0-3 occurrences of $R^{18}$, 5- or 6-membered heteroaryl optionally and independently substituted with 0-3 occurrences of $R^{18}$ or 3-10 membered heterocyclyl optionally and independently substituted with 0-3 occurrences of $R^{18}$; wherein each of said 5- or 6-membered heteroaryl ring and each of said 3-10 membered heterocyclyl contains up to 3 ring heteroatoms independently selected from N, O or S;

each $R^{18}$ is independently selected from halo, hydroxyl, $C_{1-6}$ alkyl, $C_{1-6}$ alkoxy, $C_{1-6}$ haloalkyl or phenyl;

$R^{a2}$ is hydrogen, $-C(O)R^{b2}$, $C_{1-6}$ alkyl or $C_{1-6}$ haloalkyl; and $R^{b2}$ is hydrogen, $C_{1-6}$ alkyl or $C_{1-6}$ haloalkyl.

In some embodiments of Formula I, W is absent and the compound is one of Formula IIA, or a pharmaceutically acceptable salt thereof:

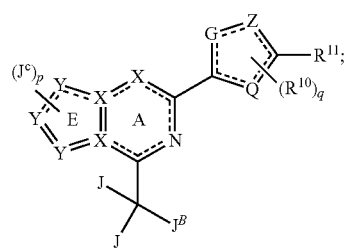

Formula IIA wherein $J^B$ is a $C_{1-7}$ alkyl chain optionally substituted by up to 9 instances of fluorine. In some embodiments of Formula IIA, $J^B$ is a $C_{1-4}$ alkyl chain, optionally substituted by up to 5 instances of fluorine. In other embodiments, $J^B$ is a $C_{1-2}$ alkyl chain, optionally substituted by up to 5 instances of fluorine. In still other instances, $J^B$ is an ethyl chain, optionally substituted by either 3 or 5 instances of fluorine.

In some embodiments of Formula I, W is a ring B and the compound is one of Formula IIB, or a pharmaceutically acceptable salt thereof:

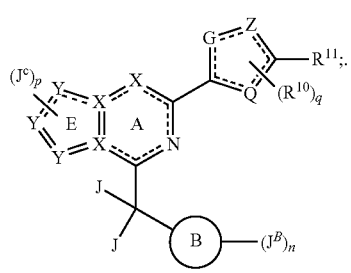

Formula IIB

In some embodiments of Formula IIB, n is an integer selected from 1 or 2 and each $J^B$ is independently selected from halogen, a $C_{1-4}$ alkyl, $-OR^B$ or $-OR^{B1}$. In other embodiments, each $J^B$ is independently selected from halogen atoms. In still other embodiments, each $J^B$ is independently selected from fluoro or chloro. In yet other embodiments, each $J^B$ is fluoro.

In some embodiments of Formula IIB, each $J^B$ is a $C_{1-4}$ alkyl. In some of these embodiments, $J^B$ is ethyl or methyl. In some embodiments, $J^B$ is methyl.

In some embodiments of Formula IIB, n is 0.

In some embodiments of Formula IIB, n is 1.

In some embodiments of Formula IIB, n is 1 and $J^B$ is independently selected from halogen, a $C_{1-4}$ alkyl, $-OR^B$ or $-OR^{B1}$. In some of these embodiments, $J^B$ is halogen. In some embodiments, $J^B$ is chloro or fluoro. In other embodiments, $J^B$ is fluoro. In still other embodiments, $J^B$ is $C_{1-4}$ alkyl. In still other embodiments, $J^B$ is methyl or ethyl.

In some embodiments of Formula IIB, n is 2 and each $J^B$ is a halogen atom. In some of these embodiments, each $J^B$ is independently selected from chloro or fluoro. In other embodiments, one $J^B$ is fluoro and the other $J^B$ is chloro. In still other embodiments, each $J^B$ is fluoro.

In some embodiments of Formula IIB, ring B is phenyl. In some of these embodiments, n is 1 or 2. In some of these embodiments, a $J^B$ is ortho to the attachment of the methylene linker between ring B and the core of the molecule, and the $J^B$ is halogen. In some of these embodiments, $J^B$ is chloro. In other embodiments, $J^B$ is fluoro.

In some embodiments of Formula IIB, ring B is a 6-membered heteroaryl ring. In other embodiments, ring B is a pyridyl ring. In still other embodiments, ring B is a pyrimidinyl ring.

In some embodiments of Formula IIB, ring B is a $C_{3-7}$ cycloalkyl ring.

In some embodiments of Formula I, Formula IIA or Formula IIB, G, Z and Q are each N.

In some embodiments of Formula I or Formula IIB, the compound is one of Formula III, or a pharmaceutically acceptable salt thereof, or any of its tautomers:

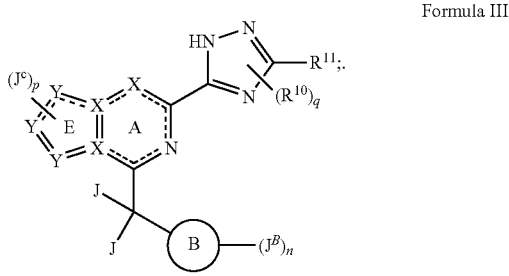

Formula III

In some embodiments of Formula I, Formula IIA, Formula IIB and Formula III, $R^{11}$ is H, $NR^{a2}R^{b2}$, —C(O)$NR^{a2}R^{b2}$, —C(O)$R^{15a}$, —$SO_2R^{b2}$, —$SR^{b2}$, halo, —$OCF_3$, —CN, hydroxyl, $C_{2-6}$ alkenyl optionally and independently substituted with 0-2 occurrences of $R^{b2}$, $C_{2-6}$ alkynyl optionally and independently substituted with 0-2 occurrences of $R^{b2}$; $C_{1-6}$ alkyl optionally and independently substituted with 0-5 occurrences of $R^{15}$, $C_{1-6}$ alkoxy optionally and independently substituted with 0-3 occurrences of $R^{15}$, phenyl optionally and independently substituted with 0-3 occurrences of $R^{15}$, 5- or 6-membered heteroaryl optionally and independently substituted with 0-3 occurrences of $R^{15}$, $C_{3-8}$ cycloalkyl optionally and independently substituted with 0-3 occurrences of $R^{15}$ or 3-8 membered heterocyclyl optionally and independently substituted with 0-3 occurrences of $R^{15}$. In some further embodiments, $R^{11}$ is H or $C_{1-6}$ alkyl optionally and independently substituted with 0-5 occurrences of $R^{15}$. In some further embodiments, $R^{11}$ is $C_{1-6}$ alkyl optionally substituted with 0-5 occurrences of $R^{15}$. In some further embodiments, $R^{11}$ is methyl optionally substituted with 0-3 occurrences of $R^{15}$. In some further embodiments, $R^{11}$ is methyl optionally substituted with 0-3 occurrences of $R^{15}$, and $R^{15}$ is halo (e.g., fluoro). In some further embodiments, $R^{11}$ is methyl optionally substituted with 0-3 occurrences of $R^{15}$, and $R^{15}$ is fluoro. In some further embodiments, $R^{11}$ is unsubstituted methyl. In some further embodiments, $R^{11}$ is methyl substituted with 2 occurrences of $R^{15}$. In some further embodiments, $R^{11}$ is methyl substituted with 2 occurrences of R and $R^{15}$ is halo. In some further embodiments, $R^{11}$ is —$CF_2H$. In some embodiments, $R^{11}$ is methyl substituted with 3 occurrences of $R^{15}$. In some embodiments, $R^{11}$ is methyl substituted with 3 occurrences of $R^{15}$ and $R^{15}$ is halo. In some embodiments, $R^{11}$ is —$CF_3$.

In some embodiments of Formula I, Formula IIA, Formula IIB and Formula III, $R^{11}$ is ethyl substituted with 0-5 occurrences of $R^{15}$. In some further embodiments, $R^{11}$ is ethyl substituted with 5 occurrences of $R^{15}$ and $R^{15}$ is halo. In some further embodiments, $R^{11}$ is ethyl substituted with 5 occurrences of $R^{15}$ and $R^{15}$ is fluoro.

In some embodiments of Formula III, n is an integer selected from 1 or 2 and each $J^B$ is independently selected from halogen, a $C_{1-4}$ alkyl, —$OR^B$ or —$OR^{B1}$. In other embodiments, each $J^B$ is independently selected from halogen atoms. In still other embodiments, each $J^B$ is independently selected from fluoro or chloro. In yet other embodiments, each $J^B$ is fluoro.

In some embodiments of Formula III, each $J^B$ is a $C_{1-4}$ alkyl. In some of these embodiments, $J^B$ is ethyl or methyl. In some embodiments, $J^B$ is methyl.

In some embodiments of Formula III, n is 0.

In some embodiments of Formula III, n is 1.

In some embodiments of Formula III, n is 1 and each $J^B$ is independently selected from halogen, a $C_{1-4}$ alkyl, —$OR^B$ or —$OR^{B1}$. In some of these embodiments, $J^B$ is halogen. In some embodiments, $J^B$ is chloro or fluoro. In other embodiments, $J^B$ is fluoro. In still other embodiments, $J^B$ is $C_{1-4}$ alkyl. In still other embodiments, $J^B$ is methyl or ethyl.

In some embodiments of Formula III, n is 2 and each $J^B$ is a halogen atom. In some of these embodiments, each $J^B$ is independently selected from chloro or fluoro. In other embodiments, one $J^B$ is fluoro and the other $J^B$ is chloro. In still other embodiments, each $J^B$ is fluoro.

In some embodiments of Formula III, ring B is phenyl. In some of these embodiments, n is 1 or 2. In some of these embodiments, a $J^B$ is ortho to the attachment of the methylene linker between ring B and the core of the molecule, and the $J^B$ is halogen. In some of these embodiments, $J^B$ is chloro. In other embodiments, $J^B$ is fluoro.

In some embodiments of Formula III, ring B is a 6-membered heteroaryl ring. In other embodiments, ring B is a pyridyl ring. In still other embodiments, ring B is a pyrimidinyl ring.

In some embodiments of Formula III, ring B is a $C_{3-7}$ cycloalkyl ring.

In some embodiments of Formula I, Formula IIA, Formula IIB and Formula III, q is 0. In some of these embodiments, $R^{11}$ is $C_{1-6}$ alkyl optionally and independently substituted with 0-3 occurrences of $R^{15}$. In some further embodiments, $R^{11}$ is methyl optionally and independently substituted with 0-3 occurrences of $R^{15}$ and $R^{15}$ is halo (e.g., fluoro). In some further embodiments, $R^{11}$ is methyl independently substituted with 2 occurrences of $R^{15}$ and $R^{15}$ is halo (e.g., fluoro). In some embodiments, $R^{11}$ is methyl independently substituted with 3 occurrences of $R^{15}$ and $R^{15}$ is halo (e.g., fluoro).

In some embodiments of Formula I, Formula IIA, Formula IIB and Formula III, the core formed by rings E and A is selected from:

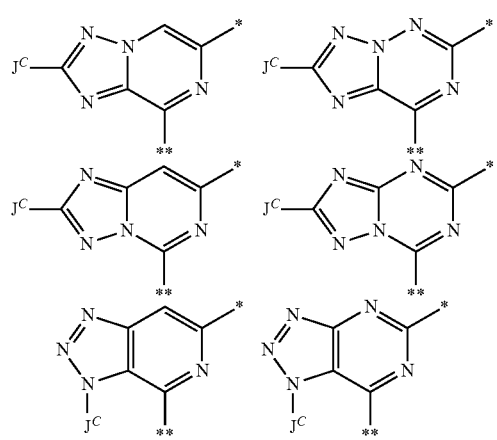

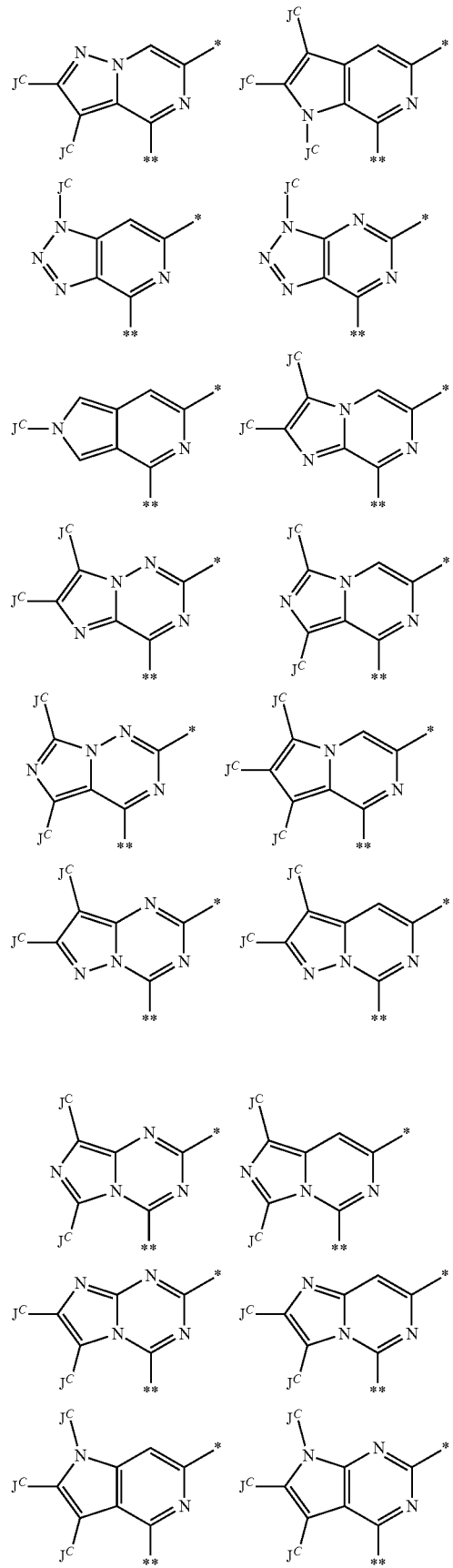
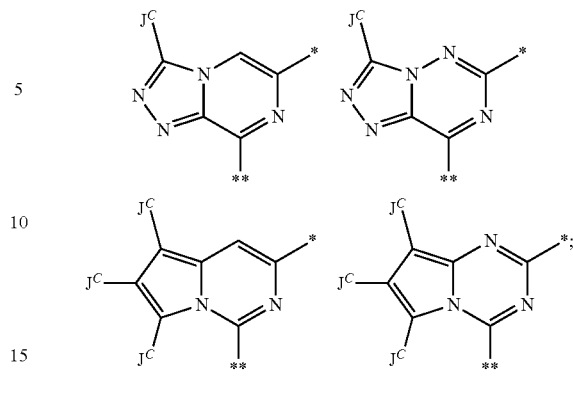

wherein the C atom with a symbol * represents the attachment point to the ring containing G, Z, and Q and the C atom with a symbol ** represents the point of attachment of the 2 instances of J. In some of these embodiments, each instance of $J^C$ is hydrogen.

In some embodiments of Formula I, Formula IIA, Formula IIB and Formula III, the core formed by rings E and A is selected from:

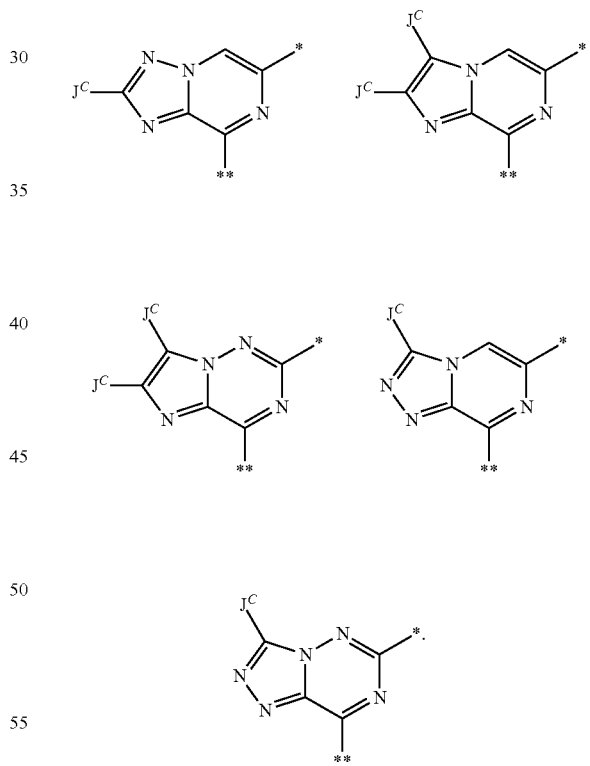

In some of these embodiments, each instance of $J^C$ is hydrogen.

In some embodiments of Formula I, Formula IIA, Formula IIB and Formula III, Q, G and Z are each independently N, NH, S or O, wherein at least two of Q, G and Z are N or NH.

In some embodiments of Formula I, the compound is one of Formula IV, or a pharmaceutically acceptable salt thereof:

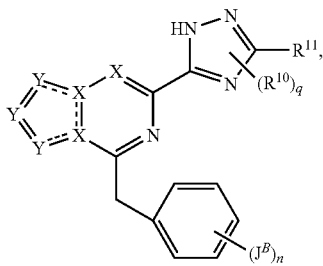

Formula IV

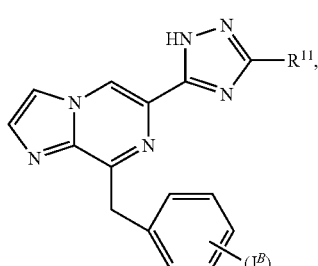

Formula VI wherein:
Each Y is independently selected from N, NJ$^c$, CH, or CJ$^c$;
Each X is either N, NJ$^c$, CH, or CJ$^c$;
wherein a maximum of 3 instances of X and Y are simultaneously N or NJ$^c$;
J$^c$ is halo, CN, or C$_{1-3}$alkyl optionally substituted with 1 to 3 halo;
Each J$^B$ is independently selected from halo or C$_{1-4}$alkyl;
n is 0, 1, 2, or 3;
R$^{10}$ is C$_{1-4}$alkyl optionally substituted with 1, 2, or 3 groups independently selected from halo, —C(O)R$^{b2}$, phenyl, and 5- or 6-membered heteroaryl, wherein the phenyl and 5- or 6-membered heteroaryl are optionally substituted with 1, 2, or 3 halo or C$_{1-4}$alkyl, wherein the heteroaryl includes 1, 2, or 3 heteroatoms independently selected from N, O, and S;
q is 0 or 1;
R$^{11}$ is H, halo, —NR$^{a2}$R$^{b2}$, C$_{1-4}$alkyl, 5- to 6-membered heteroaryl, or C$_{3-6}$ cycloalkyl, wherein the C$_{1-4}$alkyl, 5- to 6-membered heteroaryl, and C$_{3-6}$ cycloalkyl are each optionally substituted with 1, 2, or 3 groups independently selected from halo, wherein the heteroaryl includes 1, 2, or 3 heteroatoms independently selected from N, O, and S;
R$^{a2}$ is hydrogen or C$_{1-4}$ alkyl; and
R$^{b2}$ is hydrogen or C$_{1-4}$ alkyl.

In some embodiments of Formula I, the compound is one of Formula V, or a pharmaceutically acceptable salt thereof:

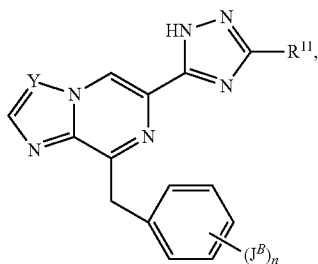

Formula V

Wherein:
Y is N or CH;
Each J$^B$ is independently selected from halo or C$_{1-4}$alkyl;
n is 0, 1, 2, or 3;
R$^{11}$ is H, halo, —NR$^{a2}$R$^{b2}$, C$_{1-4}$alkyl, 5- to 6-membered heteroaryl, or C$_{3-6}$ cycloalkyl, wherein the C$_{1-4}$ alkyl, 5- to 6-membered heteroaryl, and C$_{3-6}$ cycloalkyl are each optionally substituted with 1, 2, or 3 groups independently selected from halo;
R$^{a2}$ is hydrogen or C$_{1-4}$ alkyl; and
R$^{b2}$ is hydrogen or C$_{1-4}$ alkyl.

In some embodiments of Formula I, the compound is one of Formula VI, or a pharmaceutically acceptable salt thereof:

Wherein:
Y is N or CH;
Each J$^B$ is independently selected from halo or C$_{1-4}$alkyl;
n is 0, 1, 2, or 3;
R$^{11}$ is H, halo, —NR$^{a2}$R$^{b2}$, C$_{1-4}$alkyl, 5- to 6-membered heteroaryl, or C$_{3-6}$ cycloalkyl, wherein the C$_{1-4}$alkyl, 5- to 6-membered heteroaryl, and C$_{3-6}$ cycloalkyl are each optionally substituted with 1, 2, or 3 groups independently selected from halo;
R$^{a2}$ is hydrogen or C$_{1-4}$ alkyl; and
R$^{b2}$ is hydrogen or C$_{1-4}$ alkyl.

In some embodiments of Formulas IV, V and VI, R$^{11}$ is C$_{1-4}$alkyl optionally substituted with 1, 2, or 3 halo.

In some embodiments, the compounds of Formula I are selected from those listed in Table I.

TABLE I

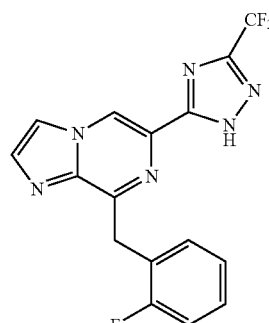

I-1

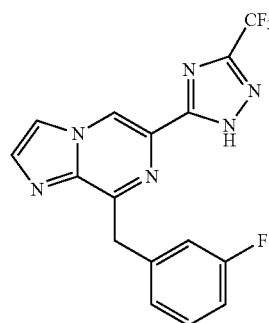

I-2

TABLE I-continued
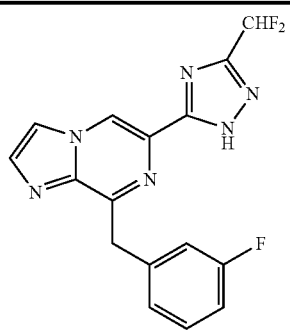 I-3
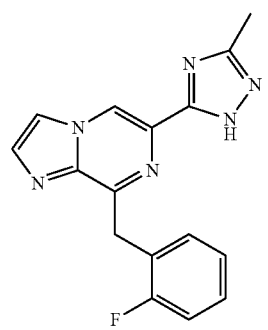 [SMILES: Cc1n[nH]c(-c2cn3ccnc3c(Cc3ccccc3F)n2)n1] I-4
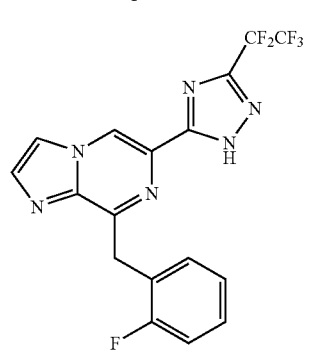 I-5
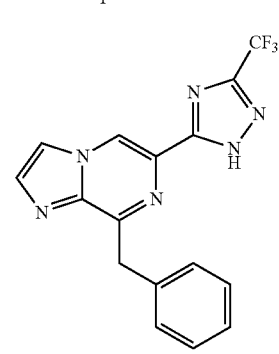 I-6
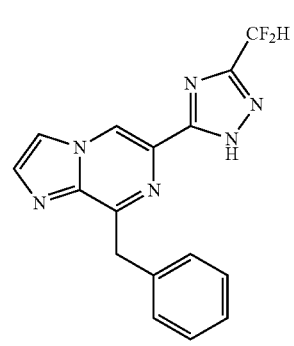 [SMILES: FC(F)c1n[nH]c(-c2cn3ccnc3c(Cc3ccccc3)n2)n1] I-7
TABLE I-continued
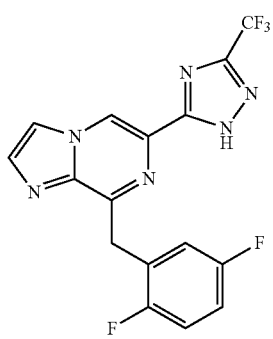 [SMILES: Fc1ccc(F)c(Cc2nc(-c3nc(C(F)(F)F)n[nH]3)cn3ccnc23)c1] I-8
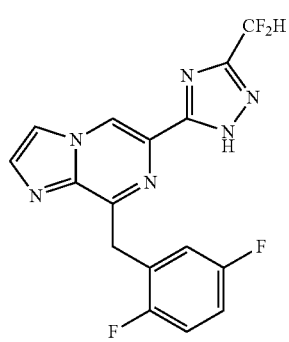 [SMILES: Fc1ccc(F)c(Cc2nc(-c3nc(C(F)F)n[nH]3)cn3ccnc23)c1] I-9
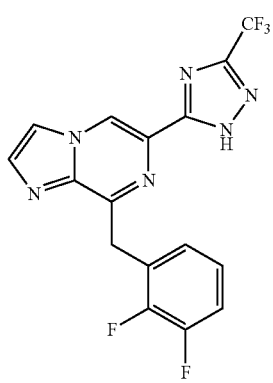 [SMILES: Fc1cccc(Cc2nc(-c3nc(C(F)(F)F)n[nH]3)cn3ccnc23)c1F] I-10
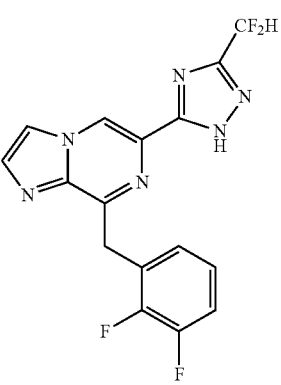 [SMILES: Fc1cccc(Cc2nc(-c3nc(C(F)F)n[nH]3)cn3ccnc23)c1F] I-11

TABLE I-continued
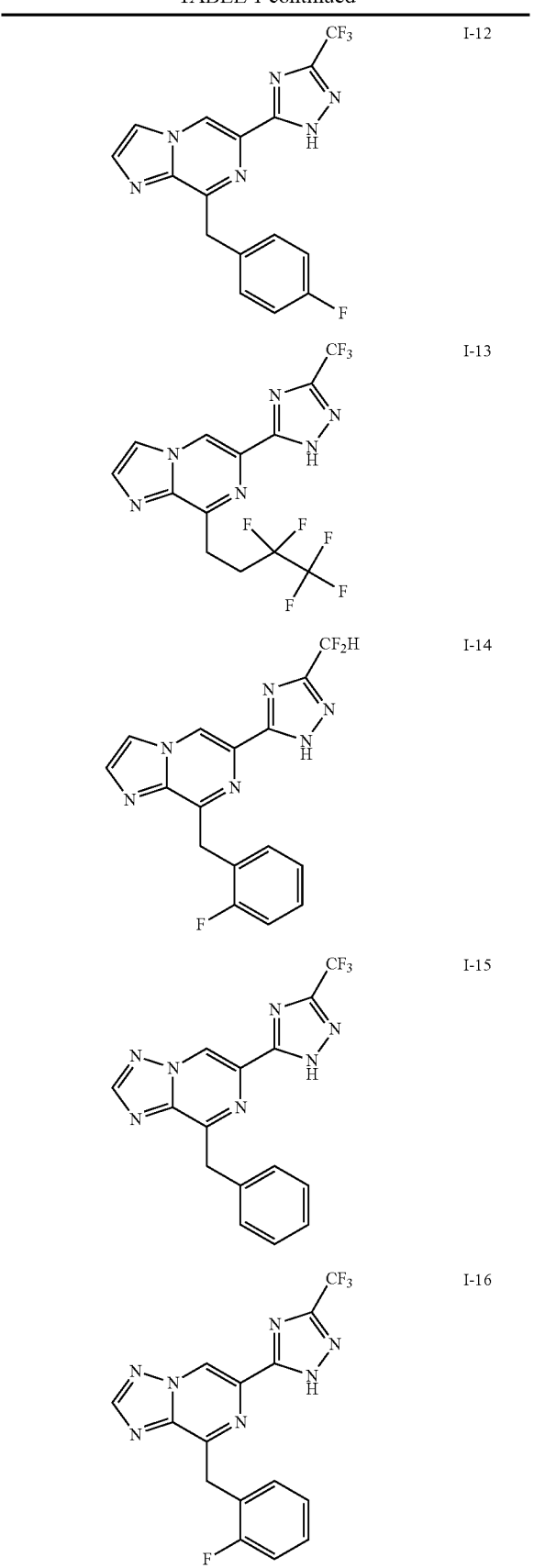
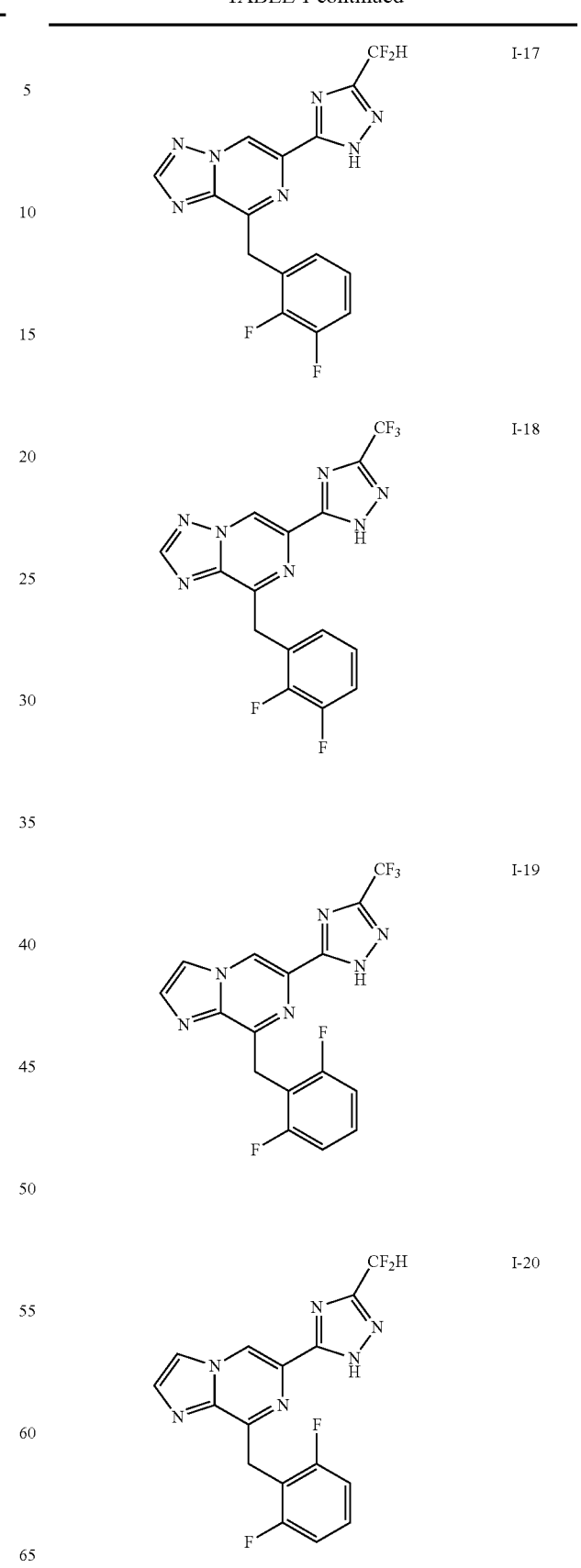

TABLE I-continued
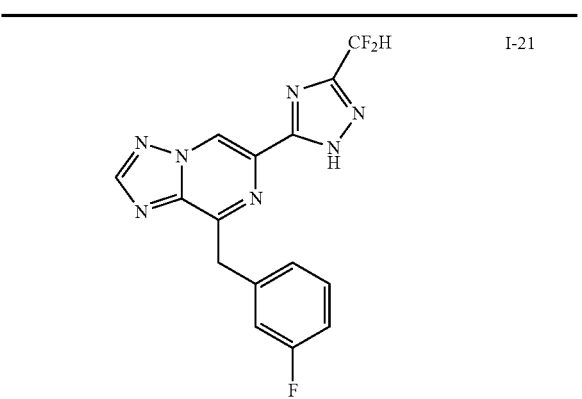
I-21
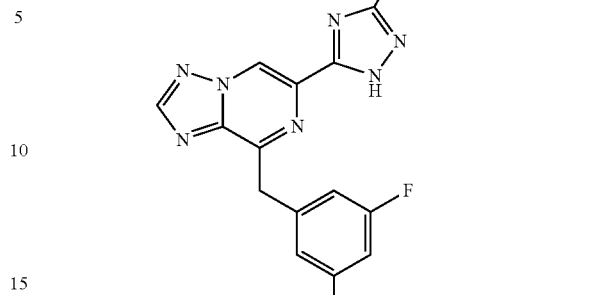
I-25
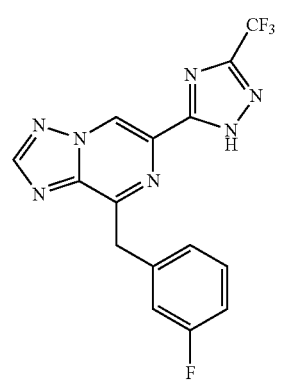 [SMILES: Fc1cccc(Cc2nc(-c3nc(C(F)(F)F)n[nH]3)cn3ncnc23)c1]
I-22
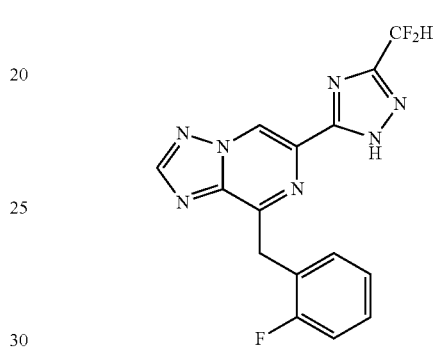
I-26
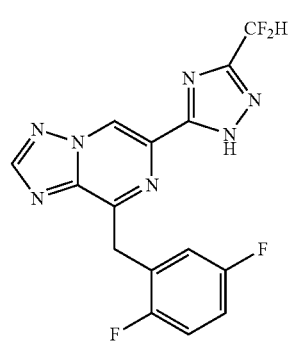 [SMILES: Fc1ccc(F)c(Cc2nc(-c3nc(C(F)F)n[nH]3)cn3ncnc23)c1]
I-23
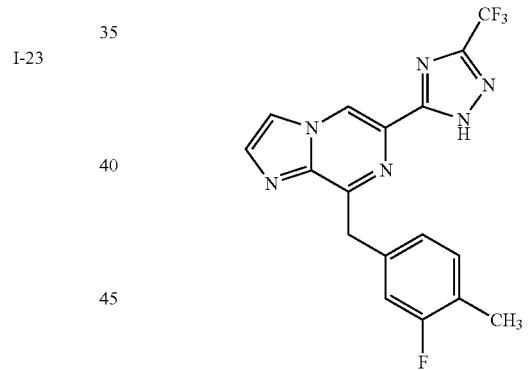
I-27
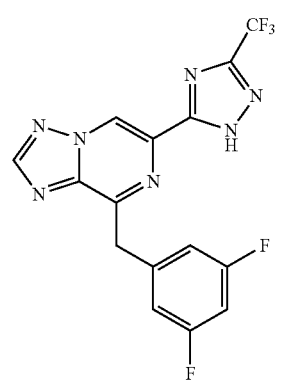 [SMILES: Fc1cc(F)cc(Cc2nc(-c3nc(C(F)(F)F)n[nH]3)cn3ncnc23)c1]
I-24
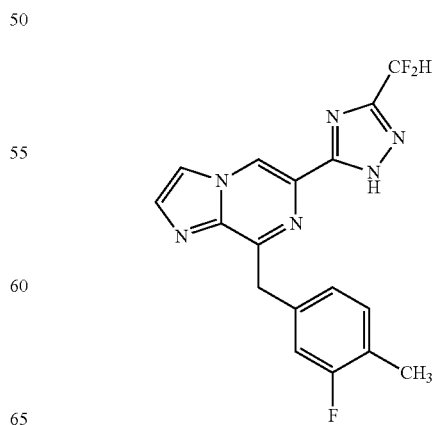
I-28

TABLE I-continued
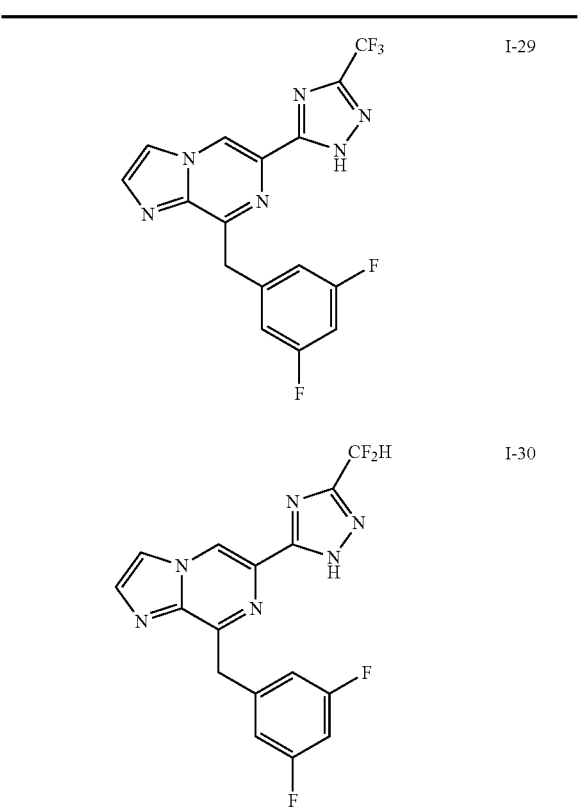
I-29
I-30
I-31
I-32
TABLE I-continued
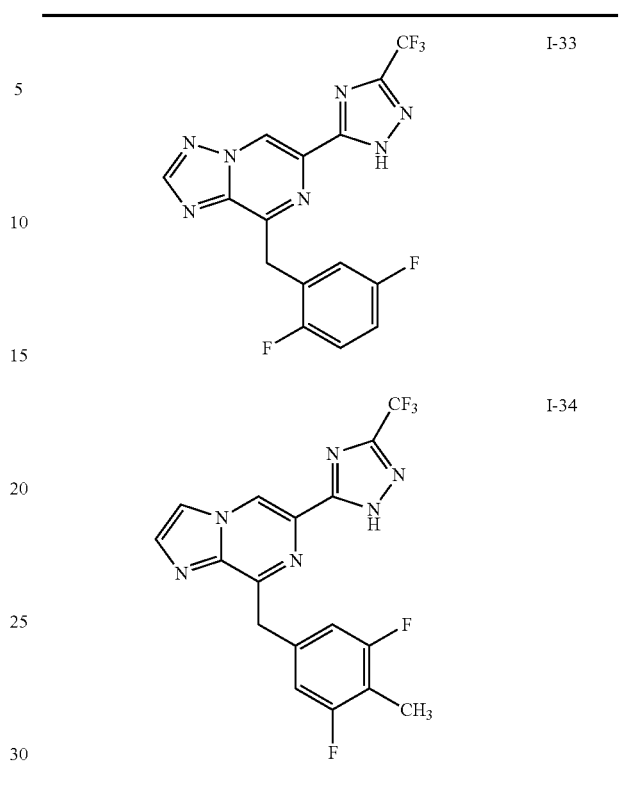
I-33
I-34
I-35
I-36

TABLE I-continued
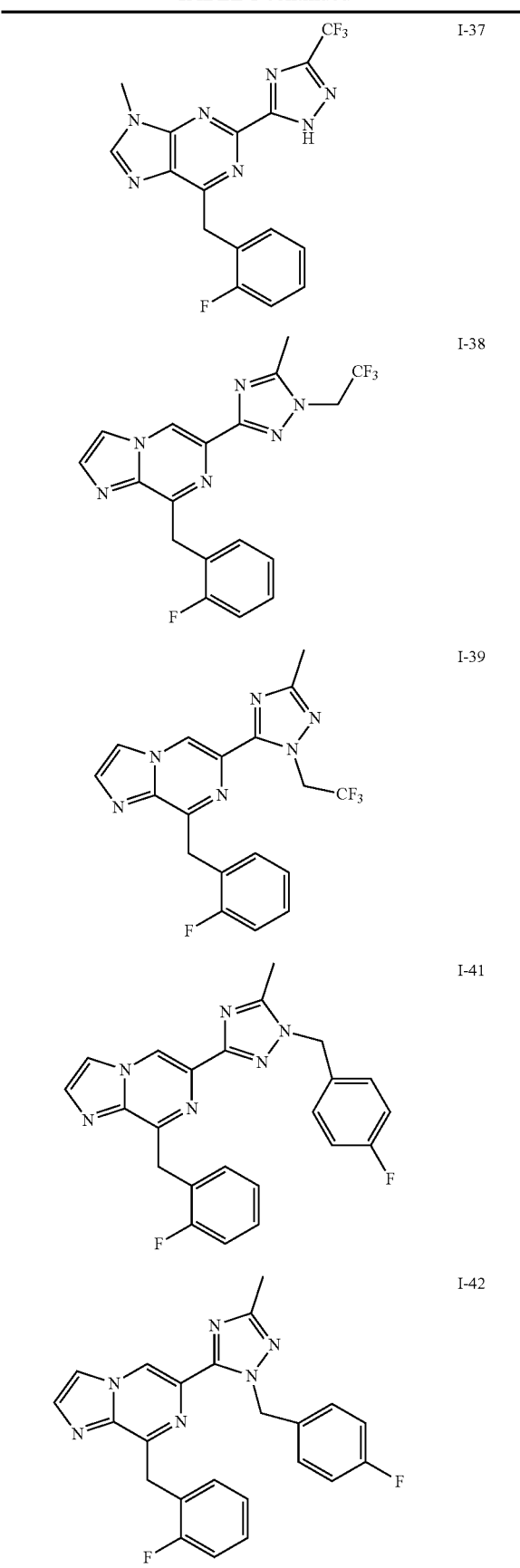
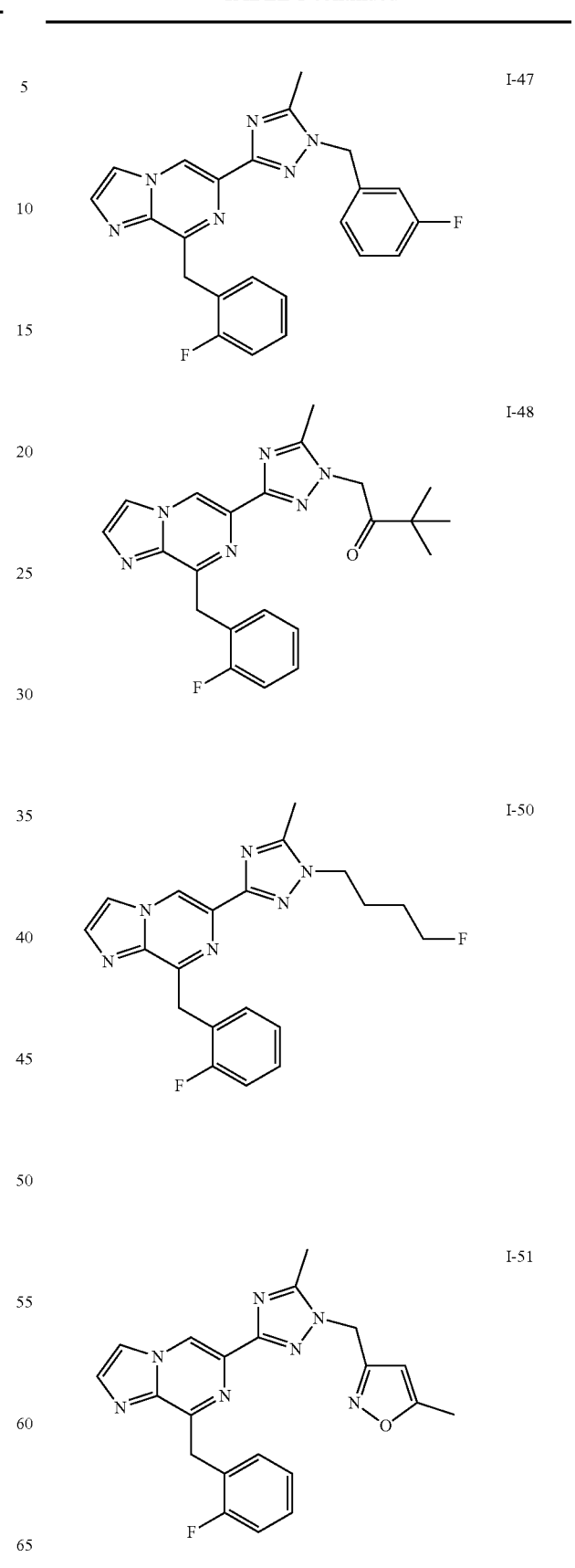

TABLE I-continued
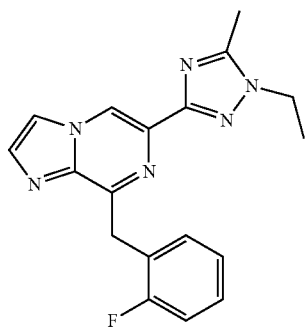 [SMILES: CCn1nc(-c2cn3ccnc3c(Cc3ccccc3F)n2)nc1C]
I-53
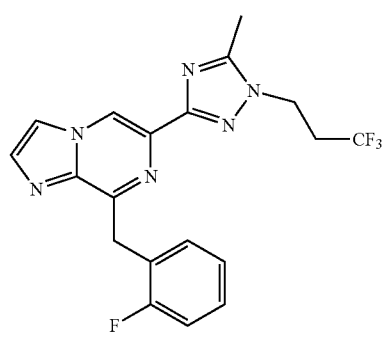 [SMILES: Cc1nc(-c2cn3ccnc3c(Cc3ccccc3F)n2)nn1CCC(F)(F)F]
I-54
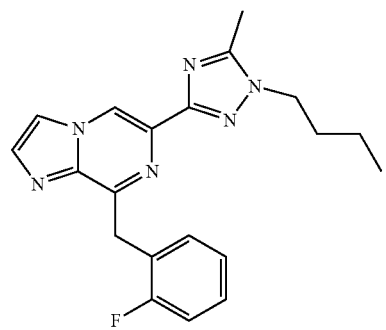 [SMILES: CCCCn1nc(-c2cn3ccnc3c(Cc3ccccc3F)n2)nc1C]
I-56
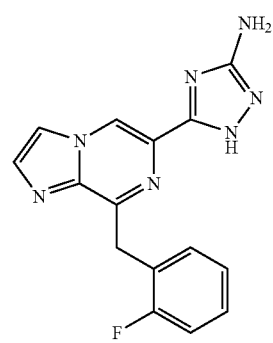 [SMILES: Nc1n[nH]c(-c2cn3ccnc3c(Cc3ccccc3F)n2)n1]
I-57
TABLE I-continued
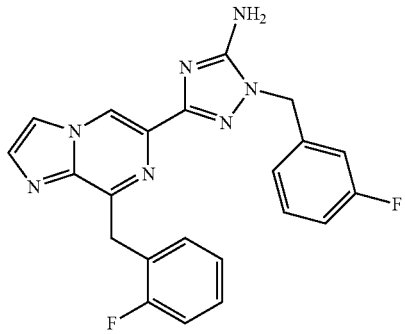 [SMILES: Nc1nc(-c2cn3ccnc3c(Cc3ccccc3F)n2)nn1Cc1cccc(F)c1]
I-58
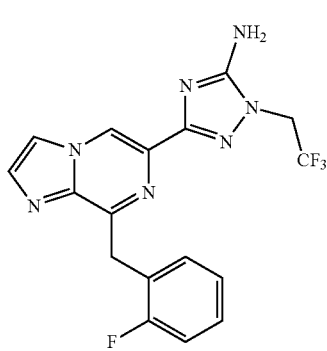 [SMILES: Nc1nc(-c2cn3ccnc3c(Cc3ccccc3F)n2)nn1CC(F)(F)F]
I-59
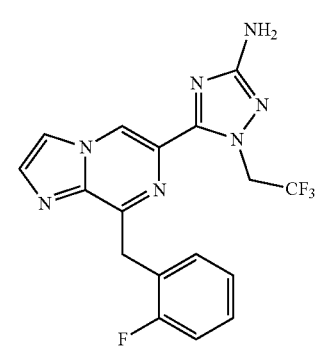 [SMILES: Nc1nc(-c2cn3ccnc3c(Cc3ccccc3F)n2)n(CC(F)(F)F)n1]
I-60
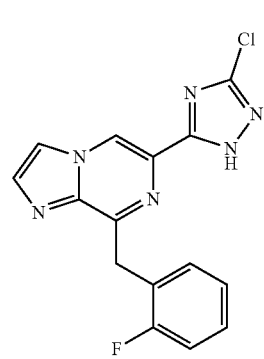 [SMILES: Fc1ccccc1Cc1nc(-c2nc(Cl)n[nH]2)cn2ccnc12]
I-62

TABLE I-continued
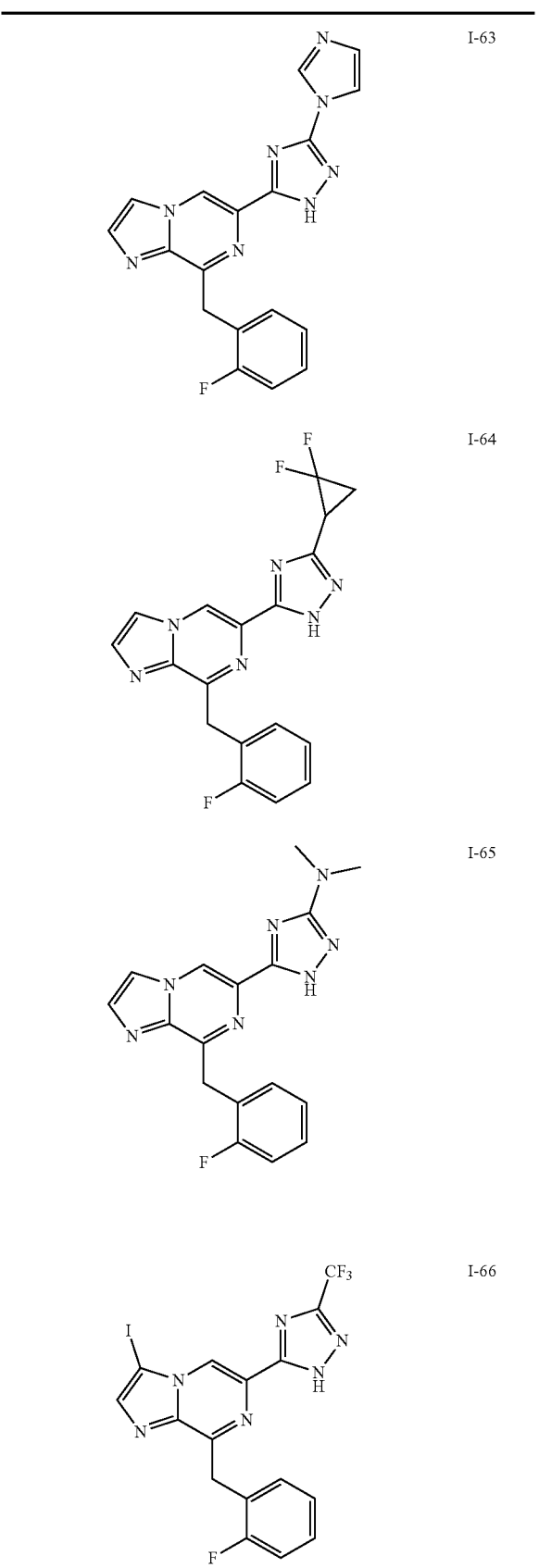
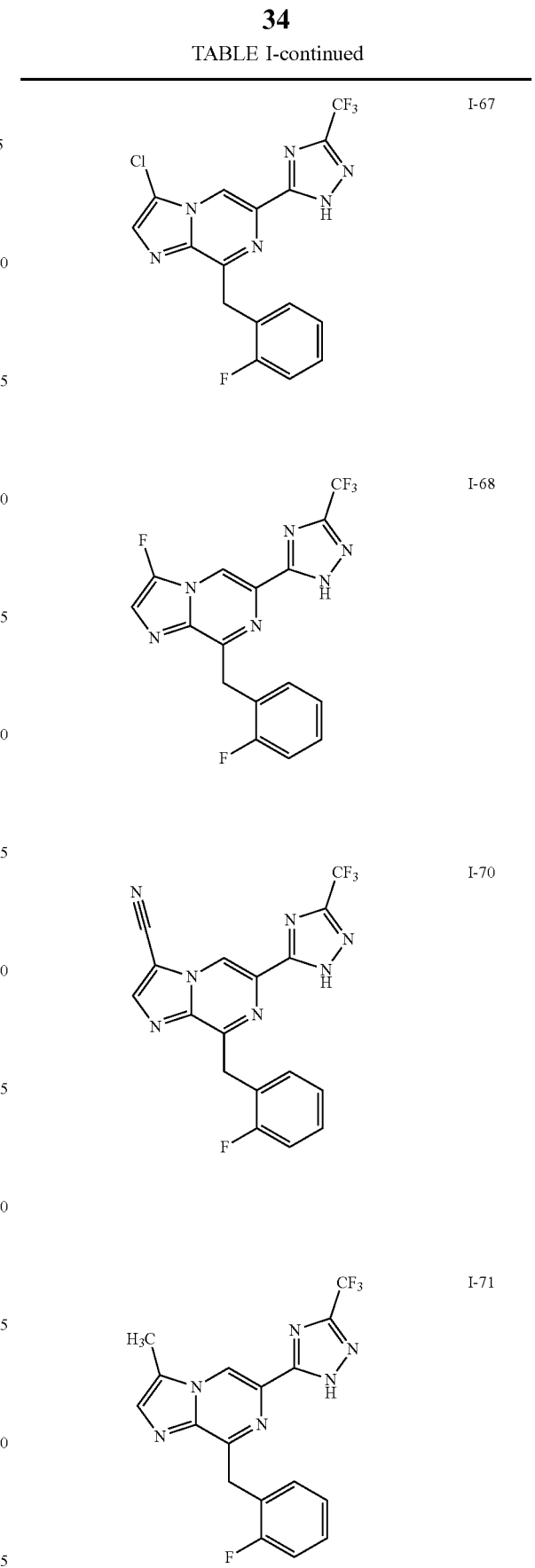

TABLE I-continued

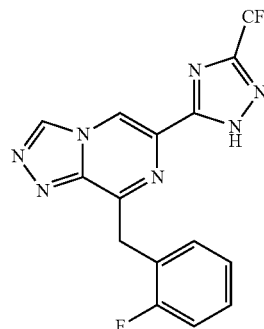

I-72

In some embodiments, the compound of Formula I is either in its neutral form or as a pharmaceutically acceptable salt.
Pharmaceutically Acceptable Salts of the Invention.

The phrase "pharmaceutically acceptable salt," as used herein, refers to pharmaceutically acceptable organic or inorganic salts of a compound of Formula I. The pharmaceutically acceptable salts of a compound of Formula I are used in medicine. Salts that are not pharmaceutically acceptable may, however, be useful in the preparation of a compound of Formula I or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from the compounds with inorganic acids, organic acids or bases. In some embodiments, the salts can be prepared in situ during the final isolation and purification of the compounds. In other embodiments the salts can be prepared from the free form of the compound in a separate synthetic step.

When a compound of Formula I is acidic or contains a sufficiently acidic bioisostere, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N, N'dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a compound of Formula I is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

In addition to the compounds described herein, their pharmaceutically acceptable salts may also be employed in compositions to treat or prevent the herein identified disorders.

Pharmaceutical Compositions and Methods of Administration.

The compounds herein disclosed, and their pharmaceutically acceptable salts thereof may be formulated as pharmaceutical compositions or "formulations".

A typical formulation is prepared by mixing a compound of Formula I, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound of Formula I is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Formula I or pharmaceutical composition thereof) or aid in the manufacturing of the pharmaceutical product (i.e., medicament).

The formulations may be prepared using conventional dissolution and mixing procedures. For example, the bulk drug substance (i.e., a compound of Formula I, a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound of Formula I or a pharmaceutically acceptable salt thereof is typically formulated into pharmaceutical dosage forms to provide an easily controllable dosage of the drug and to enable patient compliance with the prescribed regimen. Pharmaceutical formulations of a compound of Formula I, or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight: weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of Formula I will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nanoparticles and nanocapsules) or in macroemulsions. Such techniques are disclosed in Remington's: The Science and Practice of Pharmacy, $21^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(−)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent deaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LY) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl) methacrylate, and (trimethylaminoethyl) methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g., methyl acrylate-methyl methacrylate copolymers, polyvinyl chloride, polyethylene), hydrophilic polymers (e.g. ethyl cellulose, cellulose acetate, cross linked polyvinylpyrrolidone (also known as crospovidone)), and fatty compounds (e.g. carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semipermeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Non limiting examples of osmotic control devices are disclosed in U.S. patent application Ser. No. 09/495,061.

The amount of water-swellable hydrophilic polymers present in the core may range from about 5 to about 80 wt % (including for example, 10 to 50 wt %). Non limiting examples of core materials include hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly (acrylic) acid, poly (methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolate. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non limiting examples of standard disintegrants include materials such as sodium starch glycolate (e. g., Explotab™ CLV), microcrystalline cellulose (e. g., Avicel™), microcrystalline silicified cellulose (e. g., ProSolv™) and croscarmellose sodium (e. g., Ac-Di-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multilayered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. Nos. 6,419,952, 6,342,249, 5,324,280, 4,672,850, 4,627,850, 4,203,440, and 3,995,631.

As further noted above, the agents described herein may be provided in the form of microparticulates, generally ranging in size from about 10 μm to about 2 mm (including, for example, from about 100 μm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet- and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology, New York: Marcel Dekker, 1992, volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto, 2005, Molecule 10:65-80). Nanocapsules can generally entrap compounds in a stable and reproducible way. To avoid side effects due to intracellular polymeric overloading, ultrafine particles (sized around 0.1 µm) can be designed using polymers able to be degraded in vivo (e.g. biodegradable polyalkyl-cyanoacrylate nanoparticles). Such particles are described in the prior art.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc.), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc.), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Formula I that are suitable for oral administration may be prepared as discrete units such as tablets, pills, troches, lozenges, aqueous or oil suspensions, dispersible powders or granules, emulsions, hard or soft capsules, e.g. gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g. for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a compound of Formula I in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of a compound of Formula I contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Formula I may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Formula I include Tween™-60, Span™-80, cetostearyl alcohol, benzyl alcohol, myristyl alcohol, glyceryl mono-stearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc.) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound of Formula I or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert. In the veterinary art and are compatible with the active ingredient. These veterinary compositions may be administered parenterally, orally or by any other desired route.

Therapeutic Methods

In a third aspect, the invention relates to the treatment of certain disorders by using sGC stimulators, either alone or in combination, or their pharmaceutically acceptable salts or pharmaceutical compositions comprising them, in a patient in need thereof.

The present disclosure relates to stimulators of soluble guanylate cyclase (sGC), pharmaceutical formulations thereof and their use, alone or in combination with one or more additional agents, for treating and/or preventing various diseases, wherein an increase in the concentration of NO or an increase in the concentration of cGMP might be desirable. The diseases that can be treated include but are not limited to pulmonary hypertension, arterial hypertension, heart failure, atherosclerosis, inflammation, thrombosis, renal fibrosis and failure, liver cirrhosis, erectile dysfunction, female sexual disorders, disorders related to diabetes, ocular disorders and other related cardiovascular disorders.

Increased concentration of cGMP leads to vasodilation, inhibition of platelet aggregation and adhesion, anti-hypertensive effects, anti-remodeling effects, anti-apoptotic effects, anti-inflammatory effects and neuronal signal transmission effects. Thus, sGC stimulators may be used to treat and/or prevent a range of diseases and disorders, including but not limited to a peripheral, pulmonary, hepatic, liver, cardiac or cerebrovascular/endothelial disorders or conditions, a urogenital-gynecological or sexual disorder or condition, a thromboembolic disease, an ischemic disease, a fibrotic disorder, a topical or skin disorder, a pulmonary or respiratory disorder, a renal or hepatic disorder, a metabolic disorder, atherosclerosis, or a lipid related disorder.

In other embodiments, the compounds here disclosed are sGC stimulators that may be useful in the prevention and/or treatment of diseases and disorders characterized by undesirable reduced bioavailability of and/or sensitivity to NO, such as those associated with conditions of oxidative stress or nitrosative stress.

In other embodiments, the compounds here disclosed are sGC stimulators that may be useful in the prevention and/or treatment of diseases and disorders characterized by increased neuroinflammation. One embodiment of the invention is a method of decreasing neuroinflammation in a subject in need thereof by administering to the subject any one of the compounds of Formula I, IIA, IIB, II, III, IV, V, VI, I-1, I-2, I-3, I-4, I-5, I-6, I-7, I-8, I-9, I-10, I-11, I-12, I-13, I-14, I-15, I-16, I-17 through I-39, I-41, I-42, I-47, I-48, I-50, I-51, I-53, I-54, I-56 through I-60, I-62 through I-68, I-70, I-7, and I-72 or a pharmaceutically acceptable salt thereof. In particular the diseases and disorders is a CNS disease or disorder as described in sections (9)-(16), below.

In other embodiments, the compounds here disclosed are sGC stimulators that may be useful in the prevention and/or treatment of diseases and disorders characterized by increased neurotoxicity. One embodiment of the invention is a method of reducing neurotoxicity in a subject in need thereof by administering to the subject any one of the compounds of Formula I, IIA, IIB, II, III, IV, V, VI, I-1, I-2, I-3, I-4, I-5, I-6, I-7, I-8, I-9, I-10, I-11, I-12, I-13, I-14, I-15, I-16, I-17 through I-39, I-41, I-42, I-47, I-48, I-50, I-51, I-53, I-54, I-56 through I-60, I-62 through I-68, I-70, I-7, and I-72, or a pharmaceutically acceptable salt thereof. In particular the diseases and disorders is a CNS disease or disorder as described in sections (9)-(16), below.

In other embodiments, the compounds here disclosed are sGC stimulators that may be useful in the prevention and/or treatment of diseases and disorders characterized by impaired neurorengeration. One embodiment of the invention is a method of restoring neuroregeneration in a subject in need thereof by administering to the subject any one of the compounds of Formula I, IIA, IIB, II, III, IV, V, VI, I-1, I-2, I-3, I-4, I-5, I-6, I-7, I-8, I-9, I-10, I-11, I-12, I-13, I-14, I-15, or I I-16, I-17 through I-39, I-41, I-42, I-47, I-48, I-50, I-51, I-53, I-54, I-56 through I-60, I-62 through I-68, I-70, I-7, and I-72, or a pharmaceutically acceptable salt thereof. In particular the diseases and disorders is a CNS disease or disorder as described in sections (9)-(16), below.

In other embodiments, the compounds here disclosed are sGC stimulators that may be useful in the prevention and/or treatment of diseases and disorders characterized by impaired synaptic function. One embodiment of the invention is a method of restoring synaptic function in a subject in need thereof by administering to the subject any one of the compounds of Formula I, IIA, IIB, II, III, IV, V, VI, I-1, I-2, I-3, I-4, I-5, I-6, I-7, I-8, I-9, I-10, I-11, I-12, I-13, I-14, I-15, or I-16, I-17 through I-39, I-41, I-42, I-47, I-48, I-50, I-51, I-53, I-54, I-56 through I-60, I-62 through I-68, I-70, I-7, and I-72, or a pharmaceutically acceptable salt thereof. In particular the diseases and disorders is a CNS disease or disorder as described in sections (9)-(16), below.

In other embodiments, the compounds here disclosed are sGC stimulators that may be useful in the prevention and/or treatment of diseases and disorders characterized by down-regulated neurotransmitters. One embodiment of the invention is a method of normalizing neurotransmitter in a subject in need thereof by administering to the subject any one of the compounds of Formula I, IIA, IIB, II, III, IV, V, VI, I-1, I-2, I-3, I-4, I-5, I-6, I-7, I-8, I-9, I-10, I-11, I-12, I-13, I-14, I-15, or I-16, I-17 through I-39, I-41, I-42, I-47, I-48, I-50, I-51, I-53, I-54, I-56 through I-60, I-62 through I-68, I-70, I-7, and I-72, or a pharmaceutically acceptable salt thereof. In particular the diseases and disorders is a CNS disease or disorder as described in sections (9)-(16), below. Specifically, the disease is Alzheimer's Disease. Specifically, the disease is Mixed Dementia.

In other embodiments, the compounds here disclosed are sGC stimulators that may be useful in the prevention and/or treatment of diseases and disorders characterized by impaired cerebral blood flow. One embodiment of the invention is a method of restoring cerebral blood flow in a subject in need thereof by administering to the subject any one of the compounds of Formula I, IIA, IIB, II, III, IV, V, VI, I-1, I-2, I-3, I-4, I-5, I-6, I-7, I-8, I-9, I-10, I-11, I-12, I-13, I-14, I-15, or I-16, I-17 through I-39, I-41, I-42, I-47, I-48, I-50, I-51, I-53, I-54, I-56 through I-60, I-62 through I-68, I-70, I-7, and I-72, or a pharmaceutically acceptable salt thereof. In particular the diseases and disorders is a CNS disease or disorder as described in sections (9)-(16), below. Specifically, the disease is Vascular Dementia or Alzheimer's Disease. Specifically, the disease is Mixed Dementia. In other embodiments CNS disorder is selected from either traumatic (closed or open, penetrating head injuries), traumatic brain injury (TBI), or nontraumatic (stroke, aneurism, hypoxia) injury to the brain or cognitive impairment or dysfunction resulting from brain injuries or neurodegenerative disorders.

In other embodiments, the compounds here disclosed are sGC stimulators that may be useful in the prevention and/or treatment of diseases and disorders characterized by increased neurodegeneration. One embodiment of the invention is a method of decreasing neurodegeneration in a subject in need thereof by administering to the subject any one of the compounds of Formula I, IIA, IIB, II, III, IV, V, VI, I-1, I-2, I-3, I-4, I-5, I-6, I-7, I-8, I-9, I-10, I-11, I-12, I-13, I-14, I-15, or I-16, I-17 through I-39, I-41, I-42, I-47, I-48, I-50, I-51, I-53, I-54, I-56 through I-60, I-62 through I-68, I-70, I-7, and I-72, or a pharmaceutically acceptable salt thereof. In particular the diseases and disorders is a CNS disease or disorder as described in sections (9)-(16), below.

In other embodiments, the compounds here disclosed are sGC stimulators are neuroprotective. In particular, the compounds of Formula I, IIA, IIB, II, III, IV, V, VI, I-1, I-2, I-3, I-4, I-5, I-6, I-7, I-8, I-9, I-10, I-11, I-12, I-13, I-14, I-15, or I-16, I-17 through I-39, I-41, I-42, I-47, I-48, I-50, I-51, I-53, I-54, I-56 through I-60, I-62 through I-68, I-70, I-7, and I-72, or a pharmaceutically acceptable salt thereof may be useful protect the neurons in a subject in need thereof. In particular, the diseases and disorders is a CNS disease or disorder as described in sections (9)-(16), below.

In other embodiments, the compounds here disclosed are sGC stimulators that may be useful in the prevention and/or treatment orphan pain indications. One embodiment of the invention is a method of treating an orphan pain indication in a subject in need thereof by administering to the subject any one of the compounds of Formula I, IIA, IIB, II, III, IV, V, VI, I-1, I-2, I-3, I-4, I-5, I-6, I-7, I-8, I-9, I-10, I-11, I-12, I-13, I-14, I-15, or I-16, I-17 through I-39, I-41, I-42, I-47, I-48, I-50, I-51, I-53, I-54, I-56 through I-60, I-62 through I-68, I-70, I-7, and I-72, or a pharmaceutically acceptable salt thereof. In particular, the orphan pain indication is selected from Acetazolamide-responsive myotonia, Autoerythrocyte sensitization syndrome, Autosomal dominant Charcot-Marie-Tooth disease type 2V, Autosomal dominant intermediate Charcot-Marie-Tooth disease with neuropathic pain, Autosomal recessive limb-girdle muscular dystrophy type 2A, Channelopathy-associated congenital insensitivity to pain, Chronic pain requiring intraspinal analgesia, Complex regional pain syndrome, Complex regional pain syndrome type 1, Complex regional pain syndrome type 2, Congenital insensitivity to pain with hyperhidrosis, Congenital insensitivity to pain with severe intellectual disability, Congenital insensitivity to pain-hypohidrosis syndrome, Diffuse palmoplantar keratoderma with painful fissures, Familial episodic pain syndrome, Familial episodic pain syndrome with predominantly lower limb involvement, Familial episodic pain syndrome with predominantly upper body involvement, Hereditary painful callosities, Hereditary sensory and autonomic neuropathy type 4, Hereditary sensory and autonomic neuropathy type 5, Hereditary sensory and autonomic neuropathy type 7, Interstitial cystitis, Painful orbital and systemic neurofibromas-marfanoid habitus syndrome, Paroxysmal extreme pain disorder, Persistent idiopathic facial pain, Qualitative or quantitative defects of calpain, and Tolosa-Hunt syndrome.

Throughout this disclosure, the terms "hypertension", "arterial hypertension" or "high blood pressure (HBP)" are used interchangeable and refer to an extremely common and highly preventable chronic condition in which blood pressure (BP) in the arteries is higher than normal. If not properly controlled, it represents a significant risk factor for several serious cardiovascular and renal conditions. Hypertension may be a primary disease, called "essential hypertension" or "idiopathic hypertension", or it may be caused by other diseases, in which case it is classified as "secondary hypertension". Essential hypertension accounts for 90-95% of all cases.

As used herein, the term "resistant hypertension" refers to hypertension that remains above goal blood pressure (usually less than 140/90 mmHg, although a lower goal of less than 130/80 mmHg is recommended for patients with comorbid diabetes or kidney disease), in spite of concurrent use of three antihypertensive agents belonging to different antihypertensive drug classes. People who require four or more drugs to control their blood pressure are also considered to have resistant hypertension. Hypertension is an extremely common comorbid condition in diabetes, affecting ~20-60% of patients with diabetes, depending on obesity, ethnicity, and age. This type of hypertension is herein referred to as "diabetic hypertension". In type 2 diabetes, hypertension is often present as part of the metabolic syndrome of insulin resistance also including central obesity and dyslipidemia. In type 1 diabetes, hypertension may reflect the onset of diabetic nephropathy.

"Pulmonary hypertension (PH)", as used herein, is a disease characterized by sustained elevations of blood pressure in the pulmonary vasculature (pulmonary artery, pulmonary vein and pulmonary capillaries), which results in right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxaemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

As used herein "heart failure" is a progressive disorder of left ventricular (LV) myocardial remodeling that culminates in a complex clinical syndrome in which impaired cardiac function and circulatory congestion are the defining features, and results in insufficient delivery of blood and nutrients to body tissues. The condition occurs when the heart is damaged or overworked and unable to pump out all the blood that returns to it from the systemic circulation. As less blood is pumped out, blood returning to the heart backs up and fluid builds up in other parts of the body. Heart failure also impairs the kidneys' ability to dispose of sodium and water, complicating fluid retention further. Heart failure is characterized by autonomic dysfunction, neurohormonal activation and overproduction of cytokines, which contribute to progressive circulatory failure. Symptoms of heart failure include: dyspnea (shortness of breath) while exercising or resting and waking at night due to sudden breathlessness, both indicative of pulmonary edema; general fatigue or weakness, edema of the feet, ankles and legs, rapid weight gain, chronic cough, including that producing mucus or blood. Depending on its clinical presentation, heart failure is classified as de novo, transient or chronic. Acute heart failure, i.e. the rapid or gradual onset of symptoms requiring urgent therapy, may develop de novo or as a result of chronic heart failure becoming decompensated. Diabetes is a common comorbidity in patients with heart failure and is associated with poorer outcomes as well as potentially compromising the efficacy of treatments. Other important comorbidities include systemic hypertension, chronic airflow obstruction, sleep apnea, cognitive dysfunction, anemia, chronic kidney disease and arthritis. Chronic left heart failure is frequently associated with the development of pulmonary hypertension. The frequency of certain comorbidities varies by gender: among women, hypertension and thyroid disease are more common, while men more commonly suffer from chronic obstructive pulmonary disease (COPD), peripheral vascular disease, coronary artery disease and renal insufficiency. Depression is a frequent comorbidity of heart failure and the two conditions can and often do complicate one another. Cachexia has long been recognized as a serious and frequent complication of heart failure, affecting up to 15% of all heart failure patients and being associated with poor prognosis. Cardiac cachexia is defined as the nonedematous, nonvoluntary loss of at least 6% of body weight over a period of six months.

The term "sleep apnea" refers to the most common of the sleep-disordered breathing disorders. It is a condition characterized by intermittent, cyclical reductions or total cessations of airflow, which may or may not involve obstruction of the upper airway. There are three types of sleep apnea: obstructive sleep apnea, the most common form, central sleep apnea and mixed sleep apnea.

"Central sleep apnea (CSA)", is caused by a malfunction in the brain's normal signal to breathe, rather than physical blockage of the airway. The lack of respiratory effort leads to an increase in carbon dioxide in the blood, which may rouse the patient. CSA is rare in the general population, but is a relatively common occurrence in patients with systolic heart failure.

As used herein, the term "metabolic syndrome", "insulin resistance syndrome" or "syndrome X", refers to a group or clustering of metabolic conditions (abdominal obesity, elevated fasting glucose, "dyslipidemia" (i.e., elevated lipid levels) and elevated blood pressure (HBP)) which occur together more often than by chance alone and that together promote the development of type 2 diabetes and cardiovascular disease. Metabolic syndrome is characterized by a specific lipid profile of increased triglycerides, decreased high-density lipoprotein cholesterol (HDL-cholesterol) and in some cases moderately elevated low-density lipoprotein cholesterol (LDL-cholesterol) levels, as well as accelerated progression of "atherosclerotic disease" due to the pressure of the component risk factors. There are several types of dyslipidemias: "hypercholesterolemia" refers to elevated levels of cholesterol. Familial hypercholesterolemia is a specific form of hypercholesterolemia due to a defect on chromosome 19 (19p13.1-13.3). "Hyperglyceridemia" refers to elevated levels of glycerides (e.g., "hypertrigliceridemia" involves elevated levels of triglycerides). "Hyperlipoproteinemia" refers to elevated levels of lipoproteins (usually LDL unless otherwise specified).

As used herein, the term "peripheral vascular disease (PVD)", also commonly referred to as "peripheral arterial disease (PAD)" or "peripheral artery occlusive disease (PAOD)", refers to the obstruction of large arteries not within the coronary, aortic arch vasculature, or brain. PVD can result from atherosclerosis, inflammatory processes leading to stenosis, an embolism, or thrombus formation. It causes either acute or chronic "ischemia (lack of blood supply)". Often PVD is a term used to refer to atherosclerotic blockages found in the lower extremity. PVD also includes a subset of diseases classified as microvascular diseases resulting from episodal narrowing of the arteries (e.g., "Raynaud's phenomenon"), or widening thereof (erythromelalgia), i.e. vascular spasms.

The term "thrombosis" refers to the formation of a blood clot ("thrombus") inside a blood vessel, obstructing the flow of blood through the circulatory system. When a blood vessel is injured, the body uses platelets (thrombocytes) and fibrin to form a blood clot to prevent blood loss. Alternatively, even when a blood vessel is not injured, blood clots may form in the body if the proper conditions present themselves. If the clotting is too severe and the clot breaks free, the traveling clot is now known as an "embolus". The term "thromboembolism" refers to the combination of thrombosis and its main complication, "embolism". When a thrombus occupies more than 75% of surface area of the lumen of an artery, blood flow to the tissue supplied is reduced enough to cause symptoms because of decreased oxygen (hypoxia) and accumulation of metabolic products like lactic acid ("gout"). More than 90% obstruction can result in anoxia, the complete deprivation of oxygen, and "infarction", a mode of cell death.

An "embolism" (plural embolisms) is the event of lodging of an embolus (a detached intravascular mass capable of clogging arterial capillary beds at a site far from its origin) into a narrow capillary vessel of an arterial bed which causes a blockage (vascular occlusion) in a distant part of the body. This is not to be confused with a thrombus which blocks at the site of origin.

A "stroke", or cerebrovascular accident (CVA), is the rapid loss of brain function(s) due to disturbance in the blood supply to the brain. This can be due to "ischemia" (lack of blood flow) caused by blockage (thrombosis, arterial embolism), or a hemorrhage (leakage of blood). As a result, the affected area of the brain cannot function, which might result in an inability to move one or more limbs on one side of the body, inability to understand or formulate speech, or an inability to see one side of the visual field. Risk factors for stroke include old age, hypertension, previous stroke or transient ischemic attack (TIA), diabetes, high cholesterol, cigarette smoking and atrial fibrillation. High blood pressure is the most important modifiable risk factor of stroke. An "ischemic stroke" is occasionally treated in a hospital with thrombolysis (also known as a "clot buster"), and some hemorrhagic strokes benefit from neurosurgery. Prevention of recurrence may involve the administration of antiplatelet drugs such as aspirin and dipyridamole, control and reduction of hypertension, and the use of statins. Selected patients may benefit from carotid endarterectomy and the use of anticoagulants.

"Ischemia" is a restriction in blood supply to tissues, causing a shortage of oxygen and glucose needed for cellular metabolism (to keep tissue alive). Ischemia is generally caused by problems with blood vessels, with resultant damage to or dysfunction of tissue. It also means local anemia in a given part of a body sometimes resulting from congestion (such as vasoconstriction, thrombosis or embolism).

According to the American Psychiatric Association's Diagnostic and Statistical Manual of Mental Disorders, Fourth Edition (DSM-IV), the term "sexual dysfunction" encompasses a series of conditions "characterized by disturbances in sexual desire and in the psychophysiological changes associated with the sexual response cycle"; while problems of this type are common, sexual dysfunction is only considered to exist when the problems cause distress for the patient. Sexual dysfunction can be either physical or psychological in origin. It can exist as a primary condition, generally hormonal in nature, although most often it is secondary to other medical conditions or to drug therapy for said conditions. All types of sexual dysfunction can be further classified as life-long, acquired, situational or generalized (or combinations thereof).

The DSM-IV-TR specifies five major categories of "female sexual dysfunction": sexual desire/interest disorders; "sexual arousal disorders (including genital, subjective and combined)"; orgasmic disorder; dyspareunia and vaginismus; and persistent sexual arousal disorder.

"Female sexual arousal disorder (FSAD)" is defined as a persistent or recurring inability to attain or maintain sufficient levels of sexual excitement, causing personal distress. FSAD encompasses both the lack of subjective feelings of excitement (i.e., subjective sexual arousal disorder) and the lack of somatic responses such as lubrication and swelling (i.e., genital/physical sexual arousal disorder). FSAD may be strictly psychological in origin, although it generally is caused or complicated by medical or physiological factors. Hypoestrogenism is the most common physiologic condition associated with FSAD, which leads to urogenital atrophy and a decrease in vaginal lubrication.

As used herein, "erectile dysfunction (ED)" is a male sexual dysfunction characterized by the inability to develop or maintain an erection of the penis during sexual performance. A penile erection is the hydraulic effect of blood entering and being retained in sponge-like bodies within the penis. The process is often initiated as a result of sexual arousal, when signals are transmitted from the brain to nerves in the penis. Erectile dysfunction is indicated when an erection is difficult to produce. The most important organic causes are cardiovascular disease and diabetes, neurological problems (for example, trauma from prostatectomy surgery), hormonal insufficiencies (hypogonadism) and drug side effects.

As used herein, the term "bronchoconstriction" is used to define the constriction of the airways in the lungs due to the tightening of surrounding smooth muscle, with consequent coughing, wheezing, and shortness of breath. The condition has a number of causes, the most common being as well as asthma. Exercise and allergies can bring on the symptoms in an otherwise asymptomatic individual. Other conditions such as chronic obstructive pulmonary disease (COPD) can also present with bronchoconstriction.

Specific diseases of disorders which may be treated and/or prevented by administering an sGC stimulator of the invention, include but are not limited to: hypertension (e.g., diabetic hypertension, arterial hypertension, pulmonary hypertension, resistant hypertension, peripheral artery disease, etc.), heart failure (e.g., left ventricular diastolic dysfunction (LVDD) and left ventricular systolic dysfunction (LVSD), sleep apnea associated with heart failure), arteriosclerotic disease (e.g., atherosclerosis), thromboembolic disorders (e.g., chronic thromboembolic pulmonary hypertension, thrombosis, stroke (in particular, ischemic stroke), embolism, pulmonary embolism), Alzheimer's disease, renal diseases (e.g., renal fibrosis, ischemic renal disease, renal failure, renal insufficiency, chronic kidney disease), hepatic disease (e.g., liver fibrosis or cirrhosis), respiratory disease (e.g., pulmonary fibrosis, asthma, chronic obstructive pulmonary disease, interstitial lung disease), sexual disorders (e.g., erectile dysfunction, male and female sexual dysfunction, vaginal atrophy), sickle cell anemia, neuro inflammatory diseases or disorders and metabolic disorders (e.g., lipid related disorders).

Further specific diseases of disorders which may be treated and/or prevented by administering an sGC stimulator of the invention, include but are not limited to: age-associated memory impairment, mixed dementia, sleep wake disorders, and Sneddon's syndrome.

Further specific diseases of disorders which may be treated and/or prevented by administering an sGC stimulator of the invention, include but are not limited to: acute pain, central pain syndrome, chemotherapy induced neuropathy and neuropathic pain, diabetic neuropathy, fibromyalgia, inflammatory pain, neuropathic pain, neuropathic pain associated with a CNS disease, painful diabetic peripheral neuropathy, post-operative pain, tonic pain, and visceral pain.

Further specific diseases of disorders which may be treated and/or prevented by administering an sGC stimulator of the invention, include but are not limited to: altitude (mountain) sickness, cerebral small vessel disease, cerebral vasculitis, cerebral vasospasm, diabetic heart failure (diabetic HF), diabetic angiopathy, diabetic macular edema, diabetic microangiopathies, Heart failure with preserved ejection fraction (HFpEF), hepatic encephalopathy, moyamoya, non-diabetic nephropathy, and Parkinson's Dysphagia.

Further specific diseases of disorders which may be treated and/or prevented by administering an sGC stimulator of the invention, include but are not limited to: angina, ataxia telangliectasia, autism spectrum disorder, chronic fatigue, chronic traumatic encephalopathy (CTE), cognitive impairment associated with diabetes, cognitive impairment associated with Multiple Sclerosis, cognitive impairment associated with obstructive sleep apnea, cognitive impairment associated with schizophrenia (CIAS), cognitive impairment associated with sickle cell, concussion, dysphagia, eye fibrosis, Fabry Disease, Gaucher Disease, glioblastoma, inflammation caused by cerebral malaria (SoC), inflammation caused by infectious disease, intellectual disability, microvascular angina, myopic choroidal neovascularization, neuromyelitis optica, neuropathic pain with Multiple Sclerosis, neuropathic pain with shingles (herpes zoster), neuropathic pain with spine surgery, Parkinson's Dementia, peripheral and autonomic neuropathies, peripheral retinal degeneration, post-traumatic stress syndrome, post herpetic neuralgia, post-operative dementia, proliferative vitroretinopathy, radiation induced fibrosis, radiculopathy, refractory epilepsy, retinal vein occlusion, Sjogren's syndrome, spinal cord injury, spinal muscular atrophy, spinal subluxations, tauopathies, ulcers, and wet age-related macular degeneration.

The compounds of Formula I as well as pharmaceutically acceptable salts thereof, as stimulators of sGC, are useful in the prevention and/or treatment of the following types of diseases, conditions and disorders which can benefit from sGC stimulation or an upregulation of the NO pathway:

(1) Peripheral, pulmonary, hepatic, kidney, cardiac or cerebral vascular/endothelial disorders/conditions or diseases otherwise related to circulation:

disorders related to high blood pressure and decreased coronary blood flow such as increased acute and chronic coronary blood pressure, arterial hypertension and vascular disorder resulting from cardiac and renal complications (e.g. heart disease, stroke, cerebral ischemia, renal failure); resistant hypertension, diabetic hypertension, congestive heart failure; diastolic or systolic dysfunction; coronary insufficiency; arrhythmias; reduction of ventricular preload; cardiac hypertrophy; heart failure/cardiorenal syndrome; portal hypertension; endothelial dysfunction or injury;

thromboembolic disorders and ischemias such as myocardial infarction, stroke (in particular, ischemic stroke), transient ischemic attacks (TIAs); obstructive thromboanginitis; stable or unstable angina pectoris; coronary spasms, variant angina, Prinzmetal's angina; prevention of restenosis after thrombolysis therapies; thrombogenic disorders;

peripheral arterial disease, peripheral occlusive arterial disease; peripheral vascular disease; hypertonia; Raynaud's syndrome or phenomenon, critical limb ischemia, vasculitis; peripheral embolism; intermittent claudication; vaso-occlusive crisis; Duchenne and Becker muscular dystrophies; microcirculation abnormalities; control of vascular leakage or permeability;

shock; sepsis; cardiogenic shock; control of leukocyte activation; inhibition or modulation of platelet aggregation;

pulmonary/respiratory conditions such as pulmonary hypertension, pulmonary arterial hypertension, and associated pulmonary vascular remodeling (e.g. localized thrombosis and right heart hypertrophy); pulmonary hypertonia; primary pulmonary hypertension, secondary pulmonary hypertension, familial pulmonary hypertension, sporadic pulmonary hypertension, precapillary pulmonary hypertension, idiopathic pulmonary hypertension, thrombotic pulmonary arteriopathy, plexogenic pulmonary arteriopathy; cystic fibrosis; bronchoconstriction or pulmonary bronchoconstriction; acute respiratory distress syndrome; lung fibrosis, lung transplant;

pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary venoocclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, other coagulation disorders, chronic thromboembolism, pulmonary embolism (due to tumor, parasites or foreign material), connective tissue disease, lupus, schistosomiasis, sarcoidosis, chronic obstructive pulmonary disease, asthma, emphysema, chronic bronchitis, pulmonary capillary hemangiomatosis; histiocytosis X, lymphangiomatosis and compressed pulmonary vessels (such as due to adenopathy, tumor or fibrosing mediastinitis);

arterosclerotic diseases or conditions such as atherosclerosis (e.g., associated with endothelial injury, platelet and monocyte adhesion and aggregation, smooth muscle proliferation and migration); restenosis (e.g., developed after thrombolysis therapies, percutaneous transluminal angioplasties (PTAs), percutaneous transluminal coronary angioplasties (PTCAs) and bypass); inflammation;

cardiovascular disease associated with metabolic syndrome (e.g., obesity, dyslipidemia, diabetes, high blood pressure); lipid related disorders such as dyslipidemia, hypercholesterolemia, hypertriglyceridemia, sitosterolemia, fatty liver disease, and hepatitis; preeclampsia; polycystic kidney disease progression; subcutaneous fat; obesity;

liver cirrhosis, associated with chronic liver disease, hepatic fibrosis, hepatic stellate cell activation, hepatic fibrous collagen and total collagen accumulation; liver disease of necro-inflammatory and/or of immunological origin; and urogenital system disorders, such as renal fibrosis and renal failure resulting from chronic kidney diseases or insufficiency (e.g. due to accumulation/deposition and tissue injury, progressive sclerosis, glomerulonephritis); prostate hypertrophy systemic sclerosis; cardiac interstitial fibrosis; cardiac remodeling and fibrosis; cardiac hypertrophy; non-alcoholic steatohepatitis or NASH;

(2) ischemia, reperfusion damage; ischemia/reperfusion associated with organ transplant, lung transplant, pulmonary transplant, cardiac transplant; conserving blood substituents in trauma patients;

(3) sexual, gynecological and urological disorders of conditions: erectile dysfunction; impotence; premature ejaculation; female sexual dysfunction (e.g., female sexual arousal dysfunction, hypoactive sexual arousal disorder), vaginal atrophy, dyspaneuria, atrophic vaginitis; benign prostatic hyperplasia (BPH) or hypertrophy or enlargement, bladder outlet obstruction; bladder pain syndrome (BPS), interstitial cystitis (IC), overactive bladder, neurogenic bladder and incontinence; diabetic nephropathy;

(4) ocular diseases or disorders: glaucoma, retinopathy, diabetic retinopathy (including proliferative and non-proliferative), blepharitis, dry eye syndrome, Sjögren's Syndrome;

(5) hearing diseases or disorders: hearing impairment, partial or total hearing loss; partial or total deafness; tinnitus; noise-induced hearing loss;

(6) topical or skin disorders or conditions: dermal fibrosis, scleroderma, skin fibrosis;

(7) wound healing: for instance in diabetics; microvascular perfusion improvement (e.g., following injury, to counteract the inflammatory response in perioperative care), anal fissures, diabetic ulcers;

(8) other diseases or conditions: cancer metastasis, osteoporosis, gastroparesis; functional dyspepsia; diabetic complications, diseases associated with endothelial dysfunction, and neurologic disorders associated with decreased nitric oxide production; achalasia or esophageal achalasia.

(9) a CNS disease, health condition or disorder selected from Alzheimer's disease, amyotrophic lateral sclerosis (ALS or Lou Gehrig's disease), Down syndrome, dementia, vascular dementia, vascular cognitive impairment, Mixed Dementia, Binswanger's dementia (subcortical arteriosclerotic encephalopathy), Cerebral Autosomal-Dominant Arteriopathy with Subcortical Infarcts and Leukoencephalopathy (CADASIL or CADASIL syndrome), frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia (mild cognitive impairment, MCI), glaucoma, Huntington's diseases (or chorea, HD), or a cognitive defect associated with HD; multiple sclerosis (MS) (including Clinically isolated syndrome (CIS), Relapsing-remitting MS (RRMS), Primary progressive MS (PPMS), and Secondary progressive MS (SPMS),) multiple system atrophy (MSA), Parkinson's disease, Parkinsonism Plus, spinocerebellar ataxias, Steel-Richardson-Olszewski disease (progressive supranuclear palsy), attention deficit disorder (ADD) and attention deficit hyperactivity disorder (ADHD);

(10) a CNS disorder or condition selected from Alzheimer's disease or pre-Alzheimer's disease, mild to moderate Alzheimer's disease or moderate to severe Alzheimer's disease;

(11) a CNS disorder is selected from either traumatic (closed or open, penetrating head injuries), traumatic brain injury (TBI, including, for example, concussions and Chronic traumatic encephalopathy (CTE)), or nontraumatic (stroke (including ischemic stroke), aneurism, hypoxia) injury to the brain or cognitive impairment or dysfunction resulting from brain injuries or neurodegenerative disorders;

(12) a CNS disease or disorder is selected from dystonias, including for example, generalized, focal, segmental, sexual, intermediate, acute dystonic reaction, and genetic/primary dystonia; and dyskinesias, including for example, acute, chronic/tardive, and non-motor and levo-dopa induced dyskinesia (LID);

(13) a CNS disease or disorder is selected from disorders characterized by a relative reduction in synaptic plasticity and synaptic processes including, for example, Fragile X, Rhett's disorder, Williams syndrome, Renpenning's syndrome, autism spectrum disorders, including autism, Asperger's syndrome, pervasive development disorder and childhood disintegrative disorder;

(14) a CNS disorder is neuropathic pain;

(15) a CNS disorder is a psychiatric, mental, mood or affective disorder selected from a bipolar disorder, schizophrenia, general psychosis, drug-induced psychosis, a delusional disorder, schizoaffective disorder, obsessive compulsive disorder (OCD), a depressive disorder, an anxiety disorder, a panic disorder, post-traumatic stress disorder (PTSD); or

(16) a CNS disorder is selected from chemo brain, levo-dopa induced addictive behavior, alcoholism, narcotic dependence (including but not limited to amphetamine, opiates or other substances) and substance abuse.

In other embodiments of the invention, the compounds of Formula I as well as pharmaceutically acceptable salts thereof are useful in the prevention and/or treatment of the following types of diseases, conditions and disorders which can benefit from sGC stimulation or an upregulation of the NO pathway:

hypertension, resistant hypertension, diabetic hypertension, pulmonary hypertension (PH), pulmonary arterial hypertension, PH associated with COPD, chronic airflow obstruction, asthma or pulmonary fibrosis, thrombosis, embolism, thromboembolic disorders, Alzheimer's disease, atherosclerosis, right heart hypertrophy, heart failure, diastolic dysfunction, systolic dysfunction, sleep apnea associated with heart failure, liver cirrhosis, renal fibrosis, renal failure resulting from chronic kidney diseases or insufficiency, metabolic disorder, dyslipidemia, hypercholesterolemia, hypertriglyceridemia, sitosterolemia, fatty liver disease, hepatitis, erectile dysfunction, female sexual dysfunction, female sexual arousal dysfunction and vaginal atrophy.

In some embodiments, the invention relates to a method of treating a disease, health condition or disorder in a subject, comprising administering a therapeutically effective amount of a compound of any of the above depicted Formulae, or a pharmaceutically acceptable salt thereof, to the subject in need of treatment, wherein the disease, health condition or disorder is selected from one of the diseases listed above.

In other embodiments the disease, health condition or disorder is selected from a peripheral, pulmonary, hepatic, kidney, cardiac or cerebralvascular/endothelial disorder or condition, or a disease otherwise related to circulation selected from: increased acute and chronic coronary blood pressure, arterial hypertension and vascular disorder resulting from cardiac and renal complications, heart disease, stroke (in particular, ischemic stroke), cerebral ischemia, renal failure; resistant hypertension, diabetic hypertension, congestive heart failure; diastolic or systolic dysfunction; coronary insufficiency; arrhythmias; reduction of ventricular preload; cardiac hypertrophy; heart failure/cardiorenal syndrome; portal hypertension; endothelial dysfunction or injury; myocardial infarction; stroke or transient ischemic attacks (TIAs); obstructive thromboanginitis; stable or unstable angina pectoris; coronary spasms, variant angina, Prinzmetal's angina; restenosis as a result of thrombolysis therapies and thrombogenic disorders.

In still other embodiments, the disease, health condition or disorder is selected from a peripheral vascular/endothelial disorder or condition or a disease otherwise related to circulation selected from: peripheral arterial disease, peripheral occlusive arterial disease; peripheral vascular disease; hypertonias; Raynaud's syndrome or phenomenon or disease; critical limb ischemia; vasculitis; peripheral embolism; intermittent claudication; vaso-occlusive crisis; Duchenne and Becker muscular dystrophies; microcirculation abnormalities; and vascular leakage or permeability issues.

In further embodiments, the disease, health condition or disorder is a pulmonary disorder or condition or a disease otherwise related to circulation selected from: pulmonary hypertension; pulmonary arterial hypertension and associated pulmonary vascular remodeling; localized thrombosis; right heart hypertrophy; pulmonary hypertonia; primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy; cystic fibrosis; bronchoconstriction or pulmonary bronchoconstriction; acute respiratory distress syndrome; lung fibrosis and lung transplant. In some of these embodiments, the pulmonary hypertension is pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary venoocclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, coagulation disorders, chronic thromboembolism; pulmonary embolism, due to tumor, parasites or foreign material; connective tissue disease, lupus, schistosomiasis, sarcoidosis, chronic obstructive pulmonary disease, asthma, emphysema, chronic bronchitis, pulmonary capillary hemangiomatosis; histiocytosis X; lymphangiomatosis and compressed pulmonary vessels due to adenopathy, tumor or fibrosing mediastinitis.

In still other embodiments, the health condition or disorder is a vascular or endothelial disorder or condition or a disease otherwise related to circulation selected from: arterosclerotic diseases; atherosclerosis, atherosclerosis associated with endothelial injury, atherosclerosis associated with platelet and monocyte adhesion and aggregation, atherosclerosis associated with smooth muscle proliferation and migration; restenosis, restenosis developed after thrombolysis therapies; restenosis developed after percutaneous transluminal angioplasties; restenosis developed after percutaneous transluminal coronary angioplasties and bypass; inflammation; cardiovascular disease associated with metabolic syndrome, obesity, dyslipidemia, diabetes or high blood pressure; lipid related disorders, dyslipidemia, hypercholesterolemia, hypertriglyceridemia, sitosterolemia, fatty liver disease, and hepatitis; preeclampsia; polycystic kidney disease progression; and subcutaneous fat.

In yet other embodiments, the disease, health condition or disorder selected from liver cirrhosis, liver cirrhosis associated with chronic liver disease, hepatic fibrosis, hepatic stellate cell activation, hepatic fibrous collagen and total collagen accumulation; and liver disease of necro-inflammatory or of immunological origin.

In further embodiments, the disease, health condition or disorder is a urogenital system disorder selected from renal fibrosis; renal failure resulting from chronic kidney diseases or insufficiency; renal failure due to accumulation or deposition and tissue injury, progressive sclerosis or glomerulonephritis; and prostatic hypertrophy.

In further embodiments, the disease, health condition or disorder is systemic sclerosis.

In further embodiments, the disease, health condition or disorder is a cardiac disorder selected from cardiac interstitial fibrosis; cardiac remodeling and fibrosis and cardiac hypertrophy.

In some embodiments, the disorder is a CNS disease, health condition or disorder selected from Alzheimer's disease, amyotrophic lateral sclerosis (ALS or Lou Gehrig's disease), Down syndrome, dementia, vascular dementia, Mixed Dementia, vascular cognitive impairment, Binswanger's dementia (subcortical arteriosclerotic encephalopathy), Cerebral Autosomal-Dominant Arteriopathy with Subcortical Infarcts and Leukoencephalopathy (CADASIL or CADASIL syndrome), frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia (mild cognitive impairment, MCI), glaucoma, Huntington's diseases (or chorea, HD), or a cognitive defect associated with HD; multiple sclerosis (MS), multiple system atrophy (MSA), Parkinson's disease, Parkinsonism Plus, spinocerebellar ataxias, Steel-Richardson-Olszewski disease (progressive supranuclear palsy), attention deficit disorder (ADD) and attention deficit hyperactivity disorder (ADHD).

In further embodiments, the disease, health condition or disorder is a CNS disorder or condition selected from Alzheimer's disease or pre-Alzheimer's disease, mild to moderate Alzheimer's disease or moderate to severe Alzheimer's disease.

In other embodiments, the CNS disorder is selected from either traumatic (closed or open, penetrating head injuries), traumatic brain injury (TBI), or nontraumatic (stroke (in particular, ischemic stroke), aneurism, hypoxia) injury to the brain or cognitive impairment or dysfunction resulting from brain injuries or neurodegenerative disorders.

In other embodiments, the CNS disease or disorder is selected from dystonias, including for example, generalized, focal, segmental, sexual, intermediate, acute dystonic reaction, and genetic/primary dystonia; and dyskinesias, including for example, acute, chronic/tardive, and non-motor and levo-dopa induced dyskinesia (LID).

In other embodiments, the CNS disease or disorder is selected from disorders characterized by a relative reduction in synaptic plasticity and synaptic processes including, for example, Fragile X, Rhett's disorder, Williams syndrome, Renpenning's syndrome, autism spectrum disorders, including autism, Asperger's syndrome, pervasive development disorder and childhood disintegrative disorder.

In other embodiments, the CNS disorder is neuropathic pain.

In other embodiments, the CNS disorder is a psychiatric, mental, mood or affective disorder selected from a bipolar disorder, schizophrenia, general psychosis, drug-induced psychosis, a delusional disorder, schizoaffective disorder, obsessive compulsive disorder (OCD), a depressive disorder, an anxiety disorder, a panic disorder, post-traumatic stress disorder (PTSD).

In other embodiments, the CNS disorder is selected from chemo brain, levo-dopa induced addictive behavior, alcoholism, narcotic dependence (including but not limited to amphetamine, opiates or other substances) and substance abuse.

In some embodiments, the disease or disorder is achalasia or esophageal achalasia.

In other embodiments, the disease or disorder is non-alcoholic steatohepatitis or NASH.

In further embodiments, the disease, health condition or disorder is selected from ischemia, reperfusion damage; ischemia/reperfusion associated with organ transplant, lung transplant, pulmonary transplant or cardiac transplant; conserving blood substituents in trauma patients.

In further embodiments, the disease, health condition or disorder is a sexual, gynecological or urological disorder of condition selected from erectile dysfunction; impotence; premature ejaculation; female sexual dysfunction; female sexual arousal dysfunction; hypoactive sexual arousal disorder; vaginal atrophy, dyspaneuria, atrophic vaginitis; benign prostatic hyperplasia (BPH) or hypertrophy or enlargement; bladder outlet obstruction; bladder pain syndrome (BPS); interstitial cystitis (IC); overactive bladder, neurogenic bladder and incontinence; diabetic nephropathy.

In further embodiments, the disease, health condition or disorder is selected from vaginal atrophy, dyspaneuria and atrophic vaginitis.

In further embodiments, the disease, health condition or disorder is selected from benign prostatic hyperplasia (BPH) or hypertrophy or enlargement; bladder outlet obstruction; bladder pain syndrome (BPS); interstitial cystitis (IC); overactive bladder, neurogenic bladder and incontinence.

In further embodiments, the disease, health condition or disorder is a sexual, condition selected from erectile dysfunction; impotence; premature ejaculation; female sexual dysfunction; female sexual arousal dysfunction and hypoactive sexual arousal disorder.

In further embodiments, the disease or disorder is diabetic nephropathy.

In further embodiments, the disease, health condition or disorder is Duchenne and Becker muscular dystrophies.

In further embodiments, the disease is an ocular diseases or disorder selected from glaucoma, retinopathy, diabetic retinopathy (including proliferative and non-proliferative), blepharitis, dry eye syndrome and Sjögren's Syndrome.

In further embodiments, the disease is a hearing diseases or disorder selected from hearing impairment, partial or total hearing loss; partial or total deafness; tinnitus; and noise-induced hearing loss.

In further embodiments, the disease is a topical or skin disorders or condition selected from dermal fibrosis, scleroderma and skin fibrosis.

In further embodiments, the treatment involves wound healing; wound healing in diabetics; improvement of microvascular perfusion; improvement of microvascular perfusion issues following injury; treatment of anal fissures; and treatment of diabetic ulcers.

In further embodiments, the disease or condition is selected from cancer metastasis; osteoporosis; gastroparesis; functional dyspepsia; diabetic complications; diseases associated with endothelial dysfunction and neurologic disorders associated with decreased nitric oxide production.

In further embodiments, the disease or condition is selected from age-associated memory impairment, mixed dementia, sleep wake disorders, and Sneddon's syndrome.

In further embodiments, the disease or condition is selected from acute pain, central pain syndrome, chemotherapy induced neuropathy and neuropathic pain, diabetic neuropathy, fibromyalgia, Inflammatory pain, neuropathic pain, neuropathic pain associated with a CNS disease, painful diabetic peripheral neuropathy, post-operative pain, tonic pain, and visceral pain.

In further embodiments, the disease or condition is selected from altitude (mountain) sickness, cerebral small vessel disease, cerebral vasculitis, cerebral vasospasm, diabetic heart failure (diabetic HF), diabetic angiopathy, diabetic macular edema, diabetic microangiopathies, Heart failure with preserved ejection fraction (HFpEF), hepatic encephalopathy, moyamoya, non-diabetic nephropathy, and Parkinson's Dysphagia.

In further embodiments, the disease or condition is selected from angina, ataxia telangliectasia, autism spectrum disorder, chronic fatigue, chronic traumatic encephalopathy (CTE), cognitive impairment associated with diabetes, cognitive impairment associated with Multiple Sclerosis, cognitive impairment associated with obstructive sleep apnea, cognitive impairment associated with schizophrenia (CIAS), cognitive impairment associated with sickle cell, concussion, dysphagia, eye fibrosis, Fabry Disease, Gaucher Disease, glioblastoma, inflammation caused by cerebral malaria (SoC), inflammation caused by infectious disease, intellectual disability, microvascular angina, myopic choroidal neovascularization, neuromyelitis optica, neuropathic pain with Multiple Sclerosis, neuropathic pain with shingles (herpes zoster), neuropathic pain with spine surgery, Parkinson's Dementia, peripheral and autonomic neuropathies, peripheral retinal degeneration, post-traumatic stress syndrome, post herpetic neuralgia, post-operative dementia, proliferative vitroretinopathy, radiation induced fibrosis, radiculopathy, refractory epilepsy, retinal vein occlusion, Sjogren's syndrome, spinal cord injury, spinal muscular atrophy, spinal subluxations, tauopathies, ulcers, and wet age-related macular degeneration.

In further embodiments, the disease or condition is selected from an orphan pain indication. In particular, the orphan pain indication is selected from Acetazolamide-responsive myotonia, Autoerythrocyte sensitization syndrome, Autosomal dominant Charcot-Marie-Tooth disease type 2V, Autosomal dominant intermediate Charcot-Marie-Tooth disease with neuropathic pain, Autosomal recessive limb-girdle muscular dystrophy type 2A, Channelopathy-associated congenital insensitivity to pain, Chronic pain requiring intraspinal analgesia, Complex regional pain syndrome, Complex regional pain syndrome type 1, Complex regional pain syndrome type 2, Congenital insensitivity to pain with hyperhidrosis, Congenital insensitivity to pain with severe intellectual disability, Congenital insensitivity to pain-hypohidrosis syndrome, Diffuse palmoplantar keratoderma with painful fissures, Familial episodic pain syndrome, Familial episodic pain syndrome with predominantly lower limb involvement, Familial episodic pain syndrome with predominantly upper body involvement, Hereditary painful callosities, Hereditary sensory and autonomic neuropathy type 4, Hereditary sensory and autonomic neuropathy type 5, Hereditary sensory and autonomic neuropathy type 7, Interstitial cystitis, Painful orbital and systemic neurofibromas-marfanoid habitus syndrome, Paroxysmal extreme pain disorder, Persistent idiopathic facial pain, Qualitative or quantitative defects of calpain, and Tolosa-Hunt syndrome.

In another embodiment, compounds of the invention can be delivered in the form of implanted devices, such as stents. A stent is a mesh 'tube' inserted into a natural passage/conduit in the body to prevent or counteract a disease-induced, localized flow constriction. The term may also refer to a tube used to temporarily hold such a natural conduit open to allow access for surgery.

A drug-eluting stent (DES) is a peripheral or coronary stent (a scaffold) placed into narrowed, diseased peripheral or coronary arteries that slowly releases a drug to block cell proliferation, usually smooth muscle cell proliferation. This prevents fibrosis that, together with clots (thrombus), could otherwise block the stented artery, a process called restenosis. The stent is usually placed within the peripheral or coronary artery by an Interventional cardiologist or Interventional Radiologist during an angioplasty procedure. Drugs commonly used in DES in order to block cell proliferation include paclitaxel or rapamycin analogues In some embodiments of the invention, a sGC stimulator of the invention can be delivered by means of a drug-eluting stent coated with said sGC stimulator. A drug-eluting stent coated with a sGC stimulator of the invention may be useful in the prevention of stent restenosis and thrombosis during percutaneous coronary interventions. A drug-eluting stent coated with a sGC stimulator of the invention may be able to prevent smooth cell proliferation as well as to assist re-vascularization and re-generation of the endothelial tissue of the artery in which the stent is inserted.

An alternative to percutaneous coronary intervention for the treatment of intractable angina due to coronary artery occlusive disease is the procedure named Coronary Artery Bypass Grafting (CABG). CABG provides only palliation of an ongoing process that is further complicated by the rapid development of graft atherosclerosis. The saphenous vein graft is the most commonly used conduit in CABG surgery. The long-term clinical success of venous CABG is hampered for three main reasons: accelerated graft atherosclerosis, incomplete endothelialization and thrombosis.

In some embodiments, a sGC stimulator of the invention can be used for the prevention of saphenous graft failure during CABG. Compounds of the invention may assist the process of endothelialization and help prevent thrombosis. In this indication, the sGC stimulator is delivered locally in the form of a gel.

The terms, "disease", "disorder" and "condition" may be used interchangeably here to refer to an sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of the above diseases, conditions and disorders in a subject, comprising administering a therapeutically effective amount of a compound of Formula I, or a pharmaceutically acceptable salt thereof, to the subject in need of the treatment. Alternatively, the invention provides the use of a compound of Formula I, or a pharmaceutically acceptable salt thereof, in the treatment of one of these diseases, conditions and disorders in a subject in need of the treatment. The invention further provides a method of making or manufacturing a medicament useful for treating one of these diseases, conditions and disorders comprising using a compound of Formula I, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, cerebrospinal fluid (CSF), or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of an sGC, cGMP and/or NO mediated condition, or the amelioration of one or more symptoms (preferably, one or more discernible symptoms) of said condition (i.e. "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of an sGC, cGMP and/or NO mediated condition. In other embodiments the terms "treat", "treatment" and "treating" refer to the inhibition of the progression of an sGC, cGMP and/or NO mediated condition, either physically by, e.g., stabilization of a discernible symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

In one embodiment, the methods of the invention are a preventative or "pre-emptive" measure to a patient, specifically a human, having a predisposition (e.g. a genetic predisposition) to developing an sGC, cGMP and/or NO related disease, disorder or symptom.

In other embodiments, the methods of the invention are a preventative or "pre-emptive" measure to a patient, specifically a human, suffering from a disease, disorder or condition that makes him at risk of developing an sGC, cGMP or NO related disease, disorder or symptom.

The compounds and pharmaceutical compositions described herein can be used alone or in combination therapy for the treatment or prevention of a disease or disorder mediated, regulated or influenced by sGC, cGMP and/or NO.

Compounds and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula I or a pharmaceutically acceptable salt thereof and a second amount of an additional suitable therapeutic agent.

In one embodiment of this invention, a compound of Formula I, or a pharmaceutically acceptable salt thereof, and the additional therapeutic agent are each administered in an effective amount (i.e., each in an amount which would be therapeutically effective if administered alone). In another embodiment, the compound of Formula I and the additional therapeutic agent are each administered in an amount which alone does not provide a therapeutic effect (a sub-therapeutic dose). In yet another embodiment, the compound of Formula I can be administered in an effective amount, while the additional therapeutic agent is administered in a sub-therapeutic dose. In still another embodiment, the compound of Formula I can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of a compound of Formula I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of Formula I, or a pharmaceutically acceptable salt thereof, either administered separately or in the same pharmaceutical composition include, but are not limited to:

(1) Endothelium-derived releasing factor (EDRF) or NO gas.

(2) NO donors such as a nitrosothiol, a nitrite, a sydnonimine, a NONOate, a N-nitrosamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; isosorbide (Dilatrate®-SR, Imdur®, Ismo®, Isordil®, Isordil®, Titradose®, Monoket®), 3-morpholinosydnonimine; linsidomine chlorohydrate ("SIN-1"); S-nitroso-N-acetylpenicillamine ("SNAP"); S-nitrosoglutathione (GSNO), sodium nitroprusside, S-nitrosoglutathione mono-ethyl-ester (GSNO-ester), 6-(2-hydroxy-1-methyl-nitrosohydrazino)-N-methyl-1-hexanamine or diethylamine NONOate.

(3) Other substances that enhance cGMP concentrations such as protoporphyrin IX, arachidonic acid and phenyl hydrazine derivatives.

(4) Nitric Oxide Synthase substrates: for example, N-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine.

(5) Compounds which enhance eNOS transcription.

(6) NO independent heme-independent sGC activators, including, but not limited to:

BAY 58-2667 (described in patent publication DE19943635)

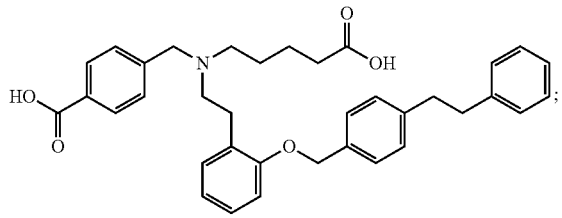 [SMILES: O=C(O)CCCCN(CCc1ccccc1OCc1ccc(CCc2ccccc2)cc1)Cc1ccc(C(=O)O)cc1]

HMR-1766 (ataciguat sodium, described in patent publication WO2000002851)

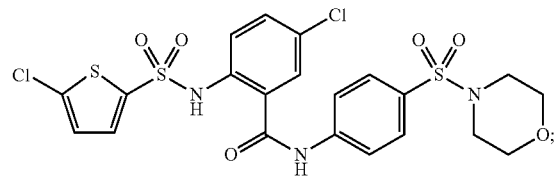 [SMILES: O=C(Nc1ccc(S(=O)(=O)N2CCOCC2)cc1)c1cc(Cl)ccc1NS(=O)(=O)c1ccc(Cl)s1]

S 3448 (2-(4-chloro-phenylsulfonylamino)-4,5-dimethoxy-N-(4-(thiomorpholine-4-sulfonyl)-phenyl)-benzamide (described in patent publications DE19830430 and WO2000002851)

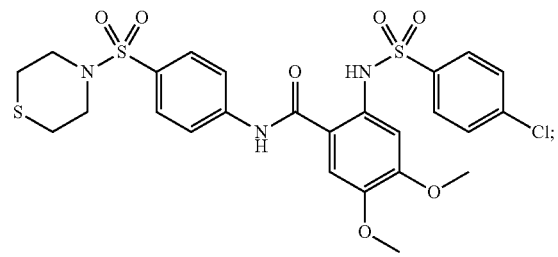 [SMILES: COc1cc(NS(=O)(=O)c2ccc(Cl)cc2)c(C(=O)Nc2ccc(S(=O)(=O)N3CCSCC3)cc2)cc1OC]

and

HMR-1069 (Sanofi-Aventis).

(7) Heme-dependent, NO-independent sGC stimulators including, but not limited to:

YC-1 (see patent publications EP667345 and DE19744026)
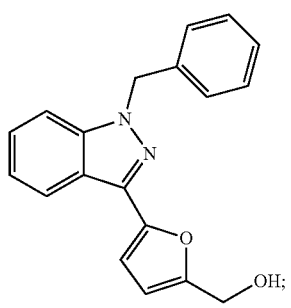 [SMILES: OCc1ccc(-c2nn(Cc3ccccc3)c3ccccc23)o1]
riociguat (BAY 63-2521, Adempas®, described in DE19834044)
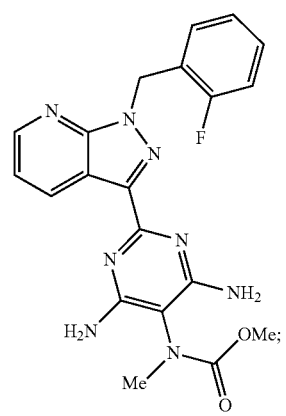 [SMILES: COC(=O)N(C)c1c(N)nc(-c2nn(Cc3ccccc3F)c3ncccc23)nc1N]
neliciguat (BAY 60-4552, described in WO 2003095451)
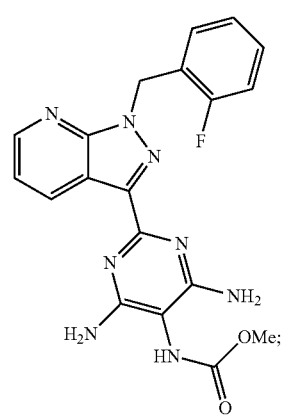 [SMILES: COC(=O)Nc1c(N)nc(-c2nn(Cc3ccccc3F)c3ncccc23)nc1N]
vericiguat (BAY 1021189)
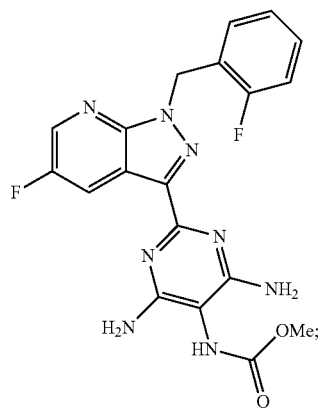 [SMILES: COC(=O)Nc1c(N)nc(-c2nn(Cc3ccccc3F)c3ncc(F)cc23)nc1N]
BAY 41-2272 (described in DE19834047 and DE19942809)
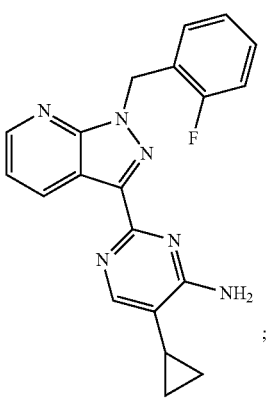 [SMILES: Nc1nc(-c2nn(Cc3ccccc3F)c3ncccc23)ncc1C1CC1]
BAY 41-8543 (described in DE19834044)
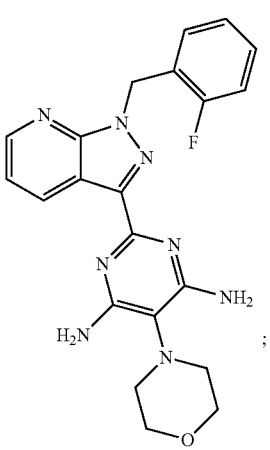 [SMILES: Nc1nc(-c2nn(Cc3ccccc3F)c3ncccc23)nc(N)c1N1CCOCC1]

etriciguat (described in WO 2003086407)

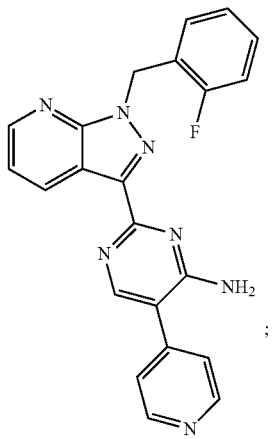 [SMILES: Nc1nc(-c2nn(Cc3ccccc3F)c3ncccc23)ncc1-c1ccncc1]

CFM-1571 (described in patent publication WO2000027394)

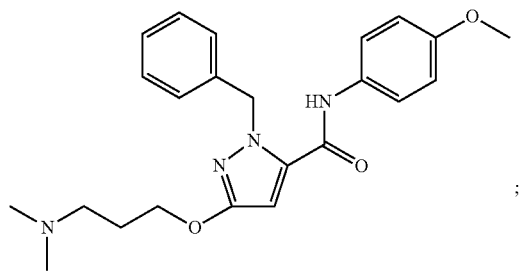

A-344905, its acrylamide analogue A-350619 and the aminopyrimidine analogue A-778935

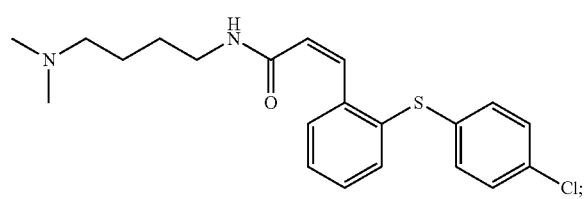

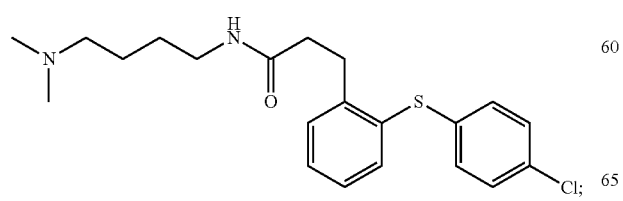

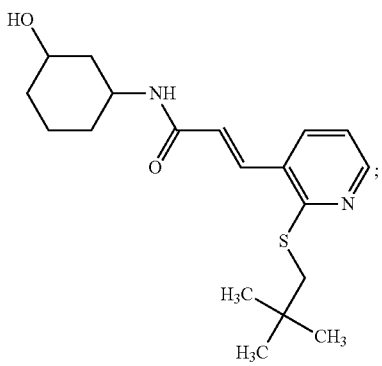

and other sGC stimulators described in one of publications US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and other compounds described in Tetrahedron Letters (2003), 44(48): 8661-8663.

(8) Compounds that inhibit the degradation of cGMP, such as:

PDE5 inhibitors, such as, for example, sildenafil (Viagra®) and related agents such as avanafil, lodenafil, mirodenafil, sildenafil citrate (Revatio®), tadalafil (Cialis® or Adcirca®), vardenafil (Levitra®) and udenafil; alprostadil; dipyridamole and PF-00489791; and PDE9 inhibitors, such as, for example, PF-04447943, and PDE10 inhibitors such as, for example, PF-02545920 (PF-10).

(9) Calcium channel blockers of the following types:
dihydropyridine calcium channel blockers such asamlodipine (Norvasc®), aranidipine (Sapresta®), azelnidipine (Calblock®), barnidipine (HypoCa®), benidipine (Coniel®), cilnidipine (Atelec®, Cinalong®, Siscard®), clevidipine (Cleviprex®), diltiazem, efonidipine (Landel®), felodipine (Plendil®), lacidipine (Motens®, Lacipil®), lercanidipine (Zanidip®), manidipine (Calslot®, Madipine®), nicardipine (Cardene®, Carden SR®), nifedipine (Procardia®, Adalat®), nilvadipine (Nivadil®), nimodipine (Nimotop®), nisoldipine (Baymycard®, Sular®, Syscor®), nitrendipine (Cardif®, Nitrepin®, Baylotensin®), pranidipine (Acalas®), isradipine (Lomir®);
phenylalkylamine calcium channel blockers such as verapamil (Calan®, Isoptin®)

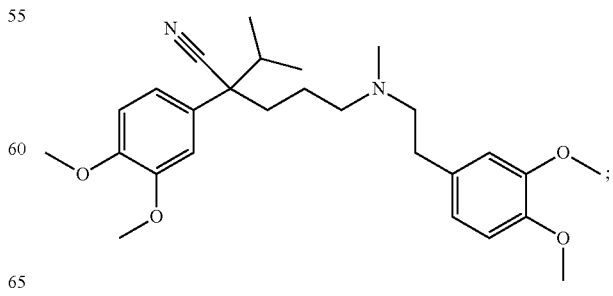

and gallopamil (Procorum®, D600);
benzothiazepines such asdiltiazem (Cardizem®)

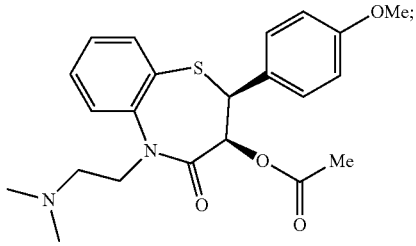 [SMILES: COc1ccc([C@@H]2Sc3ccccc3N(CCN(C)C)C(=O)[C@@H]2OC(C)=O)cc1]

and
nonselective calcium channel inhibitors such as mibefradil, bepridil, fluspirilene, and fendiline.
(10) Endothelin receptor antagonists (ERAs) such as the dual ($ET_A$ and $ET_B$) endothelin receptor antagonist bosentan (Tracleer®), sitaxentan (Thelin®) or ambrisentan (Letairis®).
(11) Prostacyclin derivatives or analogues, such asprostacyclin (prostaglandin $I_2$), epoprostenol (synthetic prostacyclin, Flolan®), treprostinil (Remodulin®), iloprost (Ilomedin®), iloprost (Ventavis®); and oral and inhaled forms of Remodulin® under development.
(12) Antihyperlipidemics such as the following types:
bile acid sequestrants like cholestyramine, colestipol, colestilan, colesevelam or sevelamer;
statins like atorvastatin, simvastatin, lovastatin, fluvastatin, pitavastatin, rosuvastatin and pravastatin;
cholesterol absorption inhibitors such as ezetimibe;
other lipid lowering agents such as icosapent ethyl ester, omega-3-acid ethyl esters, reducol;
fibric acid derivatives such as clofibrate, bezafibrate, clinofibrate, gemfibrozil, ronifibrate, binifibrate, fenofibrate, ciprofibrate, choline fenofibrate;
nicotinic acid derivatives such as acipimox and niacin;
combinations of statins, niacin and intestinal cholesterol absorption-inhibiting supplements (ezetimibe and others) and fibrates; and
antiplatelet therapies such as clopidogrel bisulfate.
(13) Anticoagulants, such as the following types:
coumarines (Vitamin K antagonists) such as warfarin (Coumadin®), cenocoumarol, phenprocoumon and phenindione;
heparin and derivatives such as low molecular weight heparin, fondaparinux and idraparinux;
direct thrombin inhibitors such as argatroban, lepirudin, bivalirudin, dabigatran and ximelagatran (Exanta®); and
tissue-plasminogen activators, used to dissolve clots and unblock arteries, such as alteplase.
(14) Antiplatelet drugs such as, for instance, topidogrel, ticlopidine, dipyridamole and aspirin.
(15) ACE inhibitors, for example the following types:
sulfhydryl-containing agents such as captopril (Capoten®) and zofenopril;
dicarboxylate-containing agents such as enalapril (Vasotec/Renitec®), ramipril (Altace®/Tritace®/Ramace®/Ramiwin®), quinapril (Accupril®), perindopril (Coversyl®/Aceon®), lisinopril (Lisodur®/Lopril®/Novatec®/Prinivil®/Zestril®) and benazepril (Lotensin®);
phosphonate-containing agents such as fosinopril;
naturally occurring ACE inhibitors such as casokinins and lactokinins, which are breakdown products of casein and whey that occur naturally after ingestion of milk products, especially cultured milk;
the lactotripeptides Val-Pro-Pro and Ile-Pro-Pro produced by the probiotic *Lactobacillus helveticus* or derived from casein also having ACE-inhibiting and antihypertensive functions;
other ACE inhibitors such as alacepril, delapril, cilazapril, imidapril, trandolapril, temocapril, moexipril and pirapril.
(16) Supplemental oxygen therapy.
(17) Beta blockers, such as the following types:
non-selective agents such as alprenolol, bucindolol, carteolol, carvedilol, labetalol, nadolol, penbutolol, pindolol, oxprenonol, acebutolol, sotalol, mepindolol, celiprolol, arotinolol, tertatolol, amosulalol, nipradilol, propranolol and timolol;
$β_1$-Selective agents such as cebutolol, atenolol, betaxolol, bisoprolol, celiprolol, dobutamine hydrochloride, irsogladine maleate, carvedilol, talinolol, esmolol, metoprolol and nebivolol; and
$β_2$-Selective agents such as butaxamine.
(18) Antiarrhythmic agents such as the following types:
Type I (sodium channel blockers) such as quinidine, lidocaine, phenytoin, propafenone;
Type III (potassium channel blockers) such as amiodarone, dofetilide and sotalol; and
Type V such as adenosine and digoxin.
(19) Diuretics such as thiazide diuretics, for example chlorothiazide, chlorthalidone and hydrochlorothiazide, bendroflumethiazide, cyclopenthiazide, methyclothiazide, polythiazide, quinethazone, xipamide, metolazone, indapamide, cicletanine; loop diuretics, such as furosemide and toresamide; potassium-sparing diuretics such as amiloride, spironolactone, canrenoate potassium, eplerenone and triamterene; combinations of these agents; other diuretics such as acetazolamid and carperitide.
(20) Direct-acting vasodilators such as hydralazine hydrochloride, diazoxide, sodium nitroprusside, cadralazine; other vasodilators such as isosorbide dinitrate and isosorbide 5-mononitrate.
(21) Exogenous vasodilators such as Adenocard® and alpha blockers.
(22) Alpha-1-adrenoceptor antagonists such as prazosin, indoramin, urapidil, bunazosin, terazosin and doxazosin; atrial natriuretic peptide (ANP), ethanol, histamine-inducers, tetrahydrocannabinol (THC) and papaverine.
(23) Bronchodilators of the following types:
short acting $β_2$ agonists, such as albutamol or albuterol (Ventolin®) and terbutaline;
long acting $β_2$ agonists (LABAs) such as salmeterol and formoterol;
anticholinergics such as pratropium and tiotropium; and
theophylline, a bronchodilator and phosphodiesterase inhibitor.
(24) Corticosteroids such as beclomethasone, methylprednisolone, betamethasone, prednisone, prednisolone, triamcinolone, dexamethasone, fluticasone, flunisolide, hydrocortisone, and corticosteroid analogs such as budesonide.
(25) Dietary supplements such as, for example omega-3 oils; folic acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; vitamin C, Vitamin E, Vitamin K2; testosterone supplements, testosterone transdermal patch; zoraxel, naltrexone, bremelanotide and melanotan II.
(26) PGD2 receptor antagonists.
(27) Immunosuppressants such as cyclosporine (cyclosporine A, Sandimmune®, Neoral®), tacrolimus (FK-506, Prograf®), rapamycin (Sirolimus®, Rapamune®) and other FK-506 type immunosuppressants, mycophenolate, e.g., mycophenolate mofetil (CellCept®).

(28) Non-steroidal anti-asthmatics such as β2-agonists like terbutaline, metaproterenol, fenoterol, isoetharine, albuterol, salmeterol, bitolterol and pirbuterol; β2-agonist-corticosteroid combinations such as salmeterol-fluticasone (Advair®), formoterol-budesonide (Symbicort®), theophylline, cromolyn, cromolyn sodium, nedocromil, atropine, ipratropium, ipratropium bromide and leukotriene biosynthesis inhibitors (zileuton, BAY1005).

(29) Non-steroidal anti-inflammatory agents (NSAIDs) such as propionic acid derivatives like alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives such as indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac; fenamic acid derivatives such as flufenamic acid, meclofenamic acid, mefenamic acid, niflumic acid and tolfenamic acid; biphenylcarboxylic acid derivatives such as diflunisal and flufenisal; oxicams such as isoxicam, piroxicam, sudoxicam and tenoxican; salicylates such as acetyl salicylic acid and sulfasalazine; and the pyrazolones such as apazone, bezpiperylon, feprazone, mofebutazone, oxyphenbutazone and phenylbutazone.

(30) Cyclooxygenase-2 (COX-2) inhibitors such as celecoxib (Celebrex®), rofecoxib (Vioxx®), valdecoxib, etoricoxib, parecoxib and lumiracoxib; opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine.

(31) Anti-diabetic agents such as insulin and insulin mimetics; sulfonylureas such as glyburide, glybenclamide, glipizide, gliclazide, gliquidone, glimepiride, meglinatide, tolbutamide, chlorpropamide, acetohexamide and olazamide; biguanides such as metformin (Glucophage®); α-glucosidase inhibitors such as acarbose, epalrestat, voglibose, miglitol; thiazolidinone compounds such as rosiglitazone (Avandia®), troglitazone (Rezulin®), ciglitazone, pioglitazone (Actor®) and englitazone; insulin sensitizers such as pioglitazone and rosiglitazone; insulin secretagogues such as repaglinide, nateglinide and mitiglinide; incretin mimetics such as exanatide and liraglutide; amylin analogues such as pramlintide; glucose lowering agents such as chromium picolinate, optionally combined with biotin; dipeptidyl peptidase IV inhibitors such as sitagliptin, vildagliptin, saxagliptin, alogliptin and linagliptin.

(32) HDL cholesterol-increasing agents such as anacetrapib and dalcetrapib.

(33) Antiobesity drugs such as methamphetamine hydrochloride, amfepramone hydrochloride (Tenuate®), phentermine (Ionamin®), benzfetamine hydrochloride (Didrex®), phendimetrazine tartrate (Bontril®, Prelu-2®, Plegine®), mazindol (Sanorex®), orlistat (Xenical®), sibutramine hydrochloride monohydrate (Meridia®, Reductil®), rimonabant (Acomplia®), amfepramone, chromium picolinate; combination such as phentermine/topiramate, bupropion/naltrexone, sibutramine/metformin, bupropion SR/zonisamide SR, salmeterol, xinafoate/fluticasone propionate; lorcaserin hydrochloride, phentermine/topiramate, cetilistat, exenatide, liraglutide, metformin hydrochloride, sibutramine/metformin, bupropion SR/zonisamide SR, CORT-108297, canagliflozin, chromium picolinate, GSK-1521498, LY-377604, metreleptin, obinepitide, P-57AS3, PSN-821, salmeterol xinafoate/fluticasone propionate, sodium tungstate, somatropin (recombinant), tesamorelin, tesofensine, velneperit, zonisamide, beloranib hemioxalate, insulinotropin, resveratrol, sobetirome, tetrahydrocannabivarin and beta-lapachone.

(34) Angiotensin receptor blockers such as losartan, valsartan, candesartan, cilexetil, eprosaran, irbesartan, telmisartan, olmesartran, medoxomil, azilsartan and medoxomil.

(35) Renin inhibitors such as aliskiren hemifumirate.

(36) Centrally acting alpha-2-adrenoceptor agonists such as methyldopa, clonidine and guanfacine.

(37) Adrenergic neuron blockers such as guanethidine and guanadrel.

(38) Imidazoline I-1 receptor agonists such as rimenidine dihydrogen phosphate and moxonidine hydrochloride hydrate.

(39) Aldosterone antagonists such as spironolactone and eplerenone.

(40) Potassium channel activators such as pinacidil.

(41) Dopamine D1 agonists such as fenoldopam mesilate; other dopamine agonists such as ibopamine, dopexamine and docarpamine.

(42) 5-HT2 antagonists such as ketanserin.

(43) Vasopressin antagonists such as tolvaptan.

(44) Calcium channel sensitizers such as levosimendan or activators such as nicorandil.

(45) PDE-3 inhibitors such as amrinone, milrinone, enoximone, vesnarinone, pimobendan, and olprinone.

(46) Adenylate cyclase activators such as colforsin dapropate hydrochloride.

(47) Positive inotropic agents such as digoxin and metildigoxin; metabolic cardiotonic agents such as ubidecarenone; brain natriuretic peptides such as nesiritide.

(48) Drugs used for the treatment of erectile dysfunction such as alprostadil, aviptadil, and phentolamine mesilate.

(49) Drugs used in the treatment of obesity, including but not limited to, methamphetamine hydrochloride (Desoxyn®), amfepramone hydrochloride (Tenuate®), phentermine (Ionamin®), benzfetamine hydrochloride (Didrex®), phendimetrazine hydrochloride (Bontril®, Prelu-2®, Plegine®), mazindol (Sanorex®) and orlistat (Xenical®).

(50) Drugs used for the treatment of Alzheimer's disease and dementias such as the following types:
acetyl cholinesterase inhibitors including galantamine (Razadyne®), rivastigmine (Exelon®), donepezil (Aricept®) and tacrine (Cognex®);
NMDA receptor antagonists such as memantine (Namenda®); and
oxidoreductase inhibitors such as idebenone.

(51) Psychiatric medications such as the following types:
ziprasidone (Geodon™), risperidone (Risperdal™), olanzapine (Zyprexa™), valproate;
dopamine D4 receptor antagonists such as clozapine;
dopamine D2 receptor antagonists such as nemonapride;
mixed dopamine D1/D2 receptor antagonists such as zuclopenthixol;
GABA A receptor modulators such as carbamazepine;
sodium channel inhibitors such as lamotrigine;
monoamine oxidase inhibitors such as moclobemide and indeloxazine;
primavanserin, perospirone; and
PDE4 inhibitors such as rolumilast.

(52) Drugs used for the treatment of movement disorders or symptoms such as the following types:
catechol-O-methyl transferase inhibitors such as entacapone;

monoamine oxidase B inhibitors such as selegiline;
dopamine receptor modulators such as levodopa;
dopamine D3 receptor agonists such as pramipexole;
decarboxylase inhibitors such as carbidopa;
other dopamine receptor agonists such as pergolide, ropinirole, cabergoline;
ritigonide, istradefylline, talipexole; zonisamide and safinamide; and
synaptic vesicular amine transporter inhibitors such as tetrabenazine.
(53) Drugs used for the treatment of mood or affective disorders or OCD such as the following types
tricyclic antidepressants such as amitriptyline (Elavil®), desipramine (Norpramin®), imipramine (Tofranil®), amoxapine (Asendin®), nortriptyline and clomipramine;
selective serotonin reuptake inhibitors (SSRIs) such as paroxetine (Paxil®), fluoxetine (Prozac®), sertraline (Zoloft®), and citralopram (Celexa®);
doxepin (Sinequan®), trazodone (Desyrel®) and agomelatine;
selective norepinephrine reuptake inhibitors (SNRIs) such as venlafaxine, reboxetine and atomoxetine; dopaminergic antidepressants such as bupropion and amineptine.
(54) Drugs for the enhancement of synaptic plasticity such as the following types:
nicotinic receptor antagonists such as mecamylamine; and mixed 5-HT, dopamine and norepinephrine receptor agonists such as lurasidone.
(55) Drugs used for the treatment of ADHD such as amphetamine; 5-HT receptor modulators such as vortioxetine and alpha-2 adrenoceptor agonists such as clonidine.
(56) Neutral endopeptidase (NEP) inhibitors such as sacubitril, omapatrilat; and
(57) Methylene blue (MB).

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

All references provided in the Examples are herein incorporated by reference. As used herein, all abbreviations, symbols and conventions are consistent with those used in the contemporary scientific literature. See, e.g. Janet S. Dodd, ed., The ACS Style Guide: A Manual for Authors and Editors, $2^{nd}$ Ed., Washington, D.C.: American Chemical Society, 1997, herein incorporated in its entirety by reference.

Example 1: Compound Syntheses

Intermediate 1a

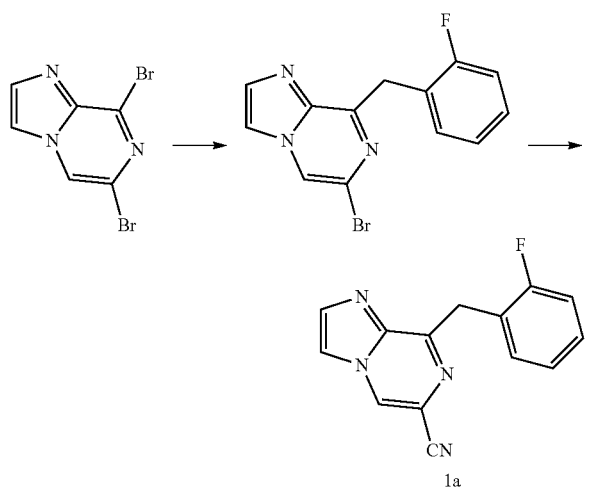

8-(2-Fluorobenzyl)imidazo[1,2-a]pyrazine-6-carbonitrile (1a)

The title compound was synthesized in 2 steps according to a patent literature procedure (WO2015/187470A1) as a yellow solid (0.60 g, 39% yield over 2 steps). $^1$H NMR (500 MHz, Methanol-$d_4$) δ (ppm) 9.09 (s, 1H), 8.14 (s, 1H), 7.91 (s, 1H), 7.35 (t, 1H), 7.28 (m, 1H), 7.10 (m, 2H), 4.60 (s, 2H).

Using a similar procedure for the synthesis of 1a, the following nitrile intermediates were prepared. The reaction conditions (such as reagents ratio, temperature and reaction time) were modified as needed.
8-Phenylimidazo[1,2-a]pyrazine-6-carbonitrile;
8-Benzylimidazo[1,2-a]pyrazine-6-carbonitrile;
8-(4-Fluorobenzyl)imidazo[1,2-a]pyrazine-6-carbonitrile;
8-(2,3-Difluorobenzyl)imidazo[1,2-a]pyrazine-6-carbonitrile;
8-(2,5-Difluorobenzyl)imidazo[1,2-a]pyrazine-6-carbonitrile;
8-(3,3,4,4,4-Pentafluorobutyl)imidazo[1,2-a]pyrazine-6-carbonitrile,
8-(2-Fluorobenzyl)-2-methylimidazo[1,2-a]pyrazine-6-carbonitrile;
8-(3,5-Difluorobenzyl)imidazo[1,2-a]pyrazine-6-carbonitrile;
8-(3,5-Difluoro-4-methylbenzyl)imidazo[1,2-a]pyrazine-6-carbonitrile.

Alternatively, Intermediate 1a and related analogs (Such as Intermediate 1b) can be synthesized by the following procedure:

Step 1: Synthesis of 6-bromo-8-(2-fluorobenzyl)imidazo[1,2-a]pyrazine

A suspension of dry zinc powder (47 g, 720 mmol, dried by heating in vacuo) in THF (750 mL) was treated with 1,2-dibromoethane (1 mL) and the resultant mixture was heated to 50° C. Chlorotrimethylsilane (1 mL) was then added. After stirring at 48-50° C. for 30 min, the mixture was cooled to ambient temperature. Dry lithium chloride (30 g, 710 mmol, dried by heating in vacuo) was added, followed by dropwise addition of a solution of 2-fluorobenzyl bromide (74 g, 390 mmol) in THF (100 mL) (note: exothermic, reaction temperature was maintained below 48° C.). The mixture was stirred for 1 hour at ambient temperature. A slurry of 6,8-dibromoimidazo[1,2-a]pyrazine (99 g, 360 mmol) and Pd(PPh$_3$)$_2$Cl$_2$ (7.8 g, 11 mmol) in THF (500 mL) was degassed by bubbling with nitrogen for 10 min and added quickly to the 2-fluorobenzylzinc bromide reagent with the aid of THF (100 mL). The reaction vessel was purged with nitrogen and the mixture was stirred overnight at ambient temperature until complete consumption of starting material. The reaction was quenched with saturated NH$_4$Cl solution (800 mL). The brown organic phase was concentrated to dryness, re-dissolved in DCM (1.3 L) and filtered through a bed of Celite. The organic layer in the filtrate was collected, decolorized with activated charcoal (45 g), filtered through Celite and concentrated to dryness. The crude material was dried azeotropically with toluene (2×500 mL) and carried forward without purification.

Step 2: Synthesis of 8-(2-fluorobenzyl)imidazo[1,2-a]pyrazine-6-carbonitrile

A reaction mixture comprised of the crude material (360 mmol, theoretical yield) from the previous step, zinc cyanide (35 g, 300 mmol), Pd$_2$(dba)$_3$ (16 g, 18 mmol), 1,1'-bis(diphenylphosphino)ferrocene (dppf) (14 g, 25 mmol), and zinc powder (1.0 g) in DMF (800 mL) was degassed under nitrogen for 10 minutes and then heated at 85° C. until complete consumption of starting material. The reaction was cooled to ambient temperature and poured into EtOAc (1.5 L), 10% NH$_4$Cl solution (1.1 L) and 5% NaCl solution (1.0 L). The organic layer was filtered through a bed of Celite and washed with EtOAc (2×750 mL). The organic filtrate was washed with 10% NaCl solution (2×1.0 L), decolorized with activated charcoal (75 g), filtered through Celite and washed with EtOAc (2×300 mL). The filtrate was concentrated to dryness and suspended in a mixture of DCM (150 mL) and MTBE (300 mL). After stirring for 1 hour, the product was collected by filtration, washed with MTBE (2×100 mL) and dried in a vacuum oven at 45° C. The title compound was obtained as a brown solid (52 g, 57% yield).

$^1$H NMR (500 MHz, Methanol-$d_4$) δ (ppm) 9.09 (s, 1H), 8.13 (s, 1H), 7.91 (s, 1H), 7.35 (app. t, 1H), 7.27 (m, 2H), 7.13-7.06 (m, 2H), 4.60 (s, 2H).

Intermediate 1b

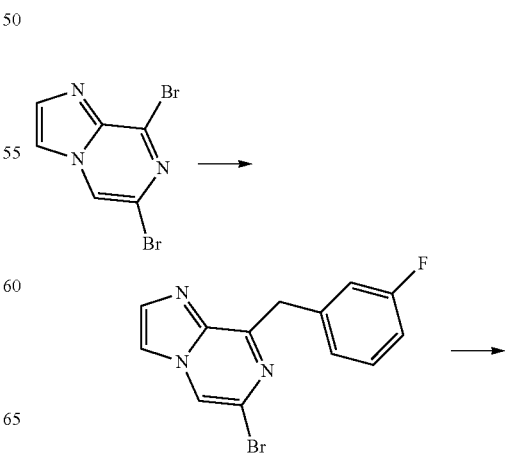

-continued

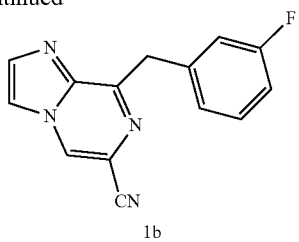

1b 8-(3-Fluorobenzyl)imidazo[1,2-a]pyrazine-6-carbonitrile (1b)

The title compound was synthesized in 2 steps.

Step 1: Synthesis of 6-bromo-8-(3-fluorobenzyl)imidazo[1,2-a]pyrazine

A suspension of dry zinc powder (2.6 g, 40 mmol) in THF (50 mL) was treated with 1,2-dibromoethane (0.30 mL, 3.5 mmol) and the resultant mixture was heated at 50° C. for 5 minutes. Chlorotrimethylsilane (0.30 mL, 2.4 mmol) was then added and the mixture was cooled to ambient temperature. Dry lithium chloride (1.7 g, 40 mmol) was added, followed by dropwise addition of a solution of 3-fluorobenzyl bromide (4.8 g, 26 mmol) in THF (25 mL) (note: exothermic, reaction temperature was maintained below 35° C.). The mixture was stirred for 1 hour at ambient temperature, followed by addition of a slurry of 6,8-dibromoimidazo[1,2-a]pyrazine (5.9 g, 21 mmol) and Pd(PPh$_3$)$_2$Cl$_2$ (0.25 g, 0.36 mmol) in THF (75 mL). The reaction mixture was degassed with nitrogen and stirred overnight at ambient temperature until complete consumption of starting material. The reaction mixture was concentrated and diluted with DCM (100 mL) and 10% NH$_4$Cl solution (100 mL). The thick mixture was filtered through a bed of Celite, and the organic layer in the filtrate was collected. The organic layer was dried and decolorized with Na$_2$SO$_4$ (10 g) and activated charcoal (7 g), filtered through Celite and concentrated to yield a crude orange oil (7.1 g) which was carried forward without purification.

Step 2: Synthesis of 8-(3-fluorobenzyl)imidazo[1,2-a]pyrazine-6-carbonitrile

A reaction mixture comprised of the crude material (21 mmol, theoretical yield) from the previous step, zinc cyanide (3.0 g, 26 mmol), Pd$_2$(dba)$_3$ (1.9 g, 2.1 mmol), 1,1'-bis(diphenylphosphino)ferrocene (dppf) (1.5 g, 2.7 mmol), and zinc powder (0.30 g, 4.6 mmol) in DMF (70 mL) was degassed under nitrogen for 5 minutes and then heated at 110° C. until complete consumption of starting material. The reaction was cooled to ambient temperature, diluted with EtOAc (150 mL) and filtered through a bed of celite. The organic filtrate was washed with 10% NH$_4$Cl solution (2×100 mL), dried over Na$_2$SO$_4$, filtered and concentrated to afford a brown oil which was purified by column chromatography (15 to 40% EtOAc/hexanes gradient) to afford the title compound as an off-white solid (2.4 g, 45% yield).

$^1$H NMR (500 MHz, DMSO-d$_6$) δ (ppm) 9.37 (s, 1H), 8.25 (s, 1H), 7.98 (s, 1H), 7.29-7.39 (m, 1H), 7.23 (d, 2H), 6.99-7.12 (m, 1H), 4.45-4.56 (m, 2H).

Using a similar procedure for the synthesis of Intermediates 1a and 1b, the following nitrile intermediates were prepared. The reaction conditions (such as reagents ratio, temperature and reaction time) were modified as needed.

8-(2,6-Difluorobenzyl)imidazo[1,2-a]pyrazine-6-carbonitrile;

8-(3-Fluoro-4-methylbenzyl)imidazo[1,2-a]pyrazine-6-carbonitrile.

Intermediate 2

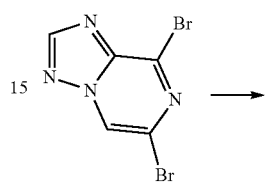

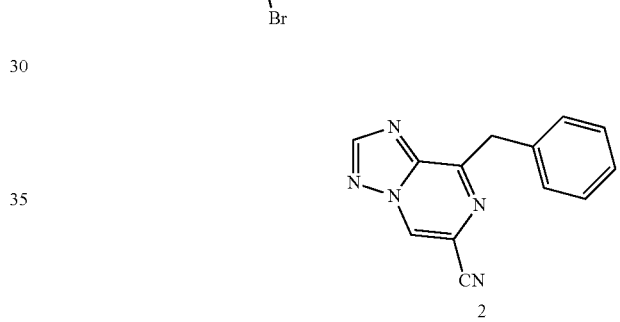

8-Benzyl-[1,2,4]triazolo[1,5-a]pyrazine-6-carbonitrile (2)

The title compound was synthesized in 2 steps according to a patent literature procedure (WO2016/081668A1) as a gold residue (0.12 g, 23% yield over 2 steps).

$^1$H NMR (500 MHz, DMSO-d$_6$) δ (ppm) 9.96 (s, 1H), 8.94 (s, 1H), 7.39 (d, 2H) 7.30 (dd, 2H), 7.23 (t, 1H), 4.53 (s, 2H).

Using a similar procedure for the synthesis of 2, the following nitrile intermediate was prepared. The reaction conditions (such as reagents ratio, temperature and reaction time) were modified as needed.

8-(2-Fluorobenzyl)-[1,2,4]triazolo[1,5-a]pyrazine-6-carbonitrile.

8-(2,3-Difluorobenzyl)-[1,2,4]triazolo[1,5-a]pyrazine-6-carbonitrile;

8-(3-Fluorobenzyl)-[1,2,4]triazolo[1,5-a]pyrazine-6-carbonitrile;

8-(2,5-Difluorobenzyl)-[1,2,4]triazolo[1,5-a]pyrazine-6-carbonitrile;

8-(3,5-Difluorobenzyl)-[1,2,4]triazolo[1,5-a]pyrazine-6-carbonitrile.

Compound I-1

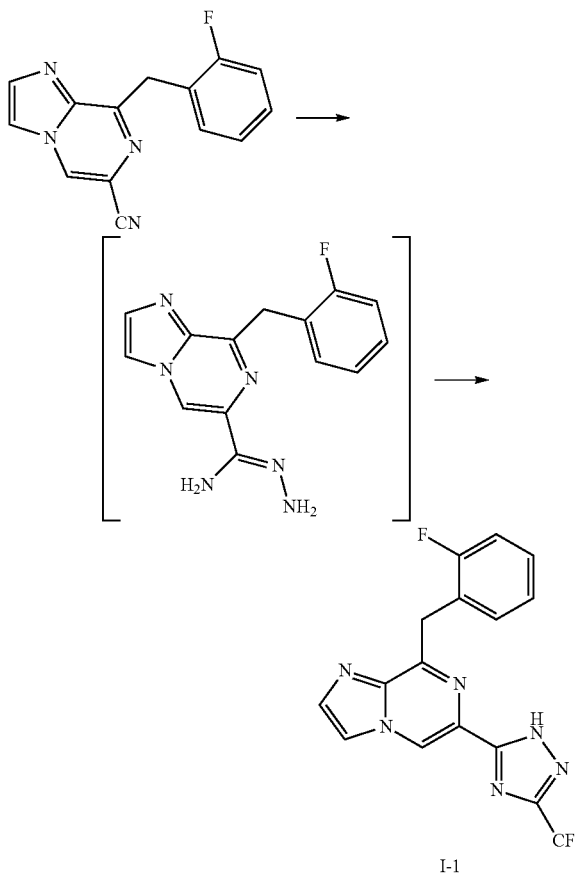

General Procedure A: 8-(2-fluorobenzyl)-6-(3-(trifluoromethyl)-1H-1,2,4-triazol-5-yl)imidazo[1,2-a]pyrazine (I-1)

To a solution of 8-(2-fluorobenzyl)imidazo[1,2-a]pyrazine-6-carbonitrile (Ia) (4.0 g, 16 mmol) in methanol (40 mL) was added anhydrous hydrazine (3.1 mL, 100 mmol). After stirring at ambient temperature overnight, complete disappearance of starting material was observed. The reaction was concentrated in vacuo, residual hydrazine was removed with methanol and toluene chasing, and the resultant foam was dried under vacuum overnight. The brown foam was taken up in DCM (75 mL) and 2,2,2-trifluoroacetic anhydride (3.8 ml, 27 mmol) was added dropwise to prevent a strong exothermic reaction. The reaction was stirred at ambient temperature until complete consumption of the amidrazone intermediate. The solvent was removed in vacuo and dried to a yellow residue. The residue was taken up in AcOH (10 mL) and EtOH (100 mL) and heated at 90° C. for 1 hour. The reaction mixture was cooled to ambient temperature and concentrated to half the reaction volume. The resultant thick suspension was filtered, and the filtrate was concentrated to brown oil. The crude material was purified using silica gel chromatography (10-100% EtOAc/hexanes gradient) to isolate the title compound (4.0 g, 69% yield) as a tan solid.

$^1$H NMR (500 MHz, DMSO-$d_6$) δ (ppm) 15.46 (s, 1H), 9.45 (s, 1H), 8.26 (s, 1H), 7.87 (s, 1H), 7.43 (t, 1H), 7.22-7.32 (m, 1H), 7.14-7.22 (m, 1H), 7.09 (t, 1H), 4.60 (s, 2H). LCMS [M+H]=363.1

Compound I-2

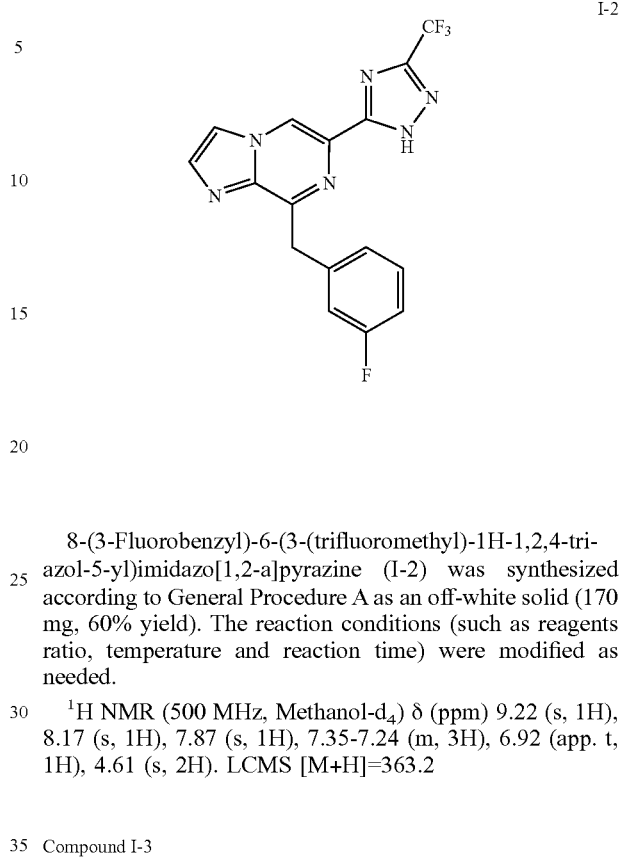

8-(3-Fluorobenzyl)-6-(3-(trifluoromethyl)-1H-1,2,4-triazol-5-yl)imidazo[1,2-a]pyrazine (I-2) was synthesized according to General Procedure A as an off-white solid (170 mg, 60% yield). The reaction conditions (such as reagents ratio, temperature and reaction time) were modified as needed.

$^1$H NMR (500 MHz, Methanol-$d_4$) δ (ppm) 9.22 (s, 1H), 8.17 (s, 1H), 7.87 (s, 1H), 7.35-7.24 (m, 3H), 6.92 (app. t, 1H), 4.61 (s, 2H). LCMS [M+H]=363.2

Compound I-3

6-(3-(Difluoromethyl)-1H-1,2,4-triazol-5-yl)-8-(3-fluorobenzyl)imidazo[1,2-a]pyrazine (I-3) was synthesized according to General Procedure A, with the exception that 2,2-difluoroacetic anhydride was used as the acylating agent, as an off-white solid (160 mg, 55% yield). The reaction conditions (such as reagents ratio, temperature and reaction time) were modified as needed.

$^1$H NMR (500 MHz, Methanol-$d_4$) δ (ppm) 9.17 (s, 1H), 8.17 (s, 1H), 7.86 (s, 1H), 7.35-7.25 (m, 3H), 6.92 (m, 1H), 6.90 (t, 1H), 4.61 (s, 2H). LCMS [M+H]=345.2

Compound I-17

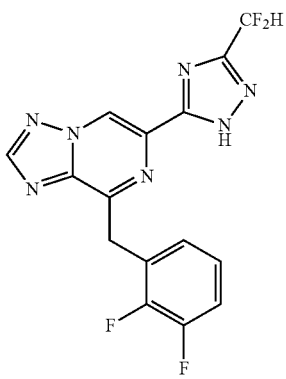

8-(2,3-Difluorobenzyl)-6-(3-(difluoromethyl)-1H-1,2,4-triazol-5-yl)-[1,2,4]triazolo[1,5-a]pyrazine (I-17) was synthesized according to General Procedure A, with the exception that 2,2-difluoroacetic anhydride was used as the acylating agent, as a white solid (120 mg, 62% yield). The reaction conditions (such as reagents ratio, temperature and reaction time) were modified as needed.

$^1$H NMR (500 MHz, DMSO-d$_6$) δ (ppm) 15.3 (s, 1H), 9.58 (s, 1H), 8.83 (s, 1H), 7.27-7.35 (m, 2H), 7.08-7.19 (m, 2H), 4.69 (s, 2H).

LCMS [M+H]=364.2

Compound I-19

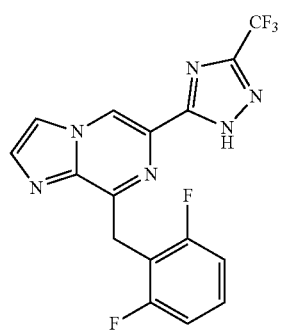

8-(2,6-Difluorobenzyl)-6-(3-(trifluoromethyl)-1H-1,2,4-triazol-5-yl)imidazo[1,2-a]pyrazine (I-19) was synthesized according to General Procedure A as an off-white solid (300 mg, 87% yield). The reaction conditions (such as reagents ratio, temperature and reaction time) were modified as needed.

$^1$H NMR (500 MHz, DMSO-d$_6$) δ (ppm) 15.3 (s, 1H), 9.43 (s, 1H), 8.25 (s, 1H), 7.85 (s, 1H), 7.37 (m, 1H), 7.08 (app. t, 2H), 4.63 (s, 2H).

LCMS [M+H]=381.2

Compound I-20

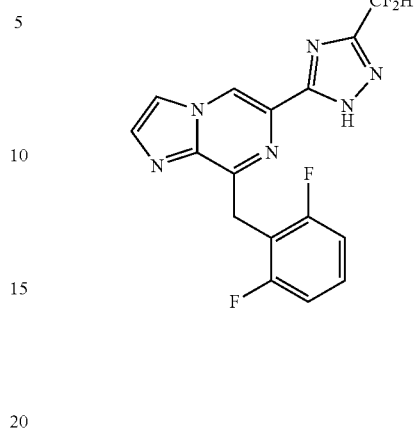

8-(2,6-Difluorobenzyl)-6-(3-(difluoromethyl)-1H-1,2,4-triazol-5-yl)imidazo[1,2-a]pyrazine (I-20) was synthesized according to General Procedure A, with the exception that 2,2-difluoroacetic anhydride was used as the acylating agent, as an off-white solid (240 mg, 72% yield). The reaction conditions (such as reagents ratio, temperature and reaction time) were modified as needed.

$^1$H NMR (500 MHz, DMSO-d$_6$) δ (ppm) 14.9 (s, 1H), 9.38 (s, 1H), 8.24 (s, 1H), 7.84 (s, 1H), 7.37 (m, 1H), 7.13 (t, 1H), 7.08 (app. t, 2H), 4.62 (s, 2H).

LCMS [M+H]=363.2

Compound I-21

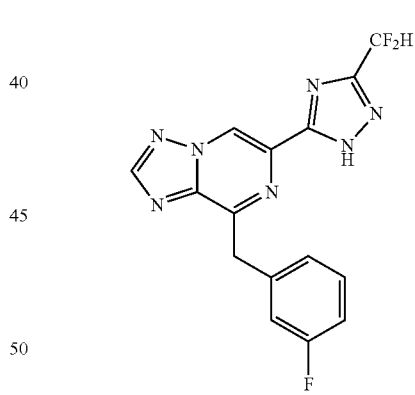

6-(3-(Difluoromethyl)-1H-1,2,4-triazol-5-yl)-8-(3-fluorobenzyl)-[1,2,4]triazolo[1,5-a]pyrazine (I-21) was synthesized according to General Procedure A, with the exception that 2,2-difluoroacetic anhydride was used as the acylating agent, as a white solid (110 mg, 29% yield). The reaction conditions (such as reagents ratio, temperature and reaction time) were modified as needed.

$^1$H NMR (500 MHz, DMSO-d$_6$) δ (ppm) 15.3 (s, 1H), 9.55 (s, 1H), 8.83 (s, 1H), 7.30-7.37 (m, 3H), 7.19 (t, 1H), 7.04-7.09 (m, 1H), 4.61 (s, 2H).

LCMS [M+H]=346.2

Compound I-22

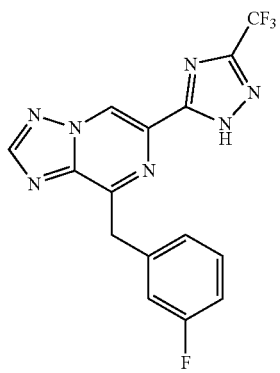

8-(3-Fluorobenzyl)-6-(3-(trifluoromethyl)-1H-1,2,4-triazol-5-yl)-[1,2,4]triazolo[1,5-a]pyrazine (I-22) was synthesized according to General Procedure A as an off-white solid (140 mg, 49% yield). The reaction conditions (such as reagents ratio, temperature and reaction time) were modified as needed.

$^1$H NMR (500 MHz, DMSO-$d_6$) δ (ppm) 15.7 (s, 1H), 9.62 (s, 1H), 8.85 (s, 1H), 7.32-7.36 (m, 3H), 7.05-7.08 (m, 1H), 4.62 (s, 2H).

LCMS [M+H]=364.2

Compound I-23

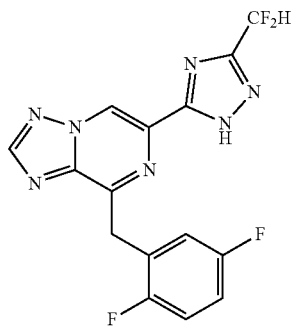

8-(2,5-Difluorobenzyl)-6-(3-(difluoromethyl)-1H-1,2,4-triazol-5-yl)-[1,2,4]triazolo[1,5-a]pyrazine (I-23) was synthesized according to General Procedure A, with the exception that 2,2-difluoroacetic anhydride was used as the acylating agent, as an off-white solid (120 mg, 72% yield). The reaction conditions (such as reagents ratio, temperature and reaction time) were modified as needed.

$^1$H NMR (500 MHz, Methanol-$d_4$) δ (ppm) 9.49 (s, 1H), 8.65 (s, 1H), 7.25 (m, 1H), 7.11 (m, 1H), 7.01 (m, 1H), 6.91 (t, 1H), 4.71 (s, 2H).

LCMS [M+H]=364.2

Compound I-24

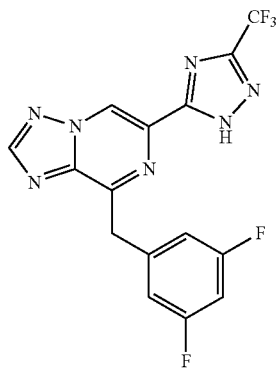

8-(3,5-Difluorobenzyl)-6-(3-(trifluoromethyl)-1H-1,2,4-triazol-5-yl)-[1,2,4]triazolo[1,5-a]pyrazine (I-24) was synthesized according to General Procedure A as a white solid (120 mg, 42% yield). The reaction conditions (such as reagents ratio, temperature and reaction time) were modified as needed.

$^1$H NMR (500 MHz, DMSO-$d_6$) δ (ppm) 15.7 (s, 1H), 9.63 (s, 1H), 8.86 (s, 1H), 7.23 (d, 2H), 7.11 (t, 1H), 4.63 (s, 2H).

LCMS [M+H]=382.2

Compound I-25

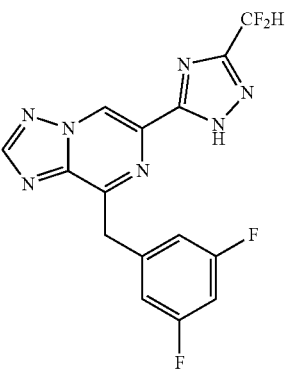

8-(3,5-Difluorobenzyl)-6-(3-(difluoromethyl)-1H-1,2,4-triazol-5-yl)-[1,2,4]triazolo[1,5-a]pyrazine (I-25) was synthesized according to General Procedure A, with the exception that 2,2-difluoroacetic anhydride was used as the acylating agent, as a white solid (157 mg, 57% yield). The reaction conditions (such as reagents ratio, temperature and reaction time) were modified as needed.

$^1$H NMR (500 MHz, DMSO-$d_6$) δ (ppm) 15.2 (s, 1H), 9.50 (s, 1H), 8.77 (s, 1H), 7.16 (d, 2H), 7.14 (t, 1H), 7.03 (m, 1H), 4.55 (s, 2H).

LCMS [M+H]=364.1

Compound I-4

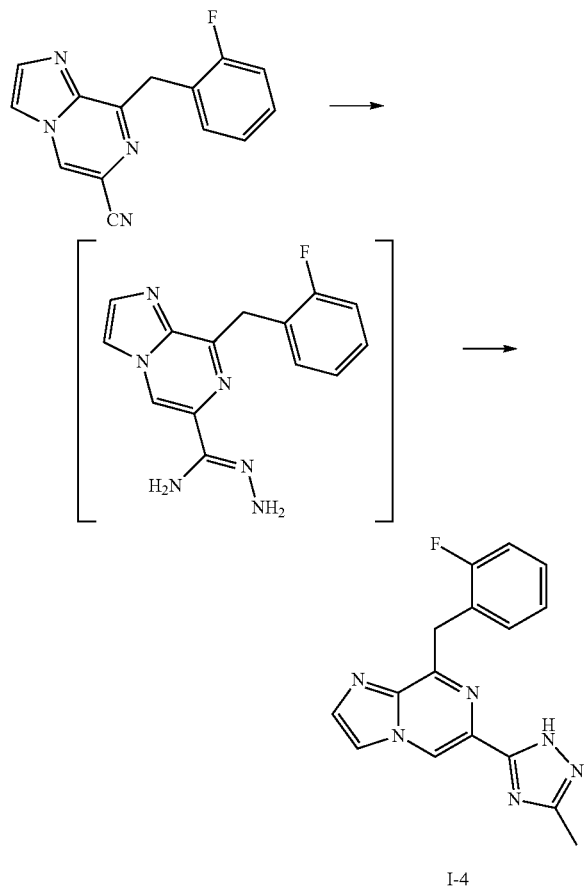

I-4

General Procedure B: 8-(2-fluorobenzyl)-6-(3-methyl-1H-1,2,4-triazol-5-yl)imidazo[1,2-a]pyrazine To a solution of 8-(2-fluorobenzyl)imidazo[1,2-a]pyrazine-6-carbonitrile (1a) (110 mg, 0.45 mmol) in methanol (2.0 mL) was added anhydrous hydrazine (0.08 mL, 2.7 mmol). After stirring at ambient temperature for 40 hours, complete disappearance of starting material was observed. The reaction was concentrated in vacuo and the residue was dried under vacuum overnight. The residue was taken up in DCM (6.0 mL) and acetic anhydride (0.09 ml, 0.89 mmol) added dropwise to prevent a strong exothermic reaction. The reaction was stirred at ambient temperature until complete consumption of the amidrazone intermediate. The solvent was removed in vacuo and dried to a yellow residue. The residue was taken up in AcOH (0.2 mL) and EtOH (10 mL) and heated at 120° C. for 5 hours in a microwave. The reaction mixture was cooled to ambient temperature and concentrated in vacuo. The crude material was purified using silica gel chromatography (10-30% acetonitrile/MeOH (7:1) in DCM gradient) to isolate the title compound (85 mg, 62% yield) as an off-white solid.

$^1$H NMR (500 MHz, Methanol-$d_4$) δ (ppm) 9.03 (s, 1H), 8.15 (s, 1H), 7.81 (s, 1H), 7.30 (app. t, 1H), 7.23 (m, 1H), 7.10-7.02 (m, 2H), 4.66 (s, 2H), 2.48 (s, 3H). LCMS [M+H]=309.2

Compound I-5

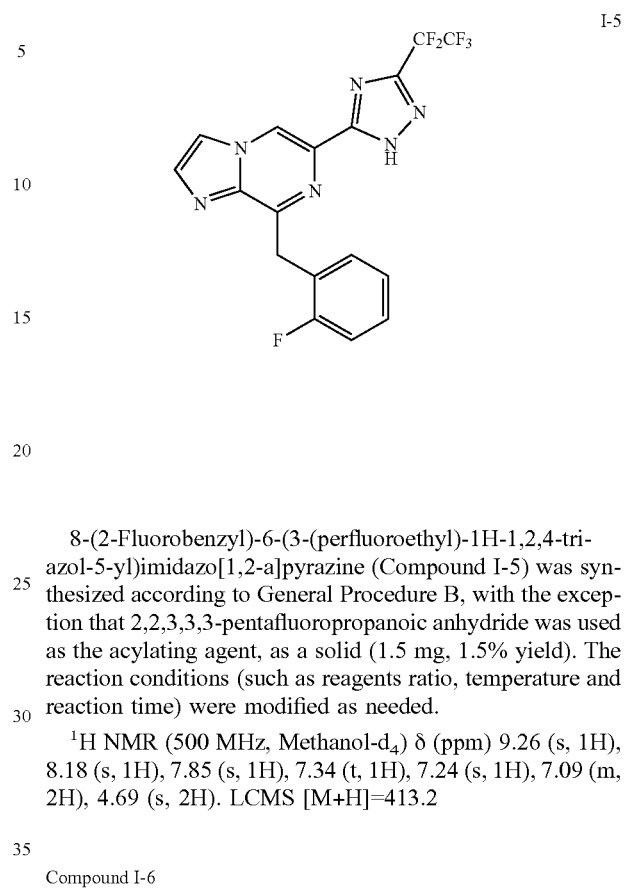

I-5

8-(2-Fluorobenzyl)-6-(3-(perfluoroethyl)-1H-1,2,4-triazol-5-yl)imidazo[1,2-a]pyrazine (Compound I-5) was synthesized according to General Procedure B, with the exception that 2,2,3,3,3-pentafluoropropanoic anhydride was used as the acylating agent, as a solid (1.5 mg, 1.5% yield). The reaction conditions (such as reagents ratio, temperature and reaction time) were modified as needed.

$^1$H NMR (500 MHz, Methanol-$d_4$) δ (ppm) 9.26 (s, 1H), 8.18 (s, 1H), 7.85 (s, 1H), 7.34 (t, 1H), 7.24 (s, 1H), 7.09 (m, 2H), 4.69 (s, 2H). LCMS [M+H]=413.2

Compound I-6

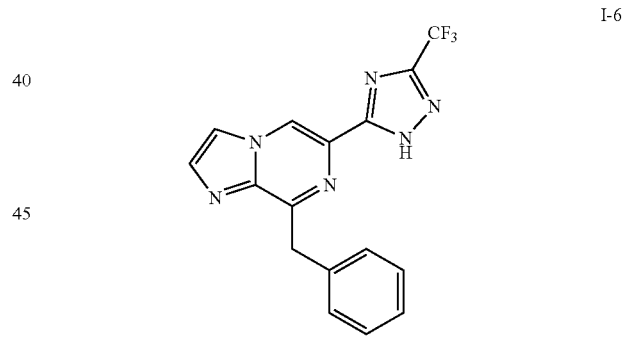

I-6

8-Benzyl-6-(3-(trifluoromethyl)-1H-1,2,4-triazol-5-yl)imidazo[1,2-a]pyrazine (I-6) was synthesized according to General Procedure B, with the exception that 2,2,2-trifluoroacetic anhydride was used as the acylating agent, as a white solid (57 mg, 52% yield). The reaction conditions (such as reagents ratio, temperature and reaction time) were modified as needed.

$^1$H NMR (500 MHz, Methanol-$d_4$) δ (ppm) 9.09 (s, 1H), 8.05 (s, 1H), 7.75 (s, 1H), 7.41 (d, 2H), 7.15 (t, 2H), 7.04-7.10 (m, 1H), 4.50 (s, 2H). LCMS [M+H]=345.2

Compound I-7

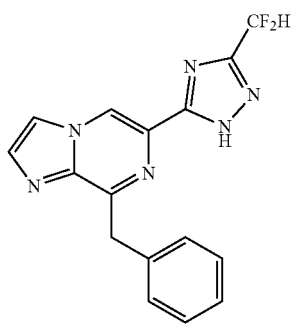

I-7

8-Benzyl-6-(3-(difluoromethyl)-1H-1,2,4-triazol-5-yl)imidazo[1,2-a]pyrazine (I-7) was synthesized according to General Procedure B, with the exception that 2,2-difluoroacetic anhydride was used as the acylating agent, as a white solid (15 mg, 16% yield). The reaction conditions (such as reagents ratio, temperature and reaction time) were modified as needed.

$^1$H NMR (500 MHz, Methanol-$d_4$) δ (ppm) 9.05 (s, 1H), 8.06 (s, 1H), 7.75 (s, 1H), 7.41 (d, 2H), 7.13-7.18 (m, 2H), 7.05-7.10 (m, 1H), 6.68-6.91 (m, 1H), 4.50 (s, 2H). LCMS [M+H]=327.2

Compound I-8

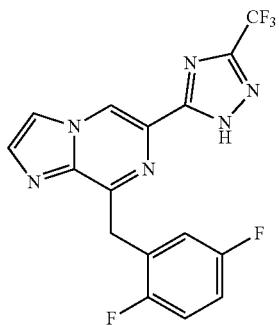

I-8

8-(2,5-Difluorobenzyl)-6-(3-(trifluoromethyl)-1H-1,2,4-triazol-5-yl)imidazo[1,2-a]pyrazine (I-8) was synthesized according to General Procedure B, with the exception that 2,2,2-trifluoroacetic anhydride was used as the acylating agent, as a white solid (18 mg, 31% yield). The reaction conditions (such as reagents ratio, temperature and reaction time) were modified as needed.

$^1$H NMR (500 MHz, Methanol-$d_4$) δ (ppm) 9.14 (s, 1H), 8.09 (s, 1H), 7.77 (s, 1H), 7.07 (m, 1H), 7.00 (m, 1H), 6.86-6.92 (m, 1H), 4.57 (s, 2H). LCMS [M+H]=381.2

Compound I-9

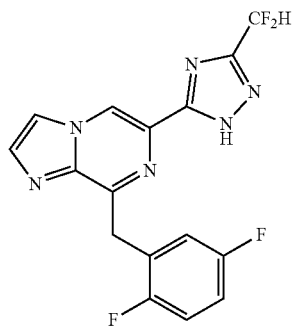

I-9

8-(2,5-Difluorobenzyl)-6-(3-(difluoromethyl)-1H-1,2,4-triazol-5-yl)imidazo[1,2-a]pyrazine (I-9) was synthesized according to General Procedure B, with the exception that 2,2-difluoroacetic anhydride was used as the acylating agent, as an off-white solid (32 mg, 36% yield). The reaction conditions (such as reagents ratio, temperature and reaction time) were modified as needed.

$^1$H NMR (500 MHz, Methanol-$d_4$) δ (ppm) 9.10 (s, 1H), 8.09 (s, 1H), 7.76 (s, 1H), 7.06 (m, 1H), 7.00 (m, 1H), 6.87-6.92 (m, 1H), 6.79 (t, 1H), 4.56 (s, 2H). LCMS [M+H]=363.2

Compound I-10

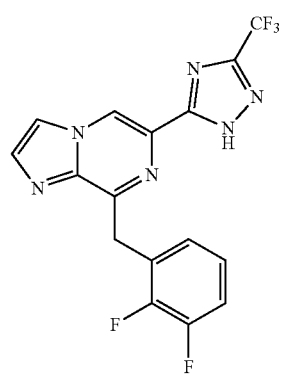

I-10

8-(2,3-Difluorobenzyl)-6-(3-(trifluoromethyl)-1H-1,2,4-triazol-5-yl)imidazo[1,2-a]pyrazine (I-10) was synthesized according to General Procedure B, with the exception that 2,2,2-trifluoroacetic anhydride was used as the acylating agent, as a white solid (110 mg, 39% yield). The reaction conditions (such as reagents ratio, temperature and reaction time) were modified as needed.

$^1$H NMR (500 MHz, Methanol-$d_4$) δ (ppm) 9.25 (s, 1H), 8.19 (s, 1H), 7.86 (s, 1H), 7.17-7.10 (m, 2H), 7.05 (m, 1H), 4.72 (s, 2H). LCMS [M+H]=381.2

Compound I-11

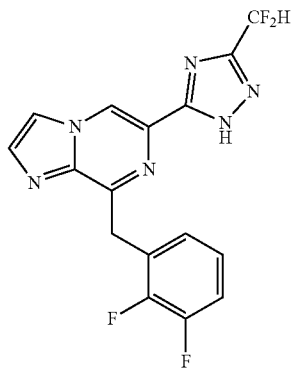

8-(2,3-Difluorobenzyl)-6-(3-(difluoromethyl)-1H-1,2,4-triazol-5-yl)imidazo[1,2-a]pyrazine (I-11) was synthesized according to General Procedure B, with the exception that 2,2-difluoroacetic anhydride was used as the acylating agent, as an off-white solid (55 mg, 25% yield). The reaction conditions (such as reagents ratio, temperature and reaction time) were modified as needed.

$^1$H NMR (500 MHz, Methanol-$d_4$) δ (ppm) 9.21 (s, 1H), 8.19 (s, 1H), 7.86 (s, 1H), 7.17-7.09 (m, 2H), 7.04 (m, 1H), 6.89 (t, 1H), 4.71 (s, 2H). LCMS [M+H]=363.2

Compound I-13

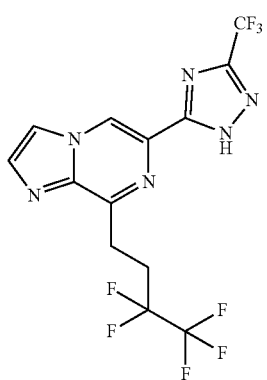

8-(3,3,4,4,4-Pentafluorobutyl)-6-(3-(trifluoromethyl)-1H-1,2,4-triazol-5-yl)imidazo[1,2-a]pyrazine (I-13) was synthesized according to General Procedure B, with the exception that 2,2,2-trifluoroacetic anhydride was used as the acylating agent, as a pale yellow solid (30 mg, 60% yield). The reaction conditions (such as reagents ratio, temperature and reaction time) were modified as needed.

$^1$H NMR (500 MHz, Methanol-$d_4$) δ (ppm) 9.24 (s, 1H), 8.19 (s, 1H), 7.86 (s, 1H), 3.59-3.66 (m, 2H), 2.93-3.07 (m, 2H). LCMS [M+H]=401.2

Compound I-12

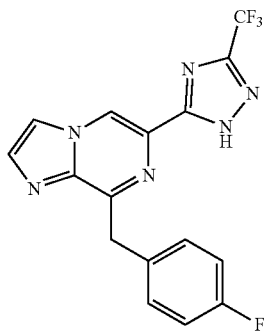

8-(4-Fluorobenzyl)-6-(3-(trifluoromethyl)-1H-1,2,4-triazol-5-yl)imidazo[1,2-a]pyrazine (I-12) was synthesized according to General Procedure B, with the exception that 2,2,2-trifluoroacetic anhydride was used as the acylating agent, as an off-white solid (75 mg, 84% yield). The reaction conditions (such as reagents ratio, temperature and reaction time) were modified as needed.

$^1$H NMR (500 MHz, DMSO-$d_6$) δ (ppm) 15.50 (s, 1H), 9.41 (s, 1H), 8.24 (s, 1H), 7.88 (s, 1H) 7.56 (dd, 2H), 7.10 (dd, 2H), 4.52 (s, 2H). LCMS [M+H]=363.2

Compound I-14

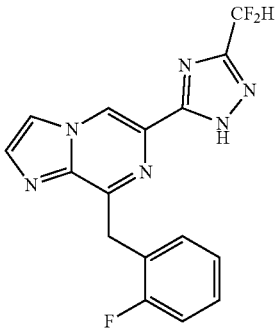

8-(2-Fluorobenzyl)-6-(3-(difluoromethyl)-1H-1,2,4-triazol-5-yl)imidazo[1,2-a]pyrazine (I-14) was synthesized according to General Procedure B, with the exception that 2,2-difluoroacetic anhydride was used as the acylating agent, as an off-white solid (46 mg, 56% yield). The reaction conditions (such as reagents ratio, temperature and reaction time) were modified as needed.

$^1$H NMR (500 MHz, Methanol-$d_4$) δ (ppm) 9.28 (s, 1H), 8.29 (s, 1H), 8.00 (s, 1H), 7.35 (t, 1H), 7.27 (d, 1H), 7.09 (m, 2H), 6.90 (m, 1H), 4.69 (s, 2H). LCMS [M+H]=345.2

Compound I-15

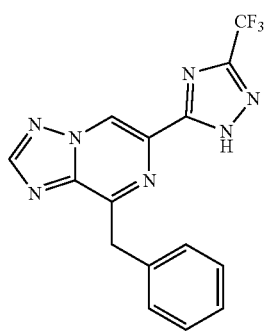

8-Benzyl-6-(3-(trifluoromethyl)-1H-1,2,4-triazol-5-yl)-[1,2,4]triazolo[1,5-a]pyrazine (I-15) was synthesized according to General Procedure B, with the exception that 2,2,2-trifluoroacetic anhydride was used as the acylating agent, as a white solid (60 mg, 33% yield). The reaction conditions (such as reagents ratio, temperature and reaction time) were modified as needed.

$^1$H NMR (500 MHz, DMSO-d$_6$) δ (ppm) 15.72 (s, 1H), 9.60 (s, 1H), 8.84 (s, 1H), 7.50 (d, 2H) 7.30 (app. t, 2H), 7.21 (t, 1H), 4.59 (s, 2H). LCMS [M+H]=346.2

Compound I-16

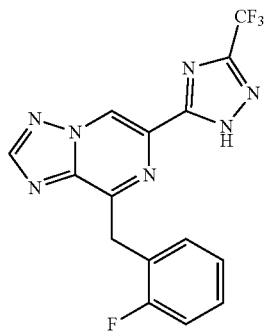

8-(2-Fluorobenzyl)-6-(3-(trifluoromethyl)-1H-1,2,4-triazol-5-yl)-[1,2,4]triazolo[1,5-a]pyrazine (I-16) was synthesized according to General Procedure B as an off-white solid (1.2 mg, 1.0% yield). The reaction conditions (such as reagents ratio, temperature and reaction time) were modified as needed.

$^1$H NMR (500 MHz, Methanol-d$_4$) δ (ppm) 9.51 (s, 1H), 8.65 (s, 1H), 7.43 (app. t, 1H), 7.27 (m, 1H), 7.10 (t, 2H), 4.74 (s, 2H). LCMS [M+H]=364.1

Compound I-18

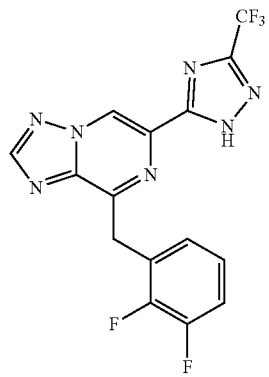

8-(2,3-Difluorobenzyl)-6-(3-(trifluoromethyl)-1H-1,2,4-triazol-5-yl)-[1,2,4]triazolo[1,5-a]pyrazine (I-18) was synthesized according to General Procedure B as a white solid (89 mg, 44% yield). The reaction conditions (such as reagents ratio, temperature and reaction time) were modified as needed.

$^1$H NMR (500 MHz, DMSO-d$_6$) δ (ppm) 15.7 (s, 1H), 9.64 (s, 1H), 8.84 (s, 1H), 7.30-7.35 (m, 1H), 7.27-7.30 (m, 1H), 7.12-7.15 (m, 1H), 4.69 (s, 2H).

LCMS [M+H]=382.2

Compound I-26

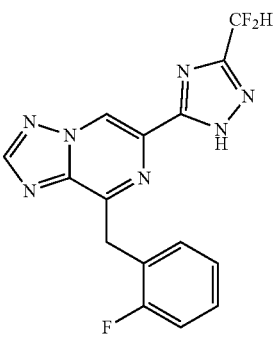

6-(3-(Difluoromethyl)-1H-1,2,4-triazol-5-yl)-8-(2-fluorobenzyl)-[1,2,4]triazolo[1,5-a]pyrazine (I-26) was synthesized according to General Procedure B, with the exception that 2,2-difluoroacetic anhydride was used as the acylating agent, as a white solid (180 mg, 88% yield). The reaction conditions (such as reagents ratio, temperature and reaction time) were modified as needed.

$^1$H NMR (500 MHz, DMSO-d$_6$) δ (ppm) 15.3 (s, 1H), 9.57 (s, 1H), 8.81 (s, 1H), 7.46 (app. t, 1H), 7.32-7.09 (m, 4H), 4.64 (s, 2H).

LCMS [M+H]=346.2

Compound I-27

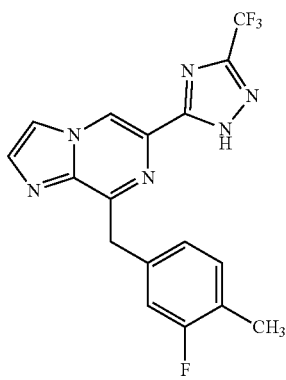

8-(3-Fluoro-4-methylbenzyl)-6-(3-(trifluoromethyl)-1H-1,2,4-triazol-5-yl)imidazo[1,2-a]pyrazine (I-27) was synthesized according to General Procedure B, with the exception that 2,2,2-trifluoroacetic anhydride was used as the acylating agent, as a pale yellow solid (110 mg, 61% yield). The reaction conditions (such as reagents ratio, temperature and reaction time) were modified as needed.

$^1$H NMR (500 MHz, DMSO-$d_6$) δ (ppm) 15.5 (s, 1H), 9.41 (s, 1H), 8.24 (s, 1H), 7.88 (s, 1H), 7.30 (d, 1H), 7.15-7.23 (m, 2H), 4.50 (s, 2H), 2.15 (s, 3H).

LCMS [M+H]=377.1

Compound I-28

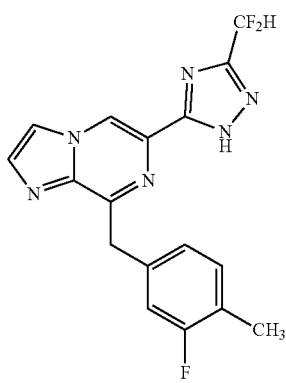

6-(3-(Difluoromethyl)-1H-1,2,4-triazol-5-yl)-8-(3-fluoro-4-methylbenzyl)imidazo[1,2-a]pyrazine (I-28) was synthesized according to General Procedure B, with the exception that 2,2-difluoroacetic anhydride was used as the acylating agent, as a pale yellow solid (130 mg, 76% yield). The reaction conditions (such as reagents ratio, temperature and reaction time) were modified as needed.

$^1$H NMR (500 MHz, DMSO-$d_6$) δ (ppm) 15.1 (s, 1H), 9.36 (s, 1H), 8.24 (s, 1H), 7.87 (s, 1H), 7.14-7.35 (m, 4H), 4.49 (s, 2H), 2.15 (s, 3H).

LCMS [M+H]=359.2

Compound I-29

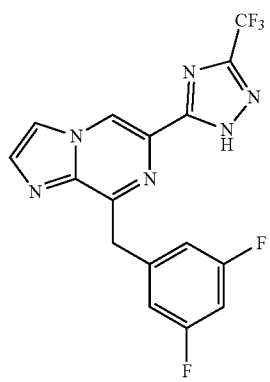

8-(3,5-Difluorobenzyl)-6-(3-(trifluoromethyl)-1H-1,2,4-triazol-5-yl)imidazo[1,2-a]pyrazine (I-29) was synthesized according to General Procedure B, with the exception that 2,2,2-trifluoroacetic anhydride was used as the acylating agent, as a pale yellow solid (150 mg, 68% yield). The reaction conditions (such as reagents ratio, temperature and reaction time) were modified as needed.

$^1$H NMR (500 MHz, DMSO-$d_6$) δ (ppm) 15.5 (s, 1H), 9.43 (s, 1H), 8.26 (s, 1H), 7.90 (s, 1H), 7.23 (d, 2H), 7.08 (t, 1H), 4.56 (s, 2H).

LCMS [M+H]=381.1

Compound I-30

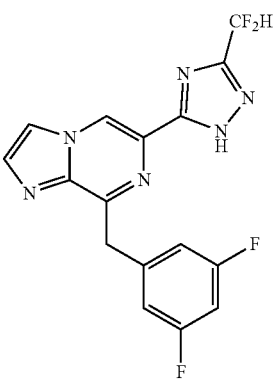

8-(3,5-Difluorobenzyl)-6-(3-(difluoromethyl)-1H-1,2,4-triazol-5-yl)imidazo[1,2-a]pyrazine (I-30) was synthesized according to General Procedure B, with the exception that 2,2-difluoroacetic anhydride was used as the acylating agent, as a pale yellow solid (140 mg, 70% yield). The reaction conditions (such as reagents ratio, temperature and reaction time) were modified as needed.

$^1$H NMR (500 MHz, DMSO-$d_6$) δ (ppm) 15.1 (s, 1H), 9.38 (s, 1H), 8.26 (s, 1H), 7.89 (s, 1H), 7.04-7.29 (m, 4H), 4.55 (s, 2H).

LCMS [M+H]=363.1

Compound I-31

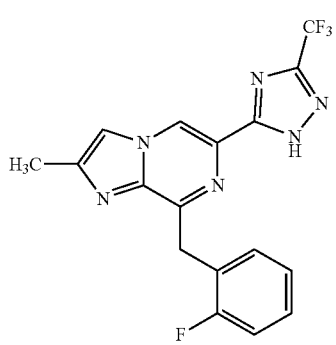

8-(2-Fluorobenzyl)-2-methyl-6-(3-(trifluoromethyl)-1H-1,2,4-triazol-5-yl)imidazo[1,2-a]pyrazine (I-31) was synthesized according to General Procedure B, with the exception that 2,2,2-trifluoroacetic anhydride was used as the acylating agent, as a white solid (35 mg, 55% yield). The reaction conditions (such as reagents, ratio, temperature and reaction time) were modified as needed.

$^1$H NMR (500 MHz, CDCl$_3$) δ (ppm) 11.6 (br. s, 1H), 8.88 (s, 1H), 7.61 (s, 1H), 7.39 (app. t, 1H), 7.26-7.32 (m, 1H), 7.09-7.15 (m, 2H), 4.69 (s, 2H), 2.60 (s, 3H).

LCMS [M+H]=377.3

Compound I-32

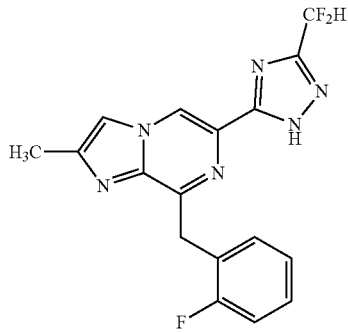

6-(3-(Difluoromethyl)-1H-1,2,4-triazol-5-yl)-8-(2-fluorobenzyl)-2-methylimidazo[1,2-a]pyrazine (I-32) was synthesized according to General Procedure B, with the exception that 2,2-difluoroacetic anhydride was used as the acylating agent, as a white solid (44 mg, 85% yield). The reaction conditions (such as reagents, ratio, temperature and reaction time) were modified as needed.

$^1$H NMR (500 MHz, CDCl$_3$) δ (ppm) 11.5 (br. s, 1H), 8.89 (s, 1H), 7.61 (s, 1H), 7.38 (app. t, 1H), 7.26-7.34 (m, 1H), 7.08-7.14 (m, 2H), 6.77 (t, 1H), 4.69 (s, 2H), 2.60 (s, 3H).

LCMS [M+H]=359.2

Compound I-33

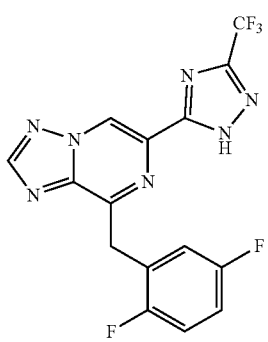

8-(2,5-Difluorobenzyl)-6-(3-(trifluoromethyl)-1H-1,2,4-triazol-5-yl)-[1,2,4]triazolo[1,5-a]pyrazine (I-33) was synthesized according to General Procedure B, with the exception that 2,2,2-trifluoroacetic anhydride was used as the acylating agent, as a white solid (72 mg, 41% yield). The reaction conditions (such as reagents ratio, temperature and reaction time) were modified as needed.

$^1$H NMR (500 MHz, Methanol-d$_4$) δ (ppm) 9.51 (s, 1H), 8.66 (s, 1H), 7.20-7.29 (m, 1H), 7.06-7.15 (m, 1H), 7.01 (m, 1H), 4.72 (s, 2H).

LCMS [M+H]=382.2

Compound I-34

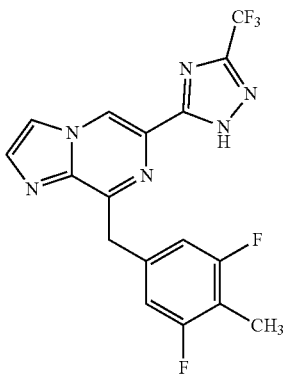

8-(3,5-Difluoro-4-methylbenzyl)-6-(3-(trifluoromethyl)-1H-1,2,4-triazol-5-yl)imidazo[1,2-a]pyrazine (I-34) was synthesized according to General Procedure B, with the exception that 2,2,2-trifluoroacetic anhydride was used as the acylating agent, as a white solid (81 mg, 65% yield). The reaction conditions (such as reagents ratio, temperature and reaction time) were modified as needed.

$^1$H NMR (500 MHz, CDCl$_3$) δ (ppm) 11.9 (br. s, 1H), 9.02 (s, 1H), 7.94 (s, 1H), 7.85 (s, 1H), 6.95 (d, 2H), 4.58 (s, 2H), 2.14 (s, 3H).

LCMS [M+H]=395.2

Compound I-35

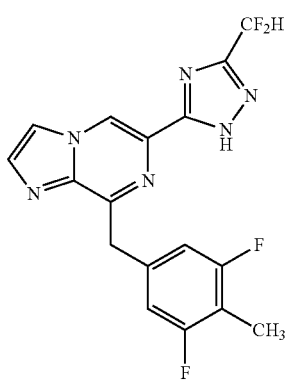

8-(3,5-Difluoro-4-methylbenzyl)-6-(3-(difluoromethyl)-1H-1,2,4-triazol-5-yl)imidazo[1,2-a]pyrazine (I-35) was synthesized according to General Procedure B, with the exception that 2,2-difluoroacetic anhydride was used as the acylating agent, as a white solid (83 mg, 62% yield). The reaction conditions (such as reagents ratio, temperature and reaction time) were modified as needed.

NMR (500 MHz, CDCl$_3$) δ (ppm) 11.7 (br. s, 1H), 9.02 (s, 1H), 7.92 (s, 1H), 7.83 (s, 1H), 6.98 (d, 2H), 6.81 (t, 1H), 4.58 (s, 2H), 2.15 (s, 3H).

LCMS [M+H]=377.2

Compound I-36

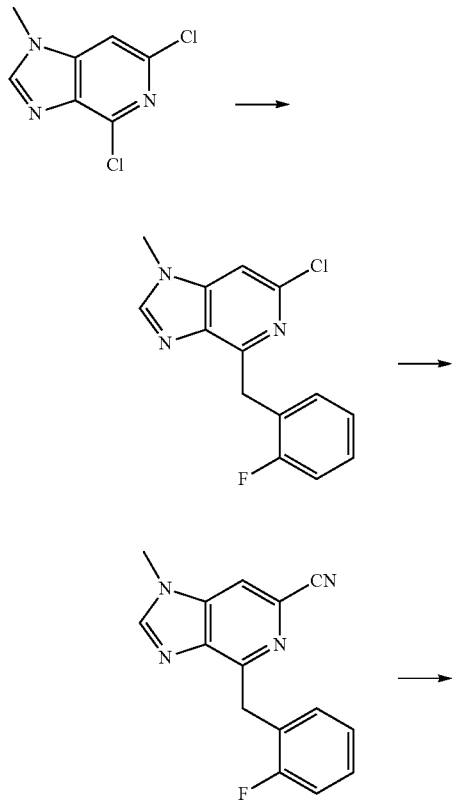

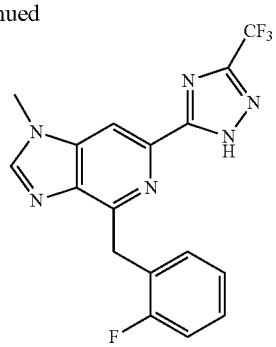

Compound I-36

4-(2-Fluorobenzyl)-1-methyl-6-(3-(trifluoromethyl)-1H-1,2,4-triazol-5-yl)-1H-imidazo[4,5-c]pyridine (I-36)

The title compound was synthesized in 3 steps.

Step 1: Synthesis of 6-chloro-4-(2-fluorobenzyl)-1-methyl-1H-imidazo[4,5-c]pyridine To a mixture containing bis(triphenylphosphine)palladium(II) dichloride (290 mg, 0.42 mmol), lithium chloride (350 mg, 8.3 mmol) and 4,6-dichloro-1-methyl-1H-imidazo[4,5-c]pyridine (840 mg, 4.2 mmol) in THF (2.0 mL) at ambient temperature was added (2-fluorobenzyl)zinc(II) chloride (0.5 M solution in THF, 10 mL, 5.0 mmol). The mixture was stirred at ambient temperature for 24 hours. The mixture was taken up in EtOAc (100 mL) and water (100 mL). The organic layer was dried over Na$_2$SO$_4$, filtered and evaporated to give an oil. The crude material was purified using silica gel chromatography (0-80% EtOAc/hexanes gradient) to give 6-chloro-4-(2-fluorobenzyl)-1-methyl-1H-imidazo[4,5-c]pyridine (1.0 g, 70% yield) as a yellow solid.

$^1$H NMR (500 MHZ, CDCl$_3$) δ (ppm) 7.87 (s, 1H), 7.63-7.79 (m, 1H), 7.26 (br. s, 1H), 7.12-7.19 (m, 1H), 6.96-7.07 (m, 2H), 4.60 (br. s, 2H), 3.80 (s, 3H).

Step 2: Synthesis of 4-(2-fluorobenzyl)-1-methyl-1H-imidazo[4,5-c]pyridine-6-carbonitrile A mixture containing zinc cyanide (850 mg, 7.3 mmol), tetrakis(triphenylphosphine)palladium(0) (420 mg, 0.36 mmol) and 6-chloro-4-(2-fluorobenzyl)-1-methyl-1H-imidazo[4,5-c]pyridine (1.0 g, 3.6 mmol) in DMF (18 mL) was heated to 100° C. for 24 hours. The reaction mixture was quenched with water (10 mL) and EtOAc (20 mL) and filtered through a pad of Celite. The filtrate was extracted with EtOAc (100 mL). The organic layer was dried over Na$_2$SO$_4$, filtered and evaporated to give a solid. The crude material was purified using silica gel chromatography (0-100% EtOAc/hexanes gradient) to give impure 4-(2-fluorobenzyl)-1-methyl-1H-imidazo[4,5-c]pyridine-6-carbonitrile (130 mg) as a white solid.

$^1$H NMR (500 MHz, CDCl$_3$) δ (ppm) 8.08 (s, 1H), 7.72 (s, 1H), 7.65-7.71 (m, 1H), 7.32 (m, 1H), 6.98-7.09 (m, 2H), 4.64 (s, 2H), 3.92 (s, 3H).

Step 3: Synthesis of 4-(2-fluorobenzyl)-1-methyl-6-(3-(trifluoromethyl)-1H-1,2,4-triazol-5-yl)-1H-imidazo[4,5-c]pyridine (I-36)

A mixture containing anhydrous hydrazine (0.092 mL, 2.9 mmol) and 4-(2-fluorobenzyl)-1-methyl-1H-imidazo[4,5-c]

pyridine-6-carbonitrile (130 mg) in MeOH (2.5 mL) was stirred at ambient temperature for 24 hours. The mixture was concentrated in vacuo and dried azeotropically with MeOH and benzene. The resulting mixture was dissolved in DCM (10 mL) and treated with pyridine (0.24 mL, 2.9 mmol) and 2,2,2-trifluoroacetic anhydride (0.21 mL, 1.5 mmol). After stirring at ambient temperature for 2 hours, the reaction was diluted in EtOAc (100 mL) and washed with saturated NaHCO$_3$ solution (50 mL). The organic layer was dried over Na$_2$SO$_4$, filtered and evaporated to give an oil. The crude material was purified by preparative HPLC to afford 4-(2-fluorobenzyl)-1-methyl-6-(3-(trifluoromethyl)-1H-1,2,4-triazol-5-yl)-1H-imidazo[4,5-c]pyridine (6.3 mg, 0.47% yield over two steps) as a light brown solid.

$^1$H NMR (500 MHz, Methanol-d$_4$) δ (ppm) 8.57 (s, 1H), 8.41 (s, 1H), 7.18-7.28 (m, 2H), 6.97-7.12 (m, 2H), 4.67 (s, 2H), 4.04 (s, 3H).

LCMS [M+H]=377.1

8-(2-Fluorobenzyl)-6-(3-(trifluoromethyl)-1H-1,2,4-triazol-5-yl)-[1,2,4]triazolo[4,3-a]pyrazine (I-72)

The title compound was synthesized in 3 steps.

Step 1: Synthesis of 6-bromo-8-(2-fluorobenzyl)-[1,2,4]triazolo[4,3-a]pyrazine

A solution of bis(triphenylphosphine)palladium(II) dichloride (62 mg, 0.088 mmol) and 6-bromo-8-chloro-[1,2,4]triazolo[4,3-a]pyrazine (410 mg, 1.8 mmol) in THF (5.9 mL) at ambient temperature was purged with argon for 5 min and treated with (2-fluorobenzyl)zinc(II) chloride (0.5 M solution in THF, 5.3 mL, 2.6 mmol). The mixture was stirred at 60° C. for 24 hours. The reaction was quenched with saturated NH$_4$Cl solution (15 mL) and extracted with EtOAc (4×50 mL). The combined organic layers were washed with brine, dried over Na$_2$SO$_4$, filtered and concentrated in vacuo. The crude material was purified using reverse phase HPLC (5-95% acetonitrile/water gradient with 0.1% formic acid) to give 6-bromo-8-(2-fluorobenzyl)-[1,2,4]triazolo[4,3-a]pyrazine (110 mg, 43% pure, contaminated with an undesired regioisomer, 9.1% yield) as a brown solid.

Step 2: Synthesis of 8-(2-fluorobenzyl)-[1,2,4]triazolo[4,3-a]pyrazine-6-carbonitrile A solid mixture containing zinc dust (4.7 mg, 0.072 mmol), zinc cyanide (63 mg, 0.54 mmol), [1,1'-bis(diphenylphosphino)ferrocene]dichloropalladium(II) dichloromethane adduct (29 mg, 0.036 mmol) and 6-bromo-8-(2-fluorobenzyl)-[1,2,4]triazolo[4,3-a]pyrazine (110 mg, 43% pure, 0.15 mmol of desired regioisomer and 0.21 mmol of undesired regioisomer) was purged with nitrogen for 15 min and then dissolved in DMF (3 mL). The reaction was heated to 120° C. for 8 hours. The resultant mixture was partitioned between water (10 mL), brine (10 mL) and EtOAc (20 mL). The aqueous layer was extracted with EtOAc (20 mL). The combined organic layers were dried over Na$_2$SO$_4$, filtered and concentrated in vacuo. The crude material was purified using silica gel chromatography (20-100% EtOAc/hexanes gradient) to give 8-(2-fluorobenzyl)-[1,2,4]triazolo[4,3-a]pyrazine-6-carbonitrile (24 mg, 61% yield) as a light tan solid.

Step 3: Synthesis of 8-(2-fluorobenzyl)-6-(3-(trifluoromethyl)-1H-1,2,4-triazol-5-yl)-[1,2,4]triazolo[4,3-a]pyrazine (I-72)

A suspension of 8-(2-fluorobenzyl)-[1,2,4]triazolo[4,3-a]pyrazine-6-carbonitrile (24 mg, 0.094 mmol) in anhydrous methanol (1.5 mL) was treated with sodium methoxide (0.50 N solution in methanol, 19 μL, 9.4 μmol). After 3.5 hours, anhydrous hydrazine (18 μL, 0.57 mmol) was added and the reaction was stirred at ambient temperature for 23 hours. The resultant mixture was concentrated, dried in vacuo and then re-dissolved in DCM/THF (2 mL, 3:1 ratio). 2,2,2-Trifluoroacetic anhydride (21 μL, 0.15 mmol). After 40 minutes, the mixture was concentrated, dissolved in EtOH (2 mL) and acetic acid (0.2 mL) and heated at 90° C. for 15 hours. The resultant solution was poured into water (10 mL), neutralized to pH 6 with saturated NaHCO$_3$ solution and extracted with EtOAc (2×20 mL). The combined organic layers were dried over Na$_2$SO$_4$, filtered and concentrated in vacuo. The crude material was purified by silica gel chromatography (20-90% EtOAc/hexanes gradient) to afford 8-(2-fluorobenzyl)-6-(3-(trifluoromethyl)-1H-1,2,4-triazol-5-yl)-[1,2,4]triazolo[4,3-a]pyrazine (1.4 mg, 4.1% yield) as a light yellow film.

$^1$H NMR (500 MHz, Methanol-d$_4$) δ (ppm) 9.43 (s, 1H), 9.22 (s, 1H), 7.47 (app. t, 1H), 7.29 (m, 1H), 7.13-7.08 (m, 2H), 4.76 (s, 2H).

LCMS [M+H]=364.2

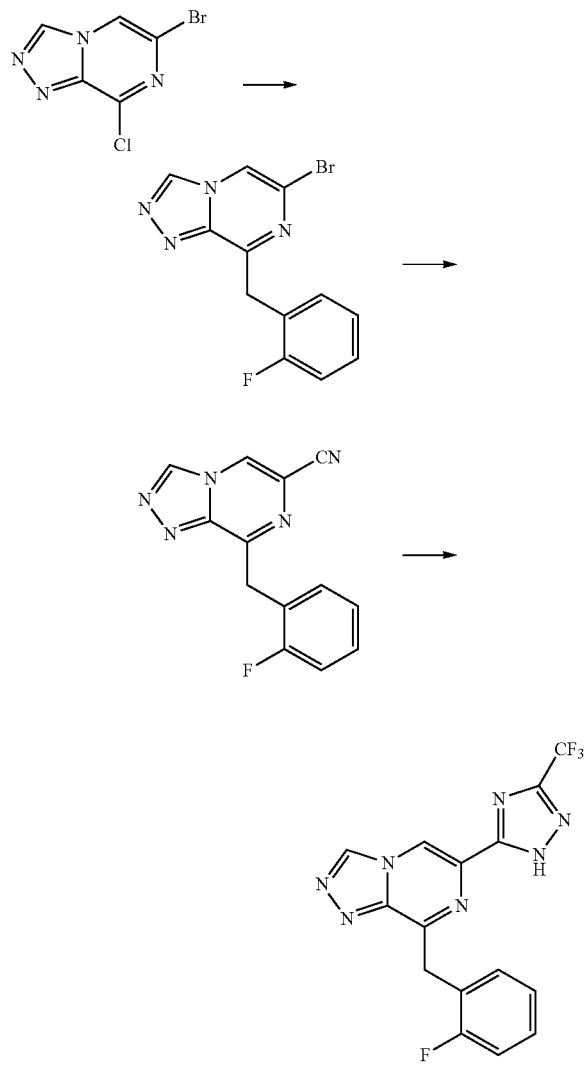

Compound I-72

Compound I-37

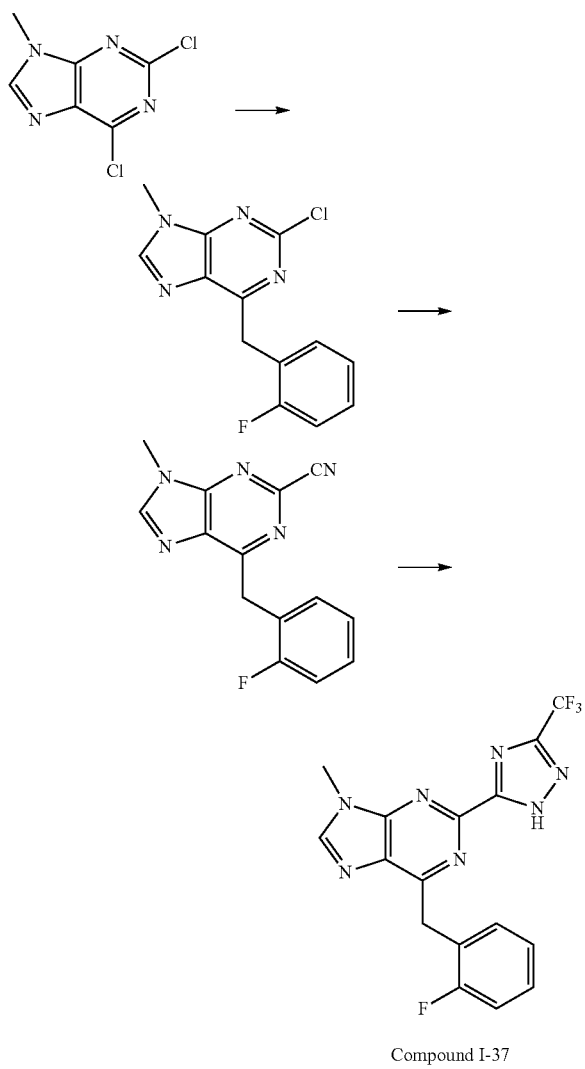

6-(2-Fluorobenzyl)-9-methyl-2-(3-(trifluoromethyl)-
1H-1,2,4-triazol-5-yl)-9H-purine (I-37)

The title compound was synthesized in 3 steps.

Step 1: Synthesis of
2-chloro-6-(2-fluorobenzyl)-9-methyl-9H-purine

To a mixture containing bis(triphenylphosphine)palladium(II) dichloride (240 mg, 0.34 mmol), lithium chloride (290 mg, 6.8 mmol) and 2,6-dichloro-9-methyl-9H-purine (690 mg, 3.4 mmol) in THF (17 mL) at ambient temperature was added 2-fluorobenzylzinc(II) chloride (0.5 M solution in THF, 7.5 mL, 3.7 mmol). The reaction was stirred at ambient temperature for 24 hours. The resultant mixture was diluted with EtOAc (100 mL) and water (100 mL). The organic layer was dried over Na$_2$SO$_4$, filtered and evaporated to give an oil. The crude material was purified using silica gel chromatography (0-50% EtOAc/hexanes gradient) to afford 2-chloro-6-(2-fluorobenzyl)-9-methyl-9H-purine (620 mg, 66% yield) as a white solid.

$^1$H NMR (500 MHz, CDCl$_3$) δ (ppm) 8.02 (s, 1H), 7.37 (m, 1H), 7.18-7.25 (m, 1H), 7.02-7.10 (m, 2H), 4.54 (s, 2H), 3.88 (s, 3H).

Step 2: Synthesis of 6-(2-fluorobenzyl)-9-methyl-
9H-purine-2-carbonitrile

A mixture containing zinc cyanide (530 mg, 4.5 mmol), tetrakis(triphenylphosphine)palladium(0) (260 mg, 0.22 mmol) and 2-chloro-6-(2-fluorobenzyl)-9-methyl-9H-purine (620 mg, 2.2 mmol) in DMF (12 mL) was heated to 100° C. for 24 hours. The mixture was quenched with water (50 mL) and EtOAc (10 mL) and filtered through a pad of Celite. The filtrate was extracted with EtOAc (100 mL). The organic layer was dried over Na$_2$SO$_4$, filtered and evaporated to give an oil. The crude material was purified using silica gel chromatography (0-100% EtOAc/hexanes gradient) to afford 6-(2-fluorobenzyl)-9-methyl-9H-purine-2-carbonitrile (490 mg, 82% yield) as a white solid.

$^1$H NMR (500 MHz, CDCl$_3$) δ (ppm) 8.22 (s, 1H), 7.39 (t, 1H), 7.20-7.26 (m, 1H), 7.01-7.12 (m, 2H), 4.61 (s, 2H), 3.95 (s, 3H).

Step 3: Synthesis of 6-(2-fluorobenzyl)-9-methyl-2-
(3-(trifluoromethyl)-1H-1,2,4-triazol-5-yl)-9H-purine (I-37)

A mixture containing anhydrous hydrazine (0.090 mL, 2.9 mmol) and 6-(2-fluorobenzyl)-9-methyl-9H-purine-2-carbonitrile (130 mg, 0.48 mmol) in MeOH (2.4 mL) was heated to 60° C. for 2 hours. The mixture was concentrated in vacuo and dried azeotropically with MeOH and benzene. The resulting solid was dissolved in DCM (5.0 mL) and treated with pyridine (0.23 mL, 2.9 mmol) and 2,2,2-trifluoroacetic anhydride (0.20 mL, 1.4 mmol). After stirring at ambient temperature for 24 hours, the reaction was diluted with DCM (100 mL) and washed with water (100 mL). The organic layer was dried over Na$_2$SO$_4$, filtered and evaporated to give an oil. The crude material was purified using silica gel chromatography (0-50% EtOAc/hexanes gradient) to recover the 2,2,2-trifluoro-N'-((6-(2-fluorobenzyl)-9-methyl-9H-purin-2-yl)(imino)methyl)acetohydrazide intermediate. The solid was combined with MeOH (1.0 mL) and a few drops of acetic acid. The resultant mixture was heated at 120° C. for 1 hour in a microwave. The mixture was cooled to ambient and concentrated in vacuo to give 6-(2-fluorobenzyl)-9-methyl-2-(3-(trifluoromethyl)-1H-1,2,4-triazol-5-yl)-9H-purine (25 mg, 14% yield) as a white solid.

$^1$H NMR (500 MHz, Methanol-d$_4$) δ (ppm) 8.50-8.54 (m, 1H), 7.28-7.41 (m, 1H), 7.14-7.27 (m, 1H), 6.97-7.12 (m, 2H), 4.63 (s, 2H), 4.01 (s, 3H).
LCMS [M+H]=378.1

Compound I-38 and Compound I-39

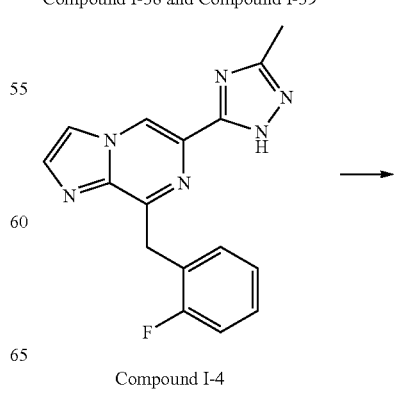

Compound I-4

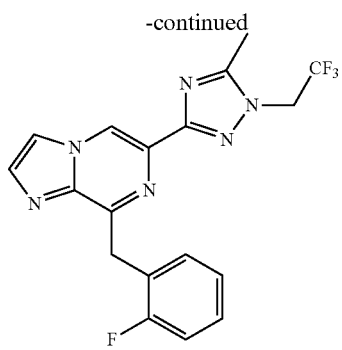

Compound I-38

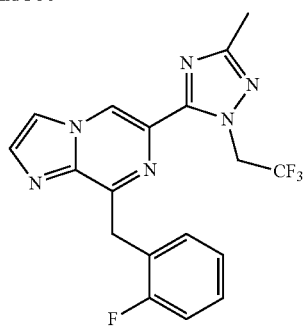

Compound I-39

General Procedure C: 8-(2-fluorobenzyl)-6-(5-methyl-1-(2,2,2-trifluoroethyl)-1H-1,2,4-triazol-3-yl)imidazo[1,2-a]pyrazine (I-38) and 8-(2-fluorobenzyl)-6-(3-methyl-1-(2,2,2-trifluoroethyl)-1H-1,2,4-triazol-5-yl)imidazo[1,2-a]pyrazine (I-39)

To a suspension of 8-(2-fluorobenzyl)-6-(3-methyl-1H-1,2,4-triazol-5-yl)imidazo[1,2-a]pyrazine (69 mg, 0.22 mmol) and potassium carbonate (68 mg, 0.49 mmol) in DMF (3.0 mL) was added 2,2,2-trifluoroethyl trifluoromethanesulfonate (0.050 mL, 0.31 mmol). After stirring at ambient temperature for 15 hours, the reaction mixture was poured into a mixture of water and brine (1:2, 20 mL) and extracted with DCM (2×20 mL). The combined organic layers were dried over Na₂SO₄, filtered and concentrated. The crude material was purified using silica gel chromatography (20-100% EtOAc/hexanes gradient) to isolate 8-(2-fluorobenzyl)-6-(5-methyl-1-(2,2,2-trifluoroethyl)-1H-1,2,4-triazol-3-yl)imidazo[1,2-a]pyrazine (I-38) (18 mg, 21% yield) as a pale yellow solid and 8-(2-fluorobenzyl)-6-(3-methyl-1-(2,2,2-trifluoroethyl)-1H-1,2,4-triazol-5-yl)imidazo[1,2-a]pyrazine (I-39) (52 mg, 60% yield) as a pale yellow solid. The chemical structures were assigned with the aid of ¹H NMR nOe experiments. In this case, a potential third regioisomer (usually minor) was not observed.

Compound I-38:

¹H NMR (500 MHz, DMSO-d₆) δ (ppm) 9.19 (s, 1H), 8.23 (s, 1H), 7.80 (s, 1H), 7.34 (app. t, 1H), 7.27 (m, 1H), 7.17 (app. t, 1H), 7.08 (app. t, 1H), 5.34 (q, 2H), 4.56 (s, 2H), 2.53 (s, 3H).

LCMS [M+H]=391.2

Compound I-39:

¹H NMR (500 MHz, DMSO-d₆) δ (ppm) 9.39 (s, 1H), 8.30 (s, 1H), 7.93 (s, 1H), 7.48 (app. t, 1H), 7.35 (m, 1H), 7.21-7.15 (m, 2H), 5.41 (q, 2H), 4.64 (s, 2H), 2.31 (s, 3H).

LCMS [M+H]=391.2

Compound I-41 and Compound I-42

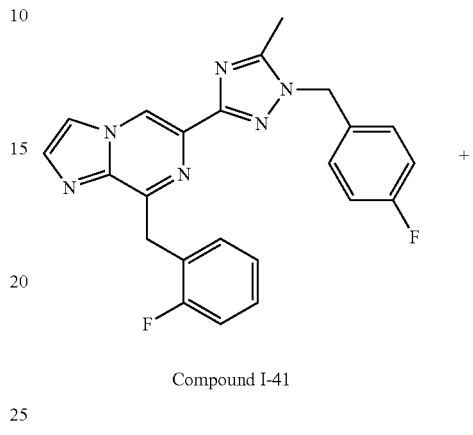

Compound I-41

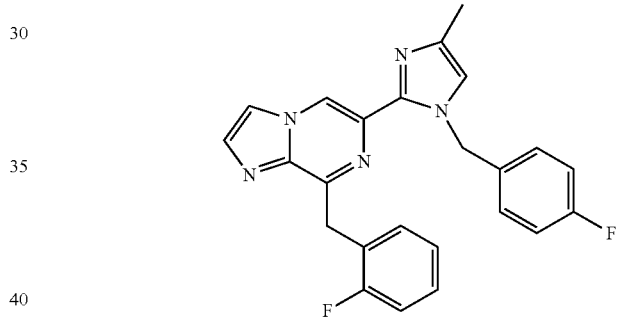

Compound I-42

8-(2-Fluorobenzyl)-6-(1-(4-fluorobenzyl)-5-methyl-1H-1,2,4-triazol-3-yl)imidazo[1,2-a]pyrazine (I-41) and 8-(2-fluorobenzyl)-6-(1-(4-fluorobenzyl)-3-methyl-1H-1,2,4-triazol-5-yl)imidazo[1,2-a]pyrazine (I-42) were synthesized according to General Procedure C, with the exception that 1-(bromomethyl)-4-fluorobenzene was used as the alkylating agent, as solids (I-41: 1.3 mg, 3.9% yield and I-42: 2.9 mg, 8.6% yield). The reaction conditions (such as reagents ratio, temperature and reaction time) were modified as needed.

Compound I-41:

¹H NMR (500 MHz, DMSO-d₆) δ (ppm) 9.15 (s, 1H), 8.21 (s, 1H), 7.79 (s, 1H), 7.32 (m, 3H), 7.21 (m, 4H), 7.08 (app. t, 1H), 5.44 (s, 2H), 4.54 (s, 2H), 2.48 (s, 3H).

LCMS [M+H]=417.3

Compound I-42:

¹H NMR (500 MHz, DMSO-d₆) δ (ppm) 9.34 (s, 1H), 8.29 (s, 1H), 7.91 (s, 1H), 7.37 (app. t, 1H), 7.20 (m, 1H), 7.03 (m, 6H), 5.61 (s, 2H), 4.63 (s, 2H), 2.25 (s, 3H).

LCMS [M+H]=417.4

Compound I-47

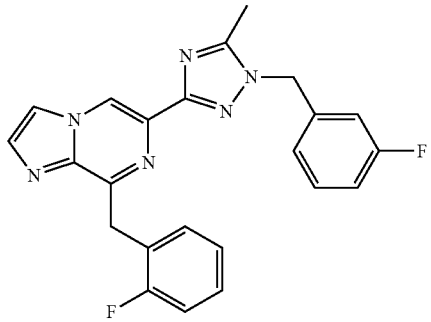

Compound I-47

8-(2-Fluorobenzyl)-6-(1-(3-fluorobenzyl)-5-methyl-1H-1,2,4-triazol-3-yl)imidazo[1,2-a]pyrazine (I-47) was synthesized according to General Procedure C, with the exception that 1-(bromomethyl)-3-fluorobenzene was used as the alkylating agent, as a solid (4.2 mg, 12% yield). The other regioisomers were not isolated. The reaction conditions (such as reagents ratio, temperature and reaction time) were modified as needed.

$^1$H NMR (500 MHz, Methanol-$d_4$) δ (ppm) 9.04 (s, 1H), 8.11 (s, 1H), 7.78 (s, 1H), 7.38 (m, 1H), 7.23 (m, 2H), 7.06 (m, 5H), 5.47 (s, 2H), 4.65 (s, 2H), 2.51 (s, 3H).

LCMS [M+H]=417.4

Compound I-48

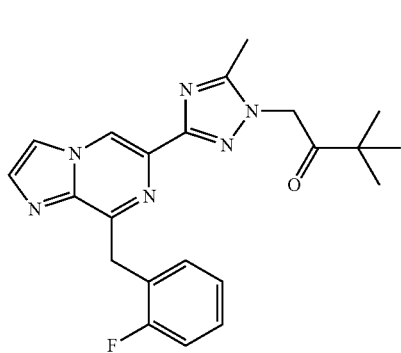

Compound I-48

1-(3-(8-(2-Fluorobenzyl)imidazo[1,2-a]pyrazin-6-yl)-5-methyl-1H-1,2,4-triazol-1-yl)-3,3-dimethylbutan-2-one (I-48) was synthesized according to General Procedure C, with the exception that 1-bromo-3,3-dimethylbutan-2-one was used as the alkylating agent, as a solid (7.6 mg, 23% yield). The other regioisomers were not isolated. The reaction conditions (such as reagents ratio, temperature and reaction time) were modified as needed.

$^1$H NMR (500 MHz, DMSO-$d_6$) δ (ppm) 9.15 (s, 1H), 8.22 (s, 1H), 7.79 (s, 1H), 7.32 (app. t, 1H), 7.25 (m, 1H), 7.17 (app. t, 1H), 7.08 (app. t, 1H), 5.54 (s, 2H), 4.54 (s, 2H), 2.31 (s, 3H), 1.22 (s, 9H).

LCMS [M+H]=407.4

Compound I-50

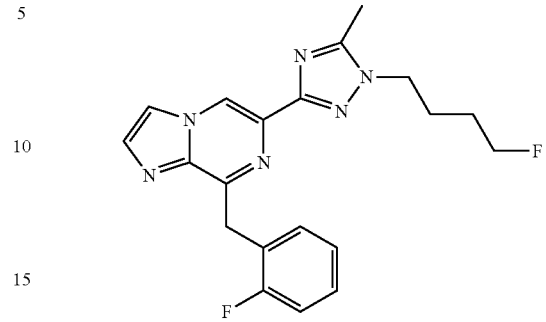

Compound I-50

8-(2-Fluorobenzyl)-6-(1-(4-fluorobutyl)-5-methyl-1H-1,2,4-triazol-3-yl)imidazo[1,2-a]pyrazine (I-50) was synthesized according to General Procedure C, with the exception that 1-bromo-4-fluorobutane was used as the alkylating agent, as a solid (0.9 mg, 2.8% yield). The other regioisomers were not isolated. The reaction conditions (such as reagents ratio, temperature and reaction time) were modified as needed.

$^1$H NMR (500 MHz, Methanol-$d_4$) δ (ppm) 9.03 (s, 1H), 8.14 (s, 1H), 7.81 (s, 1H), 7.26 (m, 2H), 7.06 (m, 2H), 4.67 (s, 2H), 4.55 (t, 1H), 4.45 (t, 1H), 4.27 (t, 2H), 2.56 (s, 3H), 2.05 (m, 2H), 1.77 (m, 2H).

LCMS [M+H]=383.3

Compound I-51

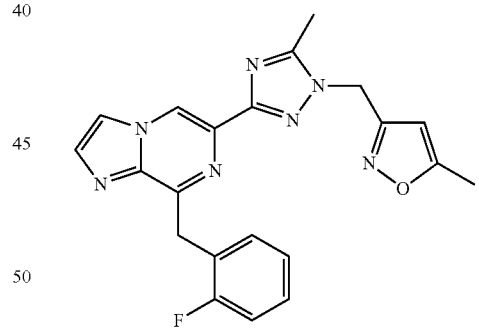

Compound I-51

3-((3-(8-(2-Fluorobenzyl)imidazo[1,2-a]pyrazin-6-yl)-5-methyl-1H-1,2,4-triazol-1-yl)methyl)-5-methylisoxazole (I-51) was synthesized according to General Procedure C, with the exception that 3-(bromomethyl)-5-methylisoxazole was used as the alkylating agent, as a solid (4.1 mg, 13% yield). The other regioisomers were not isolated. The reaction conditions (such as reagents ratio, temperature and reaction time) were modified as needed.

$^1$H NMR (500 MHz, Methanol-$d_4$) δ (ppm) 9.05 (s, 1H), 8.13 (s, 1H), 7.80 (s, 1H), 7.26 (m, 2H), 7.08 (m, 1H), 7.04 (m, 1H), 6.20 (s, 1H), 5.50 (s, 2H), 4.66 (s, 2H), 2.58 (s, 3H), 2.42 (s, 3H).

LCMS [M+H]=404.3

Compound I-53

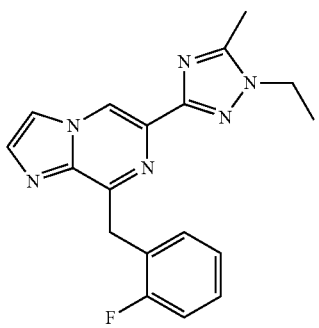

6-(1-Ethyl-5-methyl-1H-1,2,4-triazol-3-yl)-8-(2-fluorobenzyl)imidazo[1,2-a]pyrazine (I-53) was synthesized according to General Procedure C, with the exception that iodoethane was used as the alkylating agent, as a solid (3.0 mg, 11% yield). The other regioisomers were not isolated. The reaction conditions (such as reagents ratio, temperature and reaction time) were modified as needed.

$^1$H NMR (500 MHz, Methanol-$d_4$) δ (ppm) 9.02 (s, 1H), 8.13 (s, 1H), 7.81 (s, 1H), 7.25 (m, 2H), 7.08 (m, 1H), 7.04 (m, 1H), 4.67 (s, 2H), 4.26 (q, 2H), 2.56 (s, 3H), 1.50 (t, 3H).

LCMS [M+H]=337.3

Compound I-54

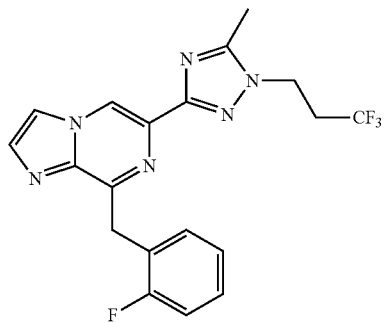

8-(2-Fluorobenzyl)-6-(5-methyl-1-(3,3,3-trifluoropropyl)-1H-1,2,4-triazol-3-yl)imidazo[1,2-a]pyrazine (I-54) was synthesized according to General Procedure C, with the exception that 3-bromo-1,1,1-trifluoropropane was used as the alkylating agent, as a solid (2.9 mg, 8.8% yield). The other regioisomers were not isolated. The reaction conditions (such as reagents ratio, temperature and reaction time) were modified as needed.

$^1$H NMR (500 MHz, Methanol-$d_4$) δ (ppm) 9.06 (s, 1H), 8.14 (s, 1H), 7.81 (s, 1H), 7.25 (m, 2H), 7.09 (m, 1H), 7.04 (m, 1H), 4.67 (s, 2H), 4.49 (t, 2H), 2.94 (m, 2H), 2.57 (s, 3H).

LCMS [M+H]=405.3

Compound I-56

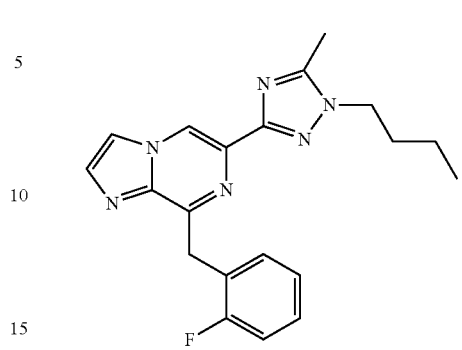

6-(1-Butyl-5-methyl-1H-1,2,4-triazol-3-yl)-8-(2-fluorobenzyl)imidazo[1,2-a]pyrazine (I-56) was synthesized according to General Procedure C, with the exception that 1-bromobutane was used as the alkylating agent, as a solid (2.0 mg, 6.8% yield). The other regioisomers were not isolated. The reaction conditions (such as reagents ratio, temperature and reaction time) were modified as needed.

$^1$H NMR (500 MHz, Methanol-$d_4$) δ (ppm) 9.02 (s, 1H), 8.14 (s, 1H), 7.80 (s, 1H), 7.26 (m, 2H), 7.08 (m, 1H), 7.04 (m, 1H), 4.67 (s, 2H), 4.22 (t, 2H), 2.55 (s, 3H), 1.90 (app. quin, 2H), 1.41 (m, 2H), 1.00 (t, 3H).

LCMS [M+H]=365.3

Compound I-57

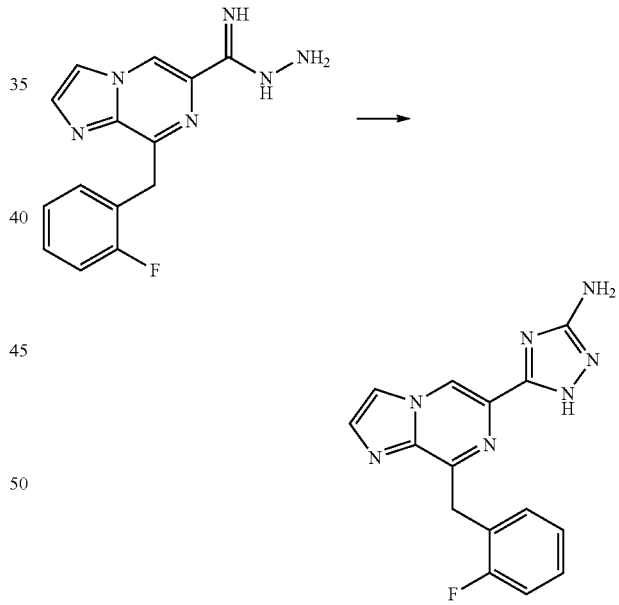

5-(8-(2-Fluorobenzyl)imidazo[1,2-a]pyrazin-6-yl)-1H-1,2,4-triazol-3-amine (I-57)

A suspension of S-methylisothiourea hemisulfate salt (510 mg, 1.8 mmol), 8-(2-fluorobenzyl)imidazo[1,2-a]pyrazine-6-carboximidhydrazide (520 mg, 1.8 mmol) and sodium hydroxide (73 mg, 1.8 mmol) in water (8 mL) was heated to 120° C. for 60 minutes in the microwave. The reaction mixture was filtered using methanol as the eluent, and the resulting filtrate was concentrated to afford the crude product. This material was purified by reverse phase HPLC (12-37% acetonitrile/water gradient with 0.1% trifluoroacetic acid) to afford an orange oil which was a mixture of 2 compounds (360 mg). This product mixture was used in subsequent reactions without further purification.

A small sample of this material was further purified on reverse phase HPLC (10-55% acetonitrile/water gradient with 0.1% formic acid) to afford 5-(8-(2-fluorobenzyl)imidazo[1,2-a]pyrazin-6-yl)-1H-1,2,4-triazol-3-amine (I-57) (3.0 mg) as a white solid.

$^1$H NMR (500 MHz, DMSO-d$_6$) δ (ppm) 12.1 (br. s, 1H), 8.92 (br. s, 1H), 8.21 (s, 1H), 7.77 (s, 1H), 7.35-7.40 (m, 1H), 7.25-7.29 (m, 1H), 7.15-7.19 (m, 1H), 7.06-7.11 (m, 1H), 6.09 (s, 2H), 4.53 (s, 2H).

LCMS [M+H]=310.1

Compound I-58

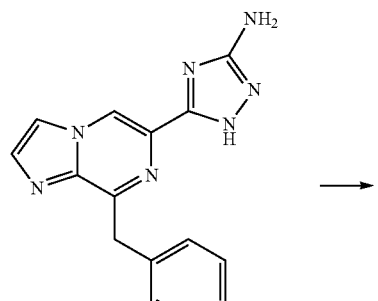

Compound I-57

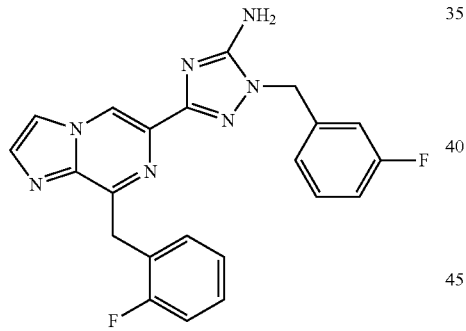

Compound I-58

1-(3-Fluorobenzyl)-3-(8-(2-fluorobenzyl)imidazo[1,2-a]pyrazin-6-yl)-1H-1,2,4-triazol-5-amine (I-58)

To a solution of crude 5-(8-(2-fluorobenzyl)imidazo[1,2-a]pyrazin-6-yl)-1H-1,2,4-triazol-3-amine (360 mg) in DMF (4 mL) was added 1-(bromomethyl)-3-fluorobenzene (0.11 mL, 0.88 mmol) followed by potassium carbonate (210 mg, 1.6 mmol). The reaction mixture was stirred at ambient temperature for 16 hours and then heated to 50° C. for 24 hours. The reaction mixture was cooled to ambient temperature, diluted with water (50 mL) and extracted with EtOAc (4×30 mL). The combined organic phases were dried over Na$_2$SO$_4$, filtered and concentrated to afford a brown residue. First pass purification of the crude product by silica gel chromatography afforded a mixture. Further purification of this material by reverse phase HPLC (10-60% acetonitrile/ water gradient with 0.1% trifluoroacetic acid) afforded 1-(3-fluorobenzyl)-3-(8-(2-fluorobenzyl)imidazo[1,2-a]pyrazin-6-yl)-1H-1,2,4-triazol-5-amine (I-58) (6.9 mg), as a pale yellow solid.

1H NMR (500 MHz, DMSO-d$_6$) δ (ppm) 9.01 (s, 1H), 8.22 (s, 1H), 7.81 (s, 1H), 7.40-7.44 (m, 1H), 7.30-7.34 (m, 1H), 7.24-7.27 (m, 1H), 7.12-7.18 (m, 2H), 7.06-7.10 (m, 3H), 6.78 (br. s, 2H), 5.25 (s, 2H), 4.52 (s, 2H).

LCMS [M+H]=418.3

Compound I-59 and Compound I-60

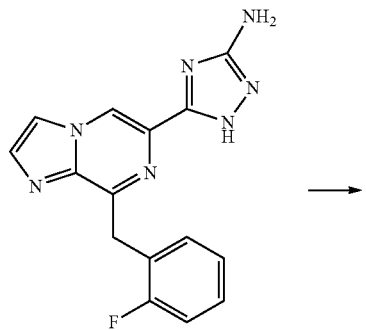

Compound I-57

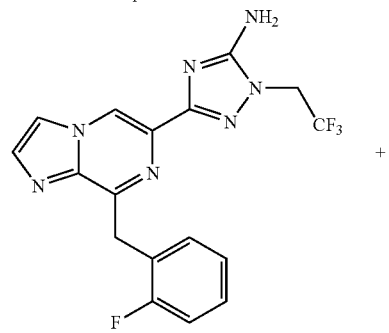

Compound I-59

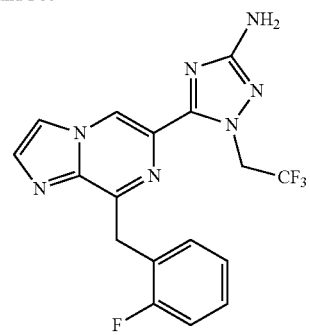

Compound I-60

3-(8-(2-Fluorobenzyl)imidazo[1,2-a]pyrazin-6-yl)-1-(2,2,2-trifluoroethyl)-1H-1,2,4-triazol-5-amine (I-59) and 5-(8-(2-fluorobenzyl)imidazo[1,2-a]pyrazin-6-yl)-1-(2,2,2-trifluoroethyl)-1H-1,2,4-triazol-3-amine (I-60)

A suspension of crude 5-(8-(2-fluorobenzyl)imidazo[1,2-a]pyrazin-6-yl)-1H-1,2,4-triazol-3-amine (550 mg), 2,2,2-trifluoroethyl trifluoromethanesulfonate (0.30 mL, 2.2 mmol) and potassium carbonate (540 mg, 3.90 mmol) in DMF (4 mL) was stirred for 16 hours at ambient temperature. The reaction mixture was then diluted with water (50 mL) and extracted with EtOAc (3×50 mL). The combined organic phases were dried over Na₂SO₄, filtered and concentrated to afford a residue. First pass purification was achieved by silica gel chromatography (0-100% EtOAc/hexanes gradient). A second purification using silica gel chromatography (0-50% acetonitrile/MeOH (7:1) in DCM gradient) afforded 5-(8-(2-fluorobenzyl)imidazo[1,2-a]pyrazin-6-yl)-1-(2,2,2-trifluoroethyl)-1H-1,2,4-triazol-3-amine (I-60) (40 mg) as a gold solid. Compound I-59 was detected in this campaign, but not isolated. In a second campaign, crude 5-(8-(2-fluorobenzyl)imidazo[1,2-a]pyrazin-6-yl)-1H-1,2,4-triazol-3-amine (330 mg), 2,2,2-trifluoroethyl trifluoromethanesulfonate (0.18 mL, 1.3 mmol), and potassium carbonate (320 mg, 2.4 mmol) in DMF (4 mL) were combined to afford a similar mixture of products. Purification of this reaction mixture using reverse phase HPLC (10-55% acetonitrile/water gradient with 0.1% formic acid) afforded 3-(8-(2-fluorobenzyl)imidazo[1,2-a]pyrazin-6-yl)-1-(2,2,2-trifluoroethyl)-1H-1,2,4-triazol-5-amine (I-59) (3.5 mg) as a white solid.

Compound I-60:

$^1$H NMR (500 MHz, DMSO-d$_6$) δ (ppm) 9.19 (s, 1H), 8.31 (d, 1H), 7.92 (d, 1H), 7.45-7.50 (m, 1H), 7.30-7.36 (m, 1H), 7.14-7.20 (m, 2H), 5.64 (s, 2H), 5.21 (q, 2H), 4.62 (s, 2H).

LCMS [M+H]=392.2

Compound I-59:

$^1$H NMR (500 MHz, DMSO-d$_6$) δ (ppm) 8.98 (s, 1H), 8.22 (s, 1H), 7.78 (s, 1H), 7.30-7.34 (m, 1H), 7.24-7.29 (m, 1H), 7.15-7.19 (m, 1H), 7.06-7.09 (m, 1H), 6.76 (s, 2H), 4.98 (q, 2H), 4.43 (s, 2H). The regiochemical assignments were confirmed by $^1$H NMR nOe experiments (~3% nOe exists between C$\underline{H}_2$CF$_3$ protons and N$\underline{H}_2$ group).

LCMS [M+H]=392.2

Compound I-62 and Compound I-63

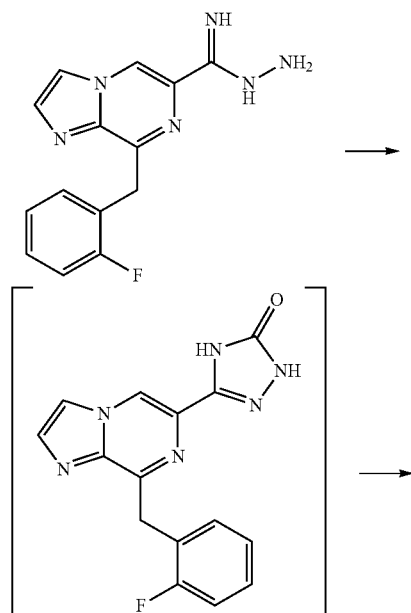

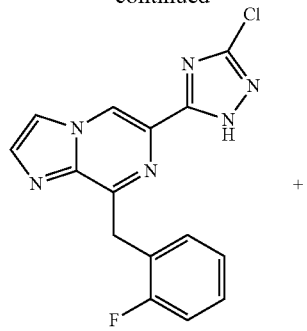

Compound I-62

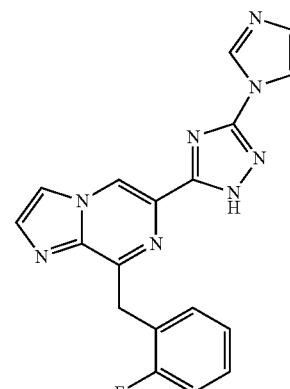

Compound I-63

6-(3-Chloro-1H-1,2,4-triazol-5-yl)-8-(2-fluorobenzyl)imidazo[1,2-a]pyrazine (I-62) and 6-(3-(1H-imidazol-1-yl)-1H-1,2,4-triazol-5-yl)-8-(2-fluorobenzyl)imidazo[1,2-a]pyrazine (I-63)

A solution containing 8-(2-fluorobenzyl)imidazo[1,2-a]pyrazine-6-carboximidhydrazide (140 mg, 0.51 mmol) and 1,1'-carbonyldiimidazole (CDI) (410 mg, 2.5 mmol) in THF (4 mL) was stirred at ambient temperature for 40 hours. A tan suspension was observed. DCM/MeOH (60 mL, 1:1 ratio) was added and the resultant mixture was gently warmed to dissolve the solids. The crude mixture was concentrated and dried in vacuo. Phosphoryl trichloride (3.0 mL, 32 mmol) was added and the resultant mixture was heated at 120° C. for 16 hours. The reaction mixture was concentrated, carefully treated with ice and neutralized with saturated NaHCO₃ solution. The crude mixture was extracted with DCM/isopropanol (5:1 ratio, 3×20 mL). The combined organic layers were dried over Na₂SO₄, filtered and concentrated in vacuo. Purification by silica gel chromatography (0-25% acetonitrile/MeOH (7:1) in DCM) afforded the title compounds I-62 (23 mg, 14% yield, first eluting product) as an off-white solid and I-63 (18 mg, 9.9% yield, second eluting side product) as a light tan solid.

Compound I-62:

$^1$H NMR (500 MHz, DMSO-d$_6$) δ (ppm) 14.9 (s, 1H), 9.31 (s, 1H), 8.25 (s, 1H), 7.85 (s, 1H), 7.43 (app. t, 1H), 7.27 (m, 1H), 7.17 (app. t, 1H), 7.09 (app. t, 1H), 4.58 (s, 2H).

LCMS [M+H]=329.2

Compound I-63:

¹H NMR (500 MHz, DMSO-d₆) δ (ppm) 14.8 (s, 1H), 9.36 (s, 1H), 8.32 (m, 2H), 7.86 (s, 1H), 7.76 (s, 1H), 7.43 (app. t, 1H), 7.28 (m, 1H), 7.20-7.15 (m, 2H), 7.10 (app. t, 1H), 4.60 (s, 2H).

LCMS [M+H]=361.3

Compound I-64 and Compound I-65

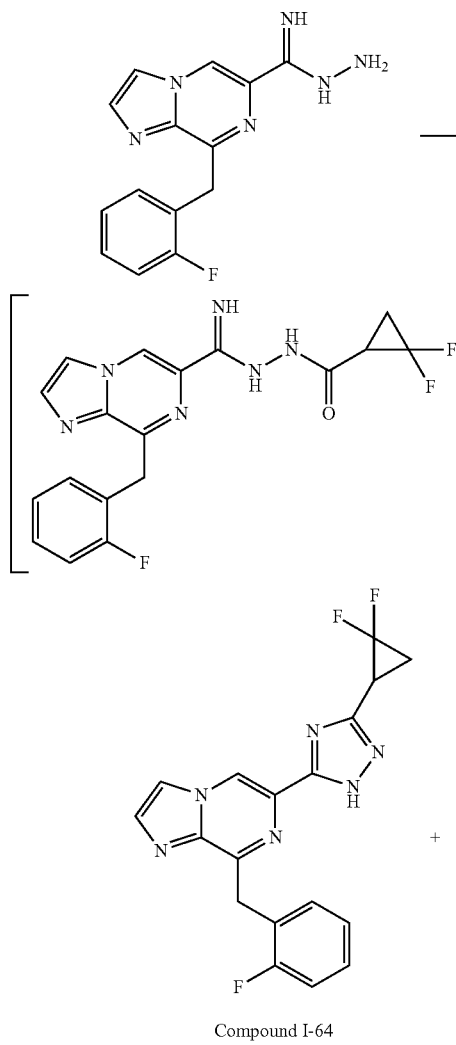

Compound I-64 rac-6-(3-(2,2-Difluorocyclopropyl)-1H-1,2,4-triazol-5-yl)-8-(2-fluorobenzyl)imidazo[1,2-a]pyrazine (I-64) and 5-(8-(2-fluorobenzyl)imidazo[1,2-a]pyrazin-6-yl)-N,N-dimethyl-1H-1,2,4-triazol-3-amine (I-65)

A solution of rac-2,2-difluorocyclopropane-1-carboxylic acid (89 mg, 0.70 mmol) in DMF (2.0 mL) was treated successively with HATU (400 mg, 1.0 mmol) and 4-methylmorpholine (0.23 mL, 2.1 mmol). The amber color solution was stirred at ambient temperature for 30 minutes and then added to 8-(2-fluorobenzyl)imidazo[1,2-a]pyrazine-6-carboximidhydrazide (200 mg, 0.70 mmol) with the aid of 0.50 mL of DMF. After 18 hours, the reaction was diluted with EtOAc (100 mL) and water (50 mL). The aqueous layer was back-extracted with EtOAc (25 mL). The combined organic layers were washed with brine, dried over Na2SO4, filtered and concentrated in vacuo to yield 2,2-difluoro-N'-((8-(2-fluorobenzyl)imidazo[1,2-a]pyrazin-6-yl)(imino)methyl)cyclopropane-1-carbohydrazide (400 mg, >99% yield) as a brown solid which was used without further manipulations. This intermediate was suspended in ethanol (10 mL) and acetic acid (1.0 mL). The reaction was heated at 90° C. for 15.5 hours. Contents were concentrated in vacuo and the resulting residue was purified twice by silica gel chromatography (20-10% EtOAc/hexanes gradient and 0-4% acetonitrile/MeOH (7:1) in DCM gradient) and re-purified by reverse phase HPLC (5-95% acetonitrile/water with 0.1% formic acid) to deliver the title compounds I-64 (51 mg, 19% yield, first eluting product) as a white solid and I-65 (20 mg, 8.5% yield, second eluting side-product) as an off-white solid.

Compound I-64:

¹H NMR (500 MHz, Methanol-d₄) δ (ppm) 9.12 (s, 1H), 8.16 (s, 1H), 7.83 (s, 1H), 7.32 (m, 1H), 7.25 (m, 1H), 7.11-7.02 (m, 2H), 4.67 (s, 2H), 2.97 (m, 1H), 2.17 (m, 1H), 2.00 (m, 1H).

LCMS [M+H]=371.2

Compound I-65:

¹H NMR (500 MHz, Methanol-d₄) δ (ppm) 9.08 and 8.98 (s, 1H, tautomers), 8.13 and 8.10 (s, 1H, tautomers), 7.87 and 7.77 (s, 1H, tautomers), 7.36-7.16 (m, 2H), 7.13-6.98 (m, 2H), 4.64 (s, 2H), 3.09 and 3.03 (s, 6H, tautomers).

LCMS [M+H]=338.2

Compound I-66

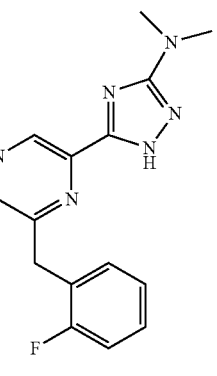

Compound I-65

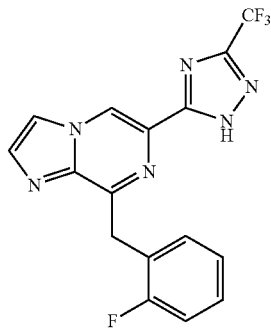

Compound I-1

-continued

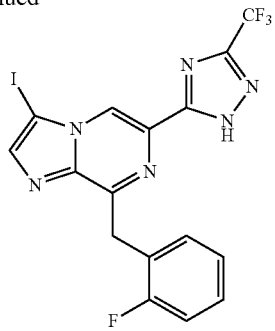

Compound I-66

8-(2-Fluorobenzyl)-3-iodo-6-(3-(trifluoromethyl)-1H-1,2,4-triazol-5-yl)imidazo[1,2-a]pyrazine (I-66)

A solution of 8-(2-fluorobenzyl)-6-(3-(trifluoromethyl)-1H-1,2,4-triazol-5-yl)imidazo[1,2-a]pyrazine (99 mg, 0.27 mmol) in DMF (2.0 mL) was treated with N-iodosuccinimide (92 mg, 0.41 mmol) and heated to 60° C. for 40 hours. The reaction mixture was concentrated and purified by silica gel chromatography (0-5% acetonitrile/MeOH (7:1) in DCM gradient) to afford the title compound (I-66) (130 mg, 96% yield) as a white solid.

1H NMR (500 MHz, DMSO-d$_6$) δ (ppm) 15.6 (s, 1H), 8.79 (s, 1H), 8.04 (s, 1H), 7.41 (app. t, 1H), 7.27 (m, 1H), 7.18 (app. t, 1H), 7.08 (app. t, 1H), 4.62 (s, 2H).

LCMS [M+H]=489.2

Compound I-67

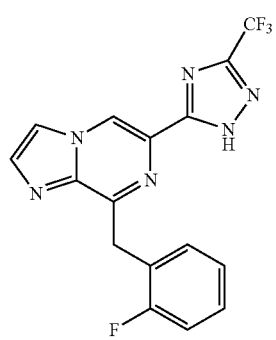

Compound I-1

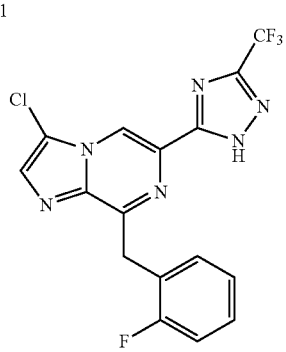

Compound I-67

3-Chloro-8-(2-fluorobenzyl)-6-(3-(trifluoromethyl)-1H-1,2,4-triazol-5-yl)imidazo[1,2-a]pyrazine (I-67)

A solution of 8-(2-fluorobenzyl)-6-(3-(trifluoromethyl)-1H-1,2,4-triazol-5-yl)imidazo[1,2-a]pyrazine (99 mg, 0.27 mmol) in DMF (2.0 mL) was treated with N-chlorosuccinimide (55 mg, 0.41 mmol) and heated to 60° C. for 24 hours. The reaction mixture was concentrated and purified by silica gel chromatography (0-20% acetonitrile/MeOH (7:1) in DCM gradient) to afford the title compound (I-67) (56 mg, 51% yield) as a white solid.

1H NMR (500 MHz, Methanol-d$_4$) δ (ppm) 9.04 (s, 1H), 7.88 (s, 1H), 7.39 (app. t, 1H), 7.26 (m, 1H), 7.08 (m, 2H), 4.70 (s, 2H).

LCMS [M+H]=397.2

Compound I-68

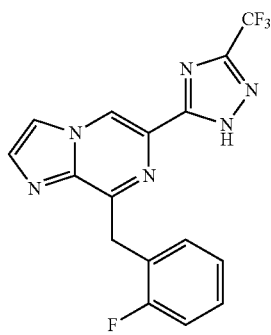

Compound I-1

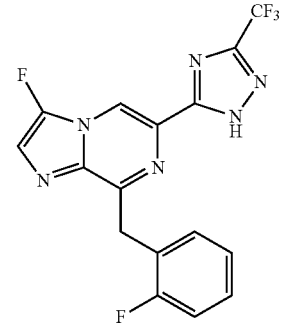

Compound I-68

3-Fluoro-8-(2-fluorobenzyl)-6-(3-(trifluoromethyl)-1H-1,2,4-triazol-5-yl)imidazo[1,2-a]pyrazine (I-68)

A solution of 8-(2-fluorobenzyl)-6-(3-(trifluoromethyl)-1H-1,2,4-triazol-5-yl)imidazo[1,2-a]pyrazine (100 mg, 0.28 mmol) in acetonitrile (3.0 mL) was treated with 1-chloromethyl-4-fluoro-1,4-diazoniabicyclo[2.2.2]octane bis(tetrafluoroborate) (Selectfluor®) (120 mg, 0.34 mmol) and heated to 70° C. for 6 hours. Additional amount of Selectfluor® (60 mg, 0.17 mmol) was added and heating was continued at 70° C. for 3 hours. The reaction mixture was concentrated and purified by silica gel chromatography (0-20% acetonitrile/MeOH (7:1) in DCM gradient) to afford the title compounds I-68 (10 mg, 9.4% yield) as a white solid.

1H NMR (500 MHz, Methanol-d$_4$) δ (ppm) 8.96 (s, 1H), 7.56 (d, 1H), 7.39 (app. t, 1H), 7.25 (m, 1H), 7.08 (m, 2H), 4.65 (s, 2H).

LCMS [M+H]=381.2

Compound I-70

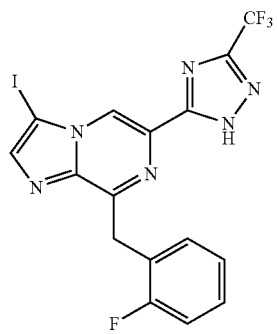

Compound I-66

→

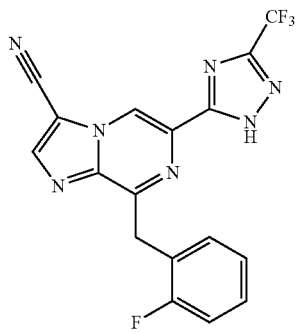

Compound I-70

8-(2-Fluorobenzyl)-6-(3-(trifluoromethyl)-1H-1,2,4-triazol-5-yl)imidazo[1,2-a]pyrazine-3-carbonitrile (I-70)

A solid mixture comprised of 8-(2-fluorobenzyl)-3-iodo-6-(3-(trifluoromethyl)-1H-1,2,4-triazol-5-yl)imidazo[1,2-a]pyrazine (49 mg, 0.10 mmol), zinc cyanide (18 mg, 0.15 mmol), [1,1'-bis(diphenylphosphino)ferrocene]dichloropalladium(II) (3.7 mg, 5.0 μmop, and zinc powder (1.3 mg, 0.020 mmol) was flushed with nitrogen for 15 minutes. DMF (2 mL) was added and the reaction was heated at 120° C. in a microwave for 7.5 hours during which additional amounts of the palladium catalyst (3.7 mg) and zinc cyanide (24 mg) were added to drive the reaction. The crude mixture was cooled to ambient temperature, diluted with EtOAc (10 mL) and filtered through a bed of Celite with EtOAc (20 mL). The organic filtrate was washed with water/brine (2×10 mL, 10:1 ratio) and brine (10 mL), dried over Na$_2$SO$_4$, filtered and concentrated in vacuo. Purification by silica gel chromatography (0-10% acetonitrile/MeOH (7:1) in DCM gradient) afforded the title compound I-70 as an off-white solid (15 mg, 38% yield).

$^1$H NMR (500 MHz, Methanol-d$_4$) δ (ppm) 9.23 (s, 1H), 8.44 (s, 1H), 7.41 (app. t, 1H), 7.26 (m, 1H), 7.10-7.05 (m, 2H), 4.74 (s, 2H).

LCMS [M+H]=388.3

Compound I-71

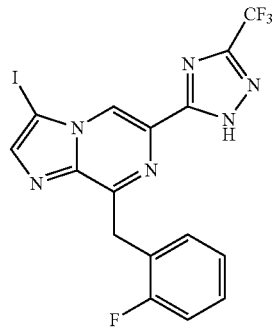

Compound I-66

→

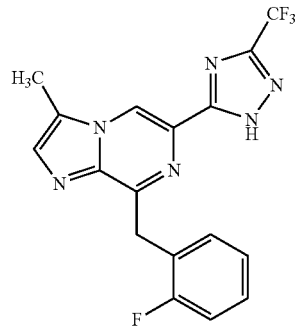

Compound I-71

8-(2-Fluorobenzyl)-3-methyl-6-(3-(trifluoromethyl)-1H-1,2,4-triazol-5-yl)imidazo[1,2-a]pyrazine (I-71)

A solid mixture comprised of 8-(2-fluorobenzyl)-3-iodo-6-(3-(trifluoromethyl)-1H-1,2,4-triazol-5-yl)imidazo[1,2-a]pyrazine (71 mg, 0.15 mmol), potassium carbonate (60 mg, 0.44 mmol) and tetrakis(triphenylphosphine)palladium(0) (17 mg, 0.015 mmol) was flushed with nitrogen for 5 minutes. DME (3.5 mL) and water (0.5 mL) were added followed by trimethylboroxine (37 μL, 0.29 mmol). The reaction was heated at 100° C. for 5 hours and then at 120° C. for 1 hour. Additional amounts of the palladium catalyst (17 mg) and trimethylboroxine (37 μL) were added and the reaction was heated at 120° C. for 40 hours. The crude mixture was cooled to ambient temperature, poured into water (20 mL) and neutralized to pH 7 with 1 N HCl solution. The aqueous mixture was extracted with EtOAc (2×20 mL). The combined organic phases were dried over Na$_2$SO$_4$, filtered and concentrated in vacuo. Purification by silica gel chromatography (0-40% EtOAc/hexanes gradient) and reverse phase HPLC (30-80% acetonitrile/water gradient with 0.1% formic acid) afforded the title compound I-71 as a white solid (16 mg, 29% yield).

$^1$H NMR (500 MHz, Methanol-d$_4$) δ (ppm) 8.99 (s, 1H), 7.66 (s, 1H), 7.33 (app. t, 1H), 7.24 (m, 1H), 7.11-7.03 (m, 2H), 4.67 (s, 2H), 2.63 (s, 3H).

LCMS [M+H]=377.2

Example 2a: Biological Activity Measurement by the cGMP GloSensor Cell-Based Assay, 384-Well Format Human embryonic kidney cells (HEK293) cells expressing GloSensor™ 40F cGMP (Part No: CS182801, Promega) were used to evaluate the activity of test compounds. The luminescent biosensors (engineered luciferase) that were incorporated into these cells detect cGMP formed by the compounds stimulating the sGC enzyme and emit luminescence.

cGMP GloSensor cells were maintained in Dulbecco's Modification of Eagle's Medium (DMEM) supplemented with fetal bovine serum (FBS, 10% final) and hygromycine (200 ug/ml). The day before assay, cells were plated in DMEM with 10% FBS in a 50 μL volume at a density of $1.5\times10^4$ cells/well in a poly-D-lysine coated 384-well flat white-bottom plate (Corning Cat No 35661). Cells were incubated overnight at 37° C. in a humidified chamber with 5% $CO_2$. The next day, medium was removed and cells were replaced with 40 ul/well of GloSensor™, 2 mM (Promega Cat No E1291). Cells were treated for 90 minutes at 25° C. to allow the substrate to equilibrate in the cells. Test compounds and Diethylenetriamine NONOate (DETA-NONOate, or DETA-NO) was diluted to 3 mM (20×) in serum-free $CO_2$ independent medium and serially diluted at 4× dilutions to create 5× dose curve from which 10 ul was added to the wells (xμM concentration for test compound solution and 10 μM concentration for DETA-NONOate solution; wherein x is one of the following final concentrations: 30000 nM, 7500 nM, 1875 nM, 468.8 nM, 117.2 nM, 29.29 nM, 7.320 nM, 1.830 nM, 0.460 nM, 0.114 nM, and 0.029 nM).

For the kinetics studies, luminescense was measured right away for 0.2 sec per well with Envision (Perkin Elmer). For endpoint SAR screening, data were collected after 55 min incubation at room temperature.

Data were normalized to a high control using the following equation: 100*(Sample−Low Control)/(High Control−Low Control), where the low control is the average of 16 samples treated with 1% DMSO, and the high control is the average of 16 samples treated with 30 μM of Compound Y depicted below. Data were fit using a 4-parameter fit (log (agonist) vs. response–variable slope) using GraphPad Prism Software v.5. n=2 for all compounds. The Absolute (Abs) $EC_{50}$ was interpolated from the curve fit and is defined as the concentration at which a given compound elicits 50% of the high control response after data normalization as indicated above. Compounds failing to elicit a minimum response of 50% are reported as >30 μM or ND. For compounds run in duplicate or n higher than 2, the result herein given is the geometric mean of the several results obtained. Table 2a summarizes results obtained for selected compounds of the invention in this assay.

Compound Y

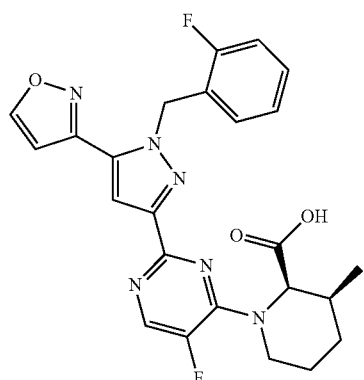

TABLE 2a

Whole cell activity in the GloSensor cell-based assay, 384-well format (Example 2a)

| Compound | Abs EC50 (nM) |
|---|---|
| I-1 | A |
| I-2 | A |
| I-3 | B |
| I-4 | B |
| I-5 | A |
| I-6 | B |
| I-7 | B |
| I-8 | A |
| I-9 | A |
| I-10 | A |
| I-11 | B |
| I-12 | B |
| I-13 | C |
| I-14 | A |
| I-15 | B |
| I-16 | A |
| I-17 | A |
| I-18 | A |
| I-19 | C |
| I-20 | C |
| I-21 | A |
| I-22 | A |
| I-23 | A |
| I-24 | A |
| I-25 | A |
| I-26 | A |
| I-27 | A |
| I-28 | A |
| I-29 | A |
| I-30 | A |
| I-31 | B |
| I-32 | C |
| I-33 | A |
| I-34 | A |
| I-35 | A |
| I-36 | C |
| I-37 | C |
| I-38 | A |
| I-39 | |
| I-41 | A |
| I-42 | C |
| I-47 | A |
| I-48 | A |
| I-50 | B |
| I-51 | A |
| I-53 | B |
| I-54 | B |
| I-56 | A |
| I-57 | B |
| I-58 | A |
| I-59 | A |
| I-60 | C |
| I-62 | A |
| I-63 | B |
| I-64 | B |
| I-65 | B |
| I-66 | B |
| I-67 | A |
| I-68 | A |
| I-70 | B |
| I-71 | A |
| I-72 | C | sGC enzyme activity values in HEK cells, determined by the GloSensor assay.

(~) Code definitions for the sGC enzyme activity values, expressed as Absolute $EC_{50}$ which is defined as the concentration at which a given compound elicits 50% of the high control response (Compound Y) after data normalization:
Abs EC50 ≤ 100 nM = A; 100 nM < Abs EC50 ≤ 1000 nM = B; 1000 nM < Abs EC50 = C.
Compounds failing to elicit a minimum response of 50% are reported as >30 μM or ND.

Example 2b: Biological Activity Measurement by the cGMP GloSensor Cell-Based Assay, 384-Well Format HEK293 cells expressing GloSensor™ 40F cGMP (Part No: CS182801, Promega) were used to evaluate the synergy of the test compounds with NO. Multiple assays where run in which the concentrations of test compound also well as the concentration of Diethylenetriamine NONOate (DETA-NONOate) were varied to determine the synergy of the test compound with NO. Test compounds and Diethylenetriamine NONOate (DETA-NONOate or DETA-NO) were diluted to 3 mM (20×) in serum-free $CO_2$ independent medium and serially diluted at 4χ dilutions to create 5× dose curve from which 10 ul was added to the wells (xμM concentration for test compound solution and y μM concentration for DETA-NO solution; wherein x is one of the following final concentrations: 30000 nM, 7500 nM, 1875 nM, 468.8 nM, 117.2 nM, 29.29 nM, 7.320 nM, 1.830 nM, 0.460 nM, 0.114 nM, and 0.029 nM and y is one of the following final concentrations: 30 μM, 10 μM, 3.33 μM 1.11 μM, and 0 μM).

Following the analysis as described above, Table 2b summarizes results obtained for Compound I-1 with the various DETA-NO amount in this assay.

TABLE 2b

Whole cell activity in the GloSensor cell-based assay, 384-well format (Example 2b)

| [DETA-NO] | 30 uM | 10 uM | 3.33 uM | 1.11 uM | 0 uM |
|---|---|---|---|---|---|
| I-1 - $EC_{50}$ | A | B | B | B | B | sGC enzyme activity values in HEK cells, determined by the GloSensor assay.
(~) Code definitions for the sGC enzyme activity values, expressed as Absolute $EC_{50}$ which is defined as the concentration at which a given compound elicits 50% of the high control response (Compound Y) after data normalization:
Abs EC50 ≤ 100 nM = A; 100 nM < Abs EC50 ≤ 1000 nM = B; 1000 nM < Abs EC50 = C.
Compounds failing to elicit a minimum response of 50% are reported as >30 μM or ND.

As shown in Table 2b, Compound I-1 synergizes with NO to stimulate sGC.

Example 3. Biological Activity Measurement by the cGMP Neuronal Cell-Based Assay Rat primary neurons were isolated from fetuses of 18-day pregnant Sprague-Dawley females. The fetuses were collected in Hanks' balanced salt solution (HBSS) and brains were rapidly removed. The cerebral hippocampi were isolated and mechanically fragmented. Further tissue digestion was performed with 0.25% (wt/vol) trypsin solution in HBSS without Ca2+ and Mg2+ for 15 min at 37° C. After trypsination, cells were washed and resuspended in neurobasal medium supplemented with 0.5 mM L-glutamine, 12.5 uM glutamic acid, 2% B-27 and 100 U/mL penicillin, and 100 μg/mL streptomycin. Cells were plated at a density of $4\times10^4$ cells/well in a poly-D-lysine coated 384-well flat clear-bottom plate (Corning Cat No 354662). Cells were incubated 6-7 days at 37° C. in a humidified chamber with 5% $CO_2$. Media was removed and cells were washed 1× with HBSS containing Ca2+ and Mg2+, and replaced with 40 uL HBSS containing 0.5 mM IBMX, and incubated for 15 minutes at 37° C. 10 uL of a 5× stock of test compounds with diethylenetriamine NONOate (DETA-NO) was added. Final concentration of DETA-NO was 30 μM. Cells were incubated for 20 min at 37° C. Medium was removed, 50 uL of ice-cold 10% acetic acid was added, and incubated for 60 minutes at 4° C. Following centrifugation at 4° C. for 5 minutes at 1000×g to pellet cell debris, the supernatant was aspirated to a clean plate and the samples were analyzed for cGMP content. cGMP concentrations were determined from each sample using LC-MS/MS.

Data were normalized to a high control using the following equation: 100*(Sample−Low Control)/(High Control−Low Control), where the low control is the average of 15 samples treated with 1% DMSO, and the high control is the average of 15 samples treated with 10 μM a known sGC stimulator Compound Y. Data were fit using a 4-parameter fit (log(agonist) vs. response−variable slope) using GraphPad Prism Software v.5. n=2 for all compounds. The Absolute $EC_{50}$ was interpolated from the curve fit and is defined as the concentration at which a given compound elicits 50% of the high control response. Compounds failing to elicit a minimum response of 50% are reported as >30 μM. For compounds run in duplicate or n higher than 2, the result herein given is the geometric mean of the several results obtained. Table 3 summarizes results obtained for selected compounds of the invention in this assay.

TABLE 3

Biological activity in the cGMP neuronal cell-based assay (Example 3)

| Compound | Abs EC50 (nM) |
|---|---|
| I-1 | A |
| I-6 | A |
| I-7 | B |
| I-10 | A |
| I-11 | A |
| I-14 | A |
| I-2 | A |
| I-3 | A |
| I-5 | A |
| I-8 | A |
| I-9 | A |
| I-12 | B |
| I-13 | C |
| I-15 | B |
| I-16 | A |

Neuronal-based cell assay.
AbsEC50 ≤ 100 nM = A; 100 nM < AbsEC50 ≤ 1000 nM = B; 1000 nM < AbsEC50 = C.
Compounds failing to elicit a minimum response of 50% are reported as >30 μM or ND.

Example 4: Rat Cerebrospinal Fluid (CSF) Pharmacokinetic Properties

Protocol.

PK in rats was determined following oral dosing. For the oral (PO) experiments, a group of 6 male Sprague-Dawley rats with an indwelling catheter placed in the cisterna magna were used. The PO group was dosed with 10 mg/kg or 1 mg/kg of a compound formulated as a solution in PEG400. PO doses were administered by oral gavage and delivered to the stomach using a syringe and gavage tube. Following oral dosage administration, the gavage tube was flushed with approximately 0.5 mL of water to ensure complete delivery of the full dose.

Plasma samples were collected as follows: samples of CSF and blood were collected at 1 hour, 2, and optionally at 4 hours post-dosing. CSF samples (0.05 mL) were collected through the intracisternal catheter. Blood samples (0.25 mL) were collected through retro-orbital sampling. These samples were kept on ice until processed for plasma. Blood samples were centrifuged at 3200 rpm for 5 minutes at approximately 5° C. within 1 hour of collection. Plasma was directly transferred to a 96-well plate tube (0.125 mL). Plug caps were placed on the tubes and the tubes frozen at approximately −70° C. and stored until analysis. Plasma was collected and analyzed for the presence of a compound.

Quantitation of Compounds.

The compound in question and the internal standard were extracted from plasma and CSF by precipitation. Samples were analyzed using liquid chromatography (LC) with tandem mass spectrometric detection (MS/MS) using electrospray ionization. The standard curve range was from 1 to 1000 ng/mL. Results of the compounds described herein in this assay are illustrated in Table 4a below (10 mg/kg dose) and Tables 4b and 4c below (1 mg/kg).

Kp,uu is defined as the concentration ratio of unbound drug in CSF to unbound drug in plasma. Unbound drug in plasma (or free plasma concentration) is calculated by multiplying the total plasma concentration by the unbound fraction as determined by plasma protein binding. The CSF concentration is then divided by the free plasma concentration to determine the Kp,uu. (See e.g., Di et al., *J. Med. Chem.*, 56, 2-12 (2013))

Table 4a: CSF PK properties of select compounds described herein (Example 4) at a 10 mg/kg dose.

TABLE 4a

CSF PK properties of select compounds described herein (Example 4) at a 10 mg/kg dose.

| Compound | CSF Conc. (nM @ 1 h) | Kp, uu (@ 1 h) |
|---|---|---|
| I-1 | 210 | 0.9 |
| I-10 | 108 | 3.1 |
| I-11 | 72 | 2.1 |
| I-14 | 284 | 1.7 |
| I-2 | 59 | 0.9 |
| I-3 | 6 | 0.8 |
| I-16 | 272 | 1.6 |
| I-27 | 41 | 0.2 |
| I-28 | 20 | 0.2 |

TABLE 4b

CSF Concentration of a select compound described herein (Example 4) at a 1 mg/kg dose.

| | CSF Conc. (nM) | | |
|---|---|---|---|
| Cmpd | @ 1 h | @ 2 h | @ 4 h |
| I-1 | 21 | 35 | 39 |

TABLE 4c

Kp, uu of a select compound described herein (Example 4) at a 1 mg/kg dose.

| | Kp, uu | | |
|---|---|---|---|
| Cmpd | @ 1 h | @ 2 h | @ 4 h |
| I-1 | 1.0 | 1.4 | 1.9 |

Example 5: Dog Cerebrospinal Fluid (CSF) Pharmacokinetic Properties

Protocol.

PK in dogs was determined following oral dosing. A group of 4 male beagle dogs were used and the dogs were dosed with 1 mg/kg of a compound formulated as a suspension in 1% HPMC E5, 0.2% Tween 80, and 0.5% MC in water. PO doses were administered by oral gavage in a gelatin capsule and delivered to the stomach using a gavage tube. Following oral dosage administration, the gavage tube was flushed with approximately 10 mL of water to ensure complete delivery of the full dose.

Plasma and CSF samples were collected as follows: samples of CSF and blood were collected at 1, 2, 4 and 8 hours post PO dosing. CSF samples (0.05 mL) were collected from the lumbosacral region (L4/5) via direct needle puncture at the appropriate time points. Blood samples (0.25 mL) were collected via cephalic vein. These samples were kept on ice until processed for plasma. Blood samples were centrifuged at 3200 rpm for 5 minutes at approximately 5° C. within 1 hour of collection. Plasma was directly transferred to a 96-well plate tube (0.125 mL). Plug caps were placed on the tubes and the tubes frozen at approximately −70° C. and stored until analysis. Plasma was collected and analyzed for the presence of a compound.

Quantitation of Compounds.

The compound of the invention and the internal standard were extracted from plasma and CSF by precipitation. Samples were analyzed using liquid chromatography (LC) with tandem mass spectrometric detection (MS/MS) using electrospray ionization. The standard curve range was from 1 to 1000 ng/mL. Results of the compounds described herein in this assay are illustrated in Tables 5a and 5b below (1 mg/kg dose).

Kp,uu is defined as the concentration ratio of unbound drug in CSF to unbound drug in plasma. Unbound drug in plasma (or free plasma concentration) is calculated by multiplying the total plasma concentration by the unbound fraction as determined by plasma protein binding. The CSF concentration is then divided by the free plasma concentration to determine the Kp,uu. (See e.g., Di et al., *J. Med. Chem.*, 56, 2-12 (2013))

TABLE 5a

CSF Concentration of a select compound described herein (Example 5) at a 1 mg/kg dose.

| | CSF Conc. (nM) | | | |
|---|---|---|---|---|
| Cmpd | @ 1 h | @ 2 h | @ 4 h | @ 8 h |
| I-1 | 34 | 34 | 19 | 2.4 |

TABLE 5b

Kp, uu of a select compound described herein (Example 5) at a 1 mg/kg dose.

| | Kp, uu | | | |
|---|---|---|---|---|
| Cmpd | @ 1 h | @ 2 h | @ 4 h | @ 8 h |
| I-1 | 0.7 | 0.7 | 0.7 | 0.4 |

Example 6: Non-Human Primate (NHP) Cerebrospinal Fluid (CSF) Pharmacokinetic Properties Protocol.

PK in NHP was determined following intravenous and oral dosing. For the intravenous (IV) experiments, a group of 4 male Cynomolgus monkeys were used. The IV group was dosed with 0.3 mg/kg of a compound formulated as a solution in 10% PEG-400, 25% of a 20% Solutol HS 15 in Water, and 65% DPBS. IV doses were administered by injection and delivered via catheter into the cephalic vein. For the oral (PO) experiments, a group of 4 male Cynomolgus monkeys were used. The PO group was dosed with 1 mg/kg of a compound formulated as a suspension in 1% HPMC E5, 0.2% Tween 80, 0.5% MC in water. PO doses were administered by oral gavage and delivered via gelatin capsule.

Plasma and CSF samples were collected as follows: samples of CSF and blood were collected at 1, 4 and 24 hours post IV dosing and 2, 8 and 24 hours post PO dosing. CSF samples (0.05 mL) were collected either the cisterna magna (primary site) or the lumbosacral region (L4/5) via direct needle puncture at the appropriate time points. Blood samples (0.25 mL) were collected from a peripheral vein. These samples were kept on ice until processed for plasma. Blood samples were centrifuged at 3200 rpm for 5 minutes at approximately 5° C. within 1 hour of collection. Plasma was directly transferred to a 96-well plate tube (0.125 mL). Plug caps were placed on the tubes and the tubes frozen at approximately −70° C. and stored until analysis. Plasma was collected and analyzed for the presence of a compound.

Quantitation of Compounds.

The compound of the invention and the internal standard were extracted from plasma and CSF by precipitation. Samples were analyzed using liquid chromatography (LC) with tandem mass spectrometric detection (MS/MS) using electrospray ionization. The standard curve range was from 1 to 1000 ng/mL. Results of the compounds described herein in this assay are illustrated in Tables 6a and 6b below (0.3 mg/kg IV dose, 1 mg/kg PO dose).

$K_{p,uu}$ is defined as the concentration ratio of unbound drug in CSF to unbound drug in plasma. Unbound drug in plasma (or free plasma concentration) is calculated by multiplying the total plasma concentration by the unbound fraction as determined by plasma protein binding. The CSF concentration is then divided by the free plasma concentration to determine the $K_{p,uu}$. (See e.g., Di et al., *J. Med. Chem.*, 56, 2-12 (2013))

TABLE 6a

CSF Concentration of a select compound described herein (Example 6) at a 0.3 mg/kg IV and 1 mg/kg PO dose.

| | | CSF Conc. (nM) | | | | |
|---|---|---|---|---|---|---|
| Cmpd | @ 1 h, IV | @ 2 h, PO | @ 4 h, IV | @ 8 h, PO | @ 24 h, IV | @ 24 h, PO |
| I-1 | 27 | 42 | 20 | 31 | 6 | 11 |

TABLE 6b

Kp, uu of a select compound described herein (Example 6) at a 0.3 mg/kg IV and 1 mg/kg PO dose.

| | | Kp, uu | | | | |
|---|---|---|---|---|---|---|
| Cmpd | @ 1 h, IV | @ 2 h, PO | @ 4 h, IV | @ 8 h, PO | @ 24 h, IV | @ 24 h, PO |
| I-1 | 1.8 | 1.8 | 3.0 | 2.5 | 2.8 | 2.1 |

Example 7: Rat Cerebrospinal Fluid (CSF) Biomarker Measurement

This experiment was to determine the effect of different doses of a compound of the invention on the cGMP response as well as the compound concentration in rat CSF and compound concentration in rat plasma.

Protocol.

Each rat was sampled one time or multiple times with 3 or more days in between each dosing.

Day Before the Experiment.

Fast rats overnight with ad libitum access to water.

Day of the Experiment.

Compound and cyclic guanosine monophosphate (cGMP) in rat CSF was determined following oral dosing. Male Sprague-Dawley rats with an indwelling catheter placed in the cisterna magna were used. The rats were dosed with 0 mg/kg (n=15), 3 mg/kg (n=19) and 10 mg/kg (n=20) of a compound of the invention formulated as a suspension in 0.5% methylcellulose, 0.5% Tween80. PO doses were administered by oral gavage and delivered to the stomach using a syringe and gavage tube. Following oral dosage administration, the gavage tube was flushed with approximately 0.5 mL of water to ensure complete delivery of the full dose.

Plasma and CSF samples were collected under isoflurane anesthesia as follows: samples of CSF were collected at 1 hour and 6 hours post-dosing and samples of blood were collected 1 h post-dosing. CSF samples were collected through the intracisternal catheter. Approximately 20 μL of CSF and discard (dead volume is 14-16 μL); then withdraw approximately 50 μL of CSF in eppendorf tubes containing 5 μL of glacial acetic acid. Snap freeze CSF by immersion in liquid nitrogen. Blood samples (0.25 mL) were collected through retro-orbital sampling. These samples were kept on ice until processed for plasma. Blood samples were centrifuged at 3200 rpm for 10 minutes at approximately 5° C. within 1 hour of collection. Plasma was directly transferred to a 96-well plate tube (0.125 mL). Plug caps were placed on the tubes and the tubes frozen at approximately −70° C. and stored until analysis. Plasma was collected and analyzed for the presence of a compound.

Quantitation of Compounds and cGMP.

The compound of the invention, cGMP and the internal standard were extracted from plasma and CSF by precipitation. Samples were analyzed using liquid chromatography (LC) with tandem mass spectrometric detection (MS/MS) using electrospray ionization. The standard curve range was from 1 to 1000 ng/mL. Results of the compounds described herein in this assay are illustrated in Table 7 below (3 and 10 mg/kg dose). Statistics were determined by planned comparison t-tests.

$K_{p,uu}$ is defined as the concentration ratio of unbound drug in CSF to unbound drug in plasma. Unbound drug in plasma (or free plasma concentration) is calculated by multiplying the total plasma concentration by the unbound fraction as determined by plasma protein binding. The CSF concentration is then divided by the free plasma concentration to determine the $K_{p,uu}$. (See e.g., Di et al., *J. Med. Chem.*, 56, 2-12 (2013)).

TABLE 7

CSF PK properties of select compounds described herein (Example 7) at a 3 and 10 mg/kg dose.

| Compound, Dose | CSF Conc. (nM @ 1 h) | CSF Conc. (nM @ 6 h) |
|---|---|---|
| I-1, 0 mg/kg | 3.9 | 4.7 |
| I-1, 3 mg/kg | 7.2* | 6.7 |
| I-1, 10 mg/kg | 14.8** | 13.8* |

*p < than 0.05 vs. vehicle;
**p < than 0.01 vs. vehicle

Conclusions.

Acute dosing of 3 mg/Kg Compound I-1 P.O. in rat induced a significant increase of cGMP in rat CSF 1 h after dosing. Acute dosing of 10 mg/Kg Compound I-1 P.O. in rat induced a significant increase of cGMP in rat CSF 1 h and 6 h after dosing.

Example 8: Evaluation of Compounds of the Invention on Synaptic Transmission and Plasticity Impairments in R6/2 Mice Hippocampal Slices Improvements in synaptic transmission and plasticity, as measured by long term potentiation (LTP), is believed to indicate the potential of a compound to enhance memory. LTP is an electrophysiological phenomena that is commonly referred to as the a cellular phenomenon driving learning and memory.

Protocol.

Preparation of Acute Mice Hippocampal Slices.

Experiments were carried out with 11 to 12 week-old R6/2 and WT mice provided by the Jackson Laboratory (USA). Hippocampal slices (350 µm thickness) were cut with a MacIlwain tissue chopper in an ice-cold oxygenated sucrose solution (Saccharose 250, Glucose 11, $NaHCO_3$ 26, KCl 2, $NaH_2PO_4$ 1.2, $MgCl_2$ 7, and $CaCl_2$ 0.5 in mM). The slices were incubated 1 hour at room temperature in ACSF of the following composition: Glucose 11, $NaHCO_3$ 25, NaCl 126, KCl 3.5, $NaH_2PO_4$ 1.2, $MgCl_2$ 1.3, and $CaCl_2$ 2 in mM. Then, the slices were let to recover for at least 1 h.

Slice Perfusion and Temperature Control.

During the experiments, the slices were continuously perfused with the ACSF (bubbled with 95% $O_2$-5% $CO_2$) at the rate of 3 mL/min with a peristaltic pump (MEA chamber volume: ~1 mL). Complete solution exchange in the MEA chamber was achieved 20 s after the switch of solutions. The perfusion liquid was continuously pre-heated at 37° C. just before reaching the MEA chamber with a heated-perfusion cannula (PH01, MultiChannel Systems, Reutlingen, Germany). The temperature of the MEA chamber was maintained at 37±0.1° C. with a heating element located in the MEA amplifier headstage.

Stimulation Protocols/Compound Application.

Input/Output (I/O) curve: from 100 to 800 µA, by 100 µA steps. The stimulus intensity was then set to a fixed value of 250 µA for the short- and long-term synaptic plasticity measurements.

Short-Term Plasticity Properties:

two pulses with a decreasing inter-stimuli interval (e.g. 300 ms, 200 ms, 100 ms, 50 ms, 25 ms) were applied. Compound application: fEPSP were recorded for 10 minutes in control conditions (to verify the baseline steadiness) followed by a 15-minute exposure to the compound (or 25 minutes in the presence of vehicle only for control slices). A second I/O protocol and paired-pulse protocol were applied, as described previously, in the continuous presence of the compound.

Long-Term Potentiation (LTP):

Following a 10-minute control period (in the presence of the compound or vehicle for control slices), LTP was induced by a 10×TBS. Potentiation of synaptic transmission was then monitored for an additional 60-minute period (in the continuous presence of the compound or vehicle for control slices).

Results

Comparison Between R6/2 and WT Mice.

I/O characteristics were significantly higher in R6/2 mice hippocampal slices when compared to their WT littermates, for the higher stimulation intensities (700 and 800 µA). Paired-pulse properties were in the same range for R6/2 and WT mice hippocampal slices, except for the 25 ms Inter-Stimulus Interval, for which facilitation was significantly larger for R6/2 mice. Long-Term Potentiation was significantly impaired (p value<0.0001, Two-way ANOVA) in hippocampal slices of R6/2 mice, when compared to age-matching WT mice.

Evaluation of 7 nM Compound I-1.

I/O characteristics were not significantly modified after the exposure to 7 nM Compound I-1 in R6/2 hippocampal slices, for all stimulus intensities. Paired-pulse properties were also in the same range before and after exposure to 7 nM of Compound I-1 in R6/2 mice hippocampal slices, and did not significantly differ for any of the ISI. Exposure to 7 nM Compound I-1 for 15 minutes, did not modify the fEPSP amplitude.

In WT mice hippocampal slices (control conditions), HFS triggered a potentiation of the evoked-response amplitudes that stabilized around 45% (fEPSP were increased by 46±5%, at end point). In R6/2 mice hippocampal slices (control conditions), HFS triggered a potentiation of the evoked-response amplitudes that stabilized around 15% (fEPSP were increased by 16±3%, at endpoint). After exposure to 7 nM Compound I-1, HFS triggered a potentiation of the evoked-response amplitudes that stabilized around 25% (fEPSP were increased by 26±6%, at endpoint). The potentiation observed after the exposure to 7 nM Compound I-1 did not significantly differ to the one recorded in control R6/2 slices (p value=0.0842, Two-way ANOVA). (FIG. 1).

Evaluation of 46 nm Compound I-1.

I/O characteristics were similar before and after the exposure to 46 nM Compound I-1 in R6/2 hippocampal slices, for all stimulus intensities. Paired-pulse properties were not significantly increased after exposure to 46 nM Compound I-1 in R6/2 mice hippocampal slices, for all of the ISI. Exposure to 46 nM Compound I-1, for 15 minutes did not modify the fEPSP amplitude in comparison with control slides.

Figure 2:
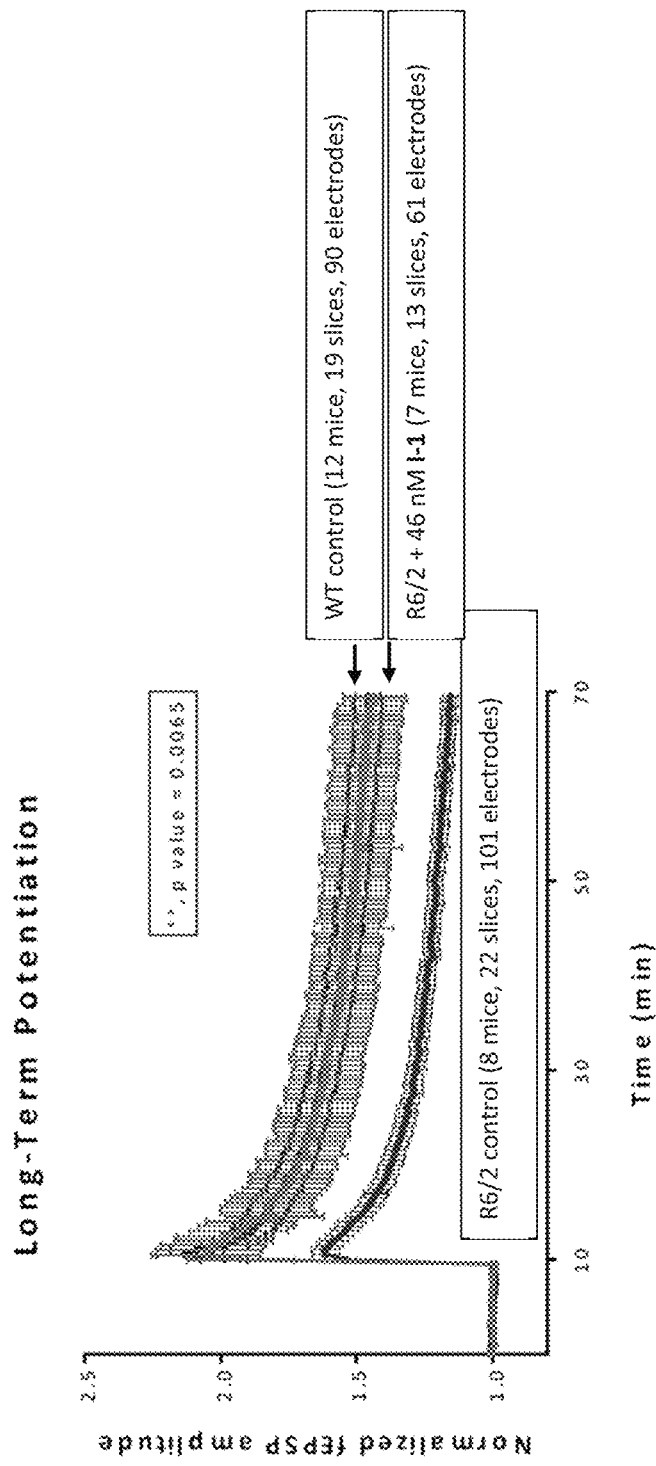
FIG. 2 is a plot of the long-term potentiation of wild type (WT) mice hippocampal slices (top curve, overlaps with middle curve), R6/2 mice hippocampal slices (bottom curve), and R6/2 mice hippocampal slices treated with 46 nM Compound I-1 (middle curve, overlaps with top curve).

In WT mice hippocampal slices (control conditions), HFS triggered a potentiation of the evoked-response amplitudes that stabilized around 45% (fEPSP were increased by 46±5%, at end point). In R6/2 mice hippocampal slices (control conditions), HFS triggered a potentiation of the evoked-response amplitudes that stabilized around 15% (fEPSP were increased by 16±3%, at endpoint). After exposure to 46 nM Compound I-1, HFS triggered a potentiation of the evoked-response amplitudes that stabilized around 45% (fEPSP were increased by 44±12%, at endpoint). The potentiation observed after the exposure to 46 nM Compound I-1 was significantly larger than the one recorded in control R6/2 slices (p value=0.0065, Two-way ANOVA). (FIG. 2)

Evaluation of 308 nm Compound I-1.

I/O characteristics recorded from R6/2 hippocampal slices were not significantly increased after exposure to 308 nM Compound I-1 for all stimulus intensities. Paired-pulse properties were significantly lower after exposure to 308 nM Compound I-1 for the 50 ms ISI only, in R6/2 mice hippocampal slices. The amplitude of fEPSP was slightly increased over the 15-minute exposure to 308 nM Compound I-1, when compared to the control R6/2 slides.

Figure 3:
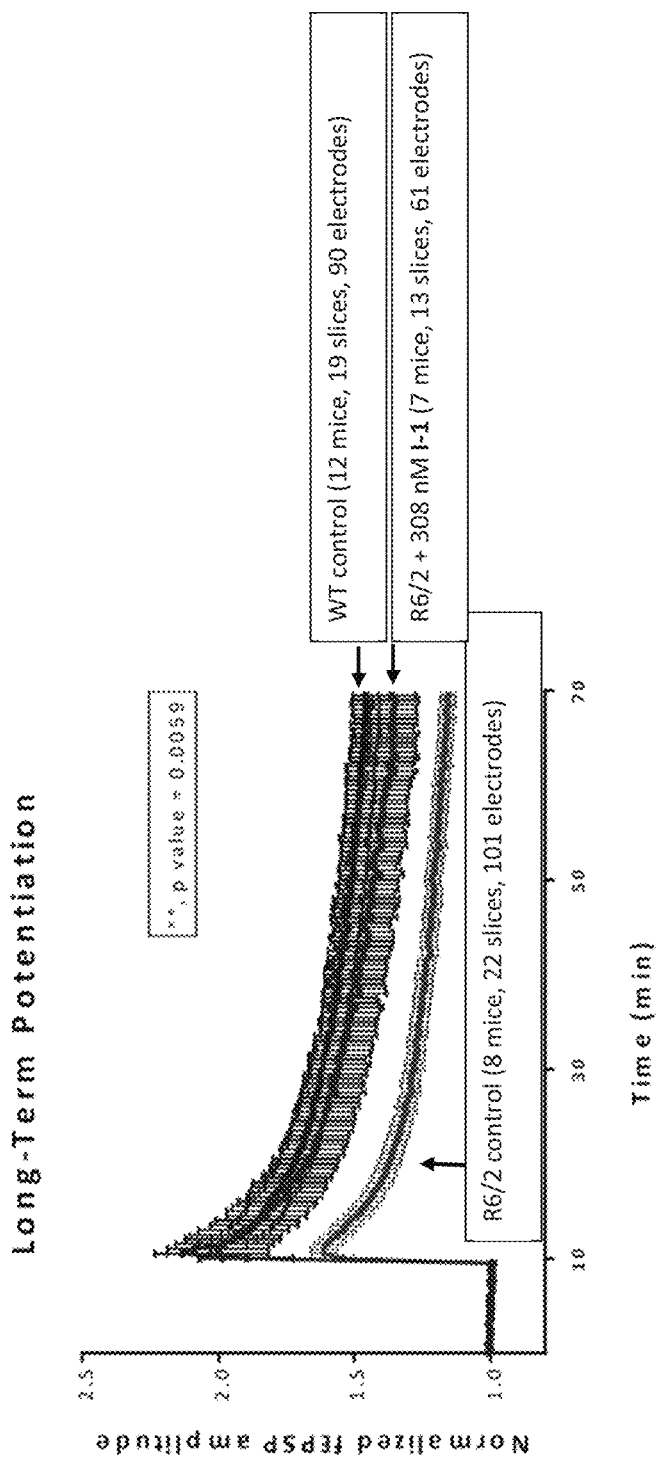
FIG. 3 is a plot of the long-term potentiation of wild type (WT) mice hippocampal slices (top curve, overlaps with middle curve), R6/2 mice hippocampal slices (bottom curve), and R612 mice hippocampal slices treated with 308 nM Compound I-1 (middle curve, overlaps with top curve).

In WT mice hippocampal slices (control conditions), HFS triggered a potentiation of the evoked-response amplitudes that stabilized around 45% (fEPSP were increased by 46±5%, at end point). In R6/2 mice hippocampal slices (control conditions), HFS triggered a potentiation of the evoked-response amplitudes that stabilized around 15% (fEPSP were increased by 16±3%, at endpoint). After exposure to 308 nM Compound I-1, HFS triggered a potentiation of the evoked-response amplitudes that stabilized around 35% (fEPSP were increased by 37±9%, at endpoint). The potentiation observed after the exposure to 308 nM Compound I-1 was significantly larger than the one recorded in control R6/2 slices (p value=0.0059, Two-way ANOVA). (FIG. 3)

Conclusions.

Although the highest concentration of Compound I-1 that was investigated (308 nM) slightly increased the amplitude of evoked-responses, none of the 3 concentrations displayed a significant effect on the overall 110 characteristics, in R6/2 mice hippocampal slices. None of the evaluated Compound I-1 concentrations (7 nM, 46 nM or 308 nM) displayed a significant effect on the short-term plasticity properties, as measured by paired-pulses with 25 ms to 300 ms ISI (with the exception of 308 nM Compound I-1, which significantly decreased the facilitation of paired pulses applied with a 50 ms ISI). Whereas 7 nM Compound I-1 failed to significantly rescue the LTP impairment recorded in R6/2 mice hippocampal slices, this compound completely restored the LTP deficit at 46 nM and 308 nM concentrations.

Example 9: Compound-Induced cGMP in Mouse Brain

Objective.

To determine the effect of different doses of a compound of the invention in cGMP response and compound concentration in different areas of the mouse brain (cortex, hippocampus, cerebellum and striatum) and compound concentration in blood Protocol.

Figure 5:
FIG. 5 is a picture of the brain of a mouse transferred using an ice-cold spatula to mouse brain matrix with coronal spacing for slicing at 1 mm intervals.

Mice (n=7-8 per experimental condition) were dosed PO with vehicle (1% hydroxypropyl methyl cellulose, 0.2% Tween80, 0.5% methyl cellulose) or 0.3, 1, 3 or 10 mg/Kg of Compound I-1 prepared in vehicle. Thirty minutes after dosing, under isoflurane anesthesia, the mouse was decapitated and the brain was removed and placed into an ice-cold petri dish containing slushy dissection solution (saturated with 95% $O_2$.5% $CO_2$). Using an ice-cold spatula, the brain was transferred to mouse brain matrix with coronal spacing for slicing at 1 mm intervals, as shown in FIG. 5 (not to scale, just a scheme).

The sliced brain was transferred back into petri dish containing slushy dissection solution with IBMX 0.5 mM (saturated with 95% $O_2$/5% $CO_2$). The dorsal striatum is dissected first, followed by the hippocampus second, followed by the medial prefrontal cortex third, and lastly, the cerebellum fourth. After each region is dissected the dissected tissue was immediately placed into an eppendorf that was placed on dry ice for the previous 30 minutes. Small pieces of tissue froze very fast, within 10 seconds approximately. After all regions were placed in an eppendorf, the eppendorfs were then snap frozen by immersion into liquid nitrogen. The whole blood sample was collected from the trunk area using mitra tips. Tissue samples were stored in the −80° C. and mitra tips at room temperature. cGMP and compound levels in brain and blood were determined by LC/MS; protein quantification of brain samples was determined using BCA protein assay kit.

Conclusion:

Acute dosing of 10 mg/Kg Compound I-1 P.O. in mice induced a significant increase of cGMP in all the mouse brain areas analyzed (hippocampus, cerebellum, cortex and striatum). (Tables 9a-d)

TABLE 9a

The concentration of cGMP in the mouse hippocampus normalized to protein concentration in the samples.

| Hippocampus | nM cGMP/µg protein | | | |
|---|---|---|---|---|
| Vehicle | 0.3 MPK I-1 | 1 MPK I-1 | 3 MPK I-1 | 10 MPK I-1 |
| 0.035359286 | 0.042545857 | 0.04302025 | 0.051901286 | 0.117125** |

**p < than 0.01 vs. vehicle

TABLE 9b

The concentration of cGMP in the mouse striatum normalized to protein concentration in the samples.

| STRIATUM | nM cGMP/µg protein | | | |
|---|---|---|---|---|
| Vehicle | 0.3 MPK I-1 | 1 MPK I-1 | 3 MPK I-1 | 10 MPK I-1 |
| 0.02185575 | 0.022608143 | 0.031235625 | 0.037185875 | 0.046120125* |

*p < than 0.05 vs. vehicle;

TABLE 9c

The concentration of cGMP in the mouse cerebellum normalized to protein concentration in the samples.

| CEREBELLUM | nM cGMP/µg protein | | | |
|---|---|---|---|---|
| Vehicle | 0.3 MPK I-1 | 1 MPK I-1 | 3 MPK I-1 | MPK I-1 |
| 0.473119429 | 0.319919286 | 0.457655 | 0.75244675 | 1.7957685**** |

****p < or = to 0.0001 vs. vehicle;

TABLE 9d

The concentration of cGMP in the mouse cortex normalized to protein concentration in the samples.

| CORTEX | nM cGMP/µg protein | | | |
|---|---|---|---|---|
| vehicle | 0.3 MPK I-1 | 1 MPK I-1 | 3 MPK I-1 | 10 MPK I-1 |
| 0.06765825 | 0.077611714 | 0.08063575 | 0.10810275 | 0.173364125* |

*p < than 0.05 vs. vehicle;

Example 10. Novel Object Recognition (NOR) Test

Objective.

To assess the efficacy of compounds of the invention in reversing memory disruption induced by MK-801 using the Novel Object Recognition (NOR) test in male Long Evans rats. The NOR is a test of recognition learning and memory retrieval, which takes advantage of the spontaneous preference of rodents to investigate a novel object compared with a familiar one (Ennaceur and Delacour, 1988). Studies indicated that the NOR procedure involves several brain regions, including perirhinal cortex (Ennaceur et al. 1996, 1997 and Aggleton et al. 1997) and the hippocampus (Wood et al. 1993 and Clark et al. 2000). The NOR test has been employed extensively to assess the potential cognitive-enhancing properties of novel test compounds. Because the NOR paradigm does not involve reward or noxious stimuli, it provides less confounding variables when being translated into analogous tests conducted in human clinical trials. In the present study, a memory saving model was used to test the novel compound—MK-801 (Dizocilpine), an uncompetitive antagonist of the NMDA receptor was used to cause deficit of recognition memory. Compounds of the invention were evaluated through its efficacy in reversing memory impairment.

Material and Methods.

Animals.

Adult male Long-Evans rats (275-299 gram at arrival from Envigo, Indianapolis, Ind.) were used in this study. Rats were placed in the experimental rooms and assigned unique identification numbers (tail marks). Rats were housed 2 per cage in polycarbonate cages with filter tops and acclimated for at least 7 days prior to testing. Animal room was maintained in a 12/12 h light/dark cycle (lights on at 07.00 EST), 22±1° C. and relative humidity at approximately 50%. Food and water were provided ad libitum. All animals were examined, handled and weighed prior to the study to assure adequate health and to minimize the non-specific stress associated with testing. Each animal was randomly assigned across the treatment groups. The experiments were conducted during the animal's light cycle phase.

Test Compounds.

The following compounds were used in this study:

MK-801 (0.1 mg/kg; Sigma-Aldrich) was dissolved in saline and injected IP 15 min prior to NOR training.

Galantamine (1 mg/kg; Tocris) was dissolved in saline and injected IP 15 minutes prior to training.

Compound I-1

(0.01, 0.1, and 1 mg/kg) was oral administrated 60 minutes prior to training. The dose volume was 4 ml/kg Experimental Procedures.

NOR test was conducted in an open-field arena (40×40 cm) placed in a sound-attenuated room under dimmed lighting. Each rat was tested separately and care was taken to remove olfactory/taste cues by cleaning the arena and test objects with 70% alcohol between trials and rats. All training and testing trials were video-taped and scored by an observer blind to treatments.

On Days 1 and 2, rats were allowed to freely explore the arena (no objects inside) for a 5-minute habituation period. On Day 3 (training and testing day), rats were administered vehicle (saline), galantamine or compound solutions followed by MK-801 or vehicle (saline). After the pretreatment time, each animal was placed into the test arena in the presence of two identical objects. Each rat was placed in the arena facing the same direction at the same position, and the time spent actively exploring the objects during a 3-minute training period (T1) was recorded. The rat was returned to its home cage following training. NOR test (T2) was conducted 1 hours after T1. Each rat was placed back into the test arena in the presence of one familiar object and one novel object for 5 minutes, and the time spent exploring both objects was recorded during 0-1, 0-3 and 0-5 min time ranges. The presentation order and position of the objects (left/right) in T2 was randomized between rats to prevent bias from order or place preference.

Statistical Analysis.

Data of NOR test (T2) were expressed as Recognition Index, which is defined as the ratio of the time spent exploring the novel object over the total time spent exploring both objects (Novel/(Familiar+Novel)×100%) during the test session. Data were analyzed by using one-way ANOVA followed by Fisher's LSD post hoc test on 0-1, 0-3 and 0-5 minute time range separately, with significance set at $P<0.05$. Animals with overall object exploration time less than 10 seconds in the 5 min test session were eliminated; rats with recognition index above 90% or below 30% were also eliminated because they suggest strong (non-memory) bias between two objects. And then statistical outliers that fell above or below two standard deviations from the mean were removed from the final analysis. With these criteria, 1-3 rats were eliminated from each experimental group (N=15-16) and were excluded from statistical analyses for all time range (0-1, 0-3, and 0-5 minute).

Results.

None of the rats in this study showed obvious side effects at any dose. Rats maintained normal vigilance, activity and exploration level to objects. ANOVA showed significant main treatment effects on Recognition Index during 0-1 min time range [$F(8,121)=2.451$, $P<0.05$]. Post hoc test showed that MK-801 0.1 mg/kg caused a strong memory deficit, with a Recognition Index approaching chance level (50%). Galantamine (1 mg/kg) and Compound I-1 at 1 mg/kg significantly reversed MK-801-induced memory deficits (Ps<0.01 and Ps<0.05, respectively, compared to Vehicle/MK-801group). During 0-3 minute time range (Table 10), ANOVA found a significant main treatment effect [$F(8,121)=3.404$, $P<0.01$]. Post hoc test showed that MK-801 0.1 mg/kg caused a strong memory deficit, with a Recognition Index approaching chance level (50%). Galantamine (1 mg/kg) and Compound I-1 at 0.1 and 1 mg/kg significantly reversed MK-801-induced memory deficits (Ps<0.001, Ps<0.01 and P<0.05, respectively, compared to Vehicle/MK-801group). Similarly, ANOVA showed a significant main treatment effect during 0-5 minute time range [$F(8,121)=3.179$, $P<0.01$]. Post hoc test showed that MK-801 at 0.1 mg/kg caused a strong memory deficit, with a Recognition Index approaching chance level (50%). Galantamine (1 mg/kg), and Compound I-1 at 1 mg/kg significantly reversed MK-801-induced memory deficits (P<0.001, P<0.01 and Ps<0.05, respectively, compared to Vehicle/MK-801group).

TABLE 10

Summary of Recognition Index Measurements (0 to 3 minute time bin)

| Treatment | n-number | Mean | Standard Deviation | Standard Error of the Mean | Statistical Analysis (p-value) |
|---|---|---|---|---|---|
| Vehicle + Saline Control | 13 | 72.4 | 6.8 | 1.9 | <0.001 |
| Vehicle + MK-801 | 12 | 54.1 | 7.8 | 2.3 | NA |
| Galantamine + MK-801 | 14 | 66.2 | 9.3 | 2.5 | 0.002 |
| I-1 (0.1 mg/kg) + MK-801 | 13 | 60.1 | 10.0 | 2.8 | 0.133 |
| I-1 (1 mg/kg) + MK-801 | 16 | 64.8 | 12.0 | 3.0 | 0.005 |
| I-1 (10 mg/kg) + MK-801 | 15 | 66.8 | 9.5 | 2.5 | 0.001 |

Statistical comparisons are made to the "Vehicle+MK-801" treatment group. Statistical significance is deemed when p value is less than 0.005.

Summary.

Reference compound galantamine 1 mg/kg significantly reversed the cognitive deficit induced by MK-801 0.1 mg/kg, suggesting the validity of the test. Compound I-1 at 0.1 mg/kg and 1 mg/kg showed clear efficacy in saving the NOR memory after treatment of MK-801, suggesting the compound possesses properties of memory enhancement.

Example 11—Brain Activation in Rats as Measured by fMRI-BOLD

Objective.

Functional magnetic resonance imaging or functional MRI (fMRI) is a functional neuroimaging procedure using MRI technology that measures brain activity by detecting changes associated with blood flow. This technique relies on the fact that cerebral blood flow and neuronal activation are coupled. When an area of the brain is in use, blood flow to that region also increases. Awake rats were studied by fMRI to assess changes ("fingerprint") in brain activity following a single intravenous administration of a compound of the invention Experimental Design.

24 male Sprague-Dawley rats weighing from 275-350 g were used. Following acclimation, the animals were placed in the restrainer and positioned in the magnet. Catheters were placed in each animal to allow for remote dosing when the animals were in the magnet. Scans were acquired continuously for 5 minutes prior to administration of either a vehicle or a compound of the invention to establish a baseline for the brain activity. Following the 5-minute baseline period, either the vehicle or the compound of the invention was administered to the rat and scans were acquired continuously for 30-45 minutes.

Study Design.

| Group No | N | Treatment | Dose (mg/kg) | ROA | Imaging |
|---|---|---|---|---|---|
| 1 | 10 | Vehicle | — | IV @ $ED_{50}$ | Images were acquired continuously starting 5 min prior to dosing and for 30 minutes post-dosing |
| 2 | 10 | I-1 | Defined by $EC_{50}$ | | |
| 3 | 10 | Non-CNS penetrant sGC compound | Defined by target BP response | | |

Summary.

Figure 4:
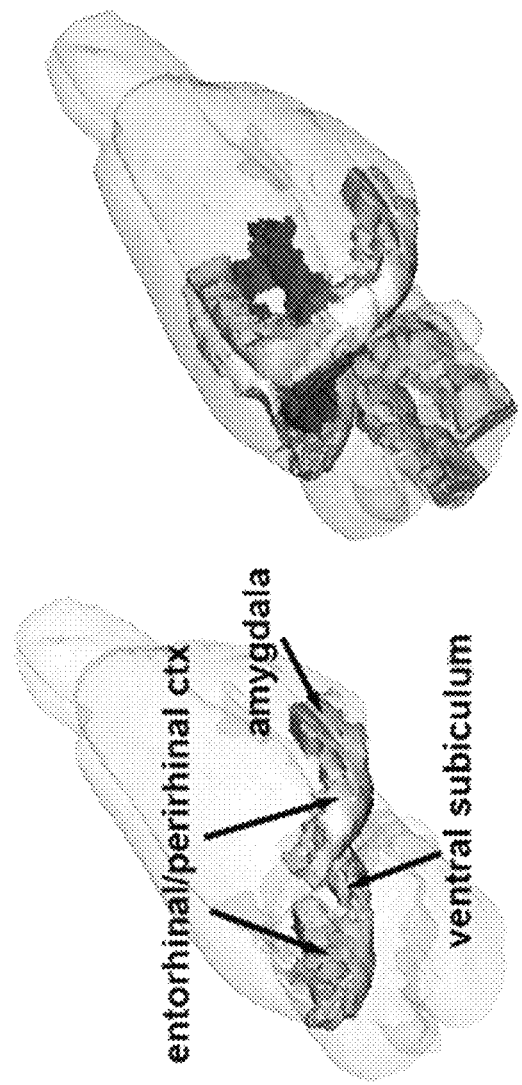
FIG. 4 is a picture of the brain of a rat treated with a peripherally restricted sGC stimulator (left) and a picture of the brain of a rat treated with a compound of the invention (right).

As shown in FIG. 4, a greater region of the brain is activated when the animal is administered a compound of the invention (Compound I-1) (FIG. 4, right,) then when the animal is dosed with a sGC stimulator that is peripherally restricted (i.e., a compound that does not enter the CNS) (FIG. 4, left). Specifically, when dosed with a compound of the invention, brain regions associated with memory (cortical transition areas, thalamus, and ventral hippocampus), and arousal (the reticular activating system) were activated.

Example 12—pCREB Phosphorylation in Rat Primary Neurons

Objective.

To assess the ability of Compound I-1 to activate cAMP response element-binding protein (CREB) in rat primary neurons. CREB is a cellular transcription factor. It binds to DNA sequences called cAMP response elements (CRE), and regulates transcription of the downstream genes (See Bourtchuladze R, et al., Cell 1994; 79 (1): 59-68). CREB has a well-documented role in neuronal plasticity and long-term memory formation in the brain and has been shown to be integral in the formation of spatial memory (See Silva A J, et al., Annual Review of Neuroscience 1998; 21: 127-148). CREB proteins are activated by phosphorylation of Serine 133 by various kinases, including cAMP-dependent protein kinase or Protein Kinase A (PKA), cGMP-dependent protein kinase or Protein Kinase G (PKG), and Ca2+/calmodulin-dependent protein kinases. (See Shaywitz A J and Greenberg M E, Annual Review of Biochemistry 1999; 68 (1): 821-861 and Wong J C, et al., J Cell Biochem 2012: 113(11):3587-98). Stimulation of CREB could have therapeutic benefits for diseases in which cognition, neuronal plasticity, and or neuronal function is impaired.

Materials and Methods.

Compounds.

Compound I-1 was dissolved in DMSO as a 10 mM solution and stored at −20° C. To achieve desired test concentrations, stock concentrations were serially diluted into DMSO and then diluted to the appropriate concentration in assay buffer.

Rat Primary Neurons Culture.

Neurons were isolated from Sprague Dawley rat embryos on embryonic day 18 (E18). Approximately 10 embryos were obtained from each rat, and whole brains were isolated from the embryos. Hippocampus and cortex were dissected from the brains under a stereoscopic microscope using two pairs of fine tweezers. The meninges were carefully removed. After dissection, the tissues were chopped and washed gently once with 10 mL of $Ca^{2+}$ and $Mg^{2+}$ free Hank's solution (HBSS, Corning cat #21-022-CM) in a 15-mL conical tube. After washing, 5 mL of a solution of 0.25% trypsin (Invitrogen cat #15090-046) and 0.1% deoxyribonuclease I (DNase I, Sigma cat #DN-25) were added to the tissues in the tube, which were then incubated at 37° C. for 15 min. After incubation and digestion with the enzymes, tissues were washed three times with ice-cold HBSS. After washing, 3 mL of a solution of 0.1% of DNase I was added to the tube and the tissues were slowly pipetted using a glass Pasteur pipette 12 times, and then centrifuged at 500×g for 10 min. The cell pellet was resuspended in the culture medium (Neurobasal medium, Gibco cat #21103-049), 2% of B27 supplement (Gibco Cat #17504-044), 0.5 mM L-glutamine (Corning cat #25-005-Cl), 25 µM L-glutamic acid (Sigma cat #G1251) and 1% penicillin/streptomycin (Gibco cat #15070-063)). Subsequently, the cell suspension was plated into poly-L-lysine coated 96-well plates at 100,000 cells/well. Twenty-four h after plating, half of the culture medium was removed and replaced with culture medium as described above but without glutamic acid. Cells were maintained in a 37° C. humidified incubator with 5% $CO_2$ and used between days 6-10.

Assay Conditions.

For each test concentration, Compound I-1 was diluted in 100% DMSO to 100-fold of its final assay concentration. Immediately prior to the assay, Compound I-1 was diluted 10-fold into HBSS (containing calcium and magnesium) (10× the final assay concentration) containing 100 µM DETA-NONOate (10× the final assay concentration). Medium was removed and cells were washed once with 90 µL HBSS (Corning cat #21-023-CV). Cells were then incubated with 90 µL HBSS for 30 min at 37° C. 10 µL from the test article/HBSS/DETA-NONOate plate was added to the cells, which were incubated for additional 30 min at 37° C. Final DMSO concentrations were 1%, final DETA-NONOate concentration was 10 μM; and final Compound I-1 concentrations were 10,000 nM, 1000 nM, 100 nM, 10 nM, 1 nM, 0.1 nM, 0.01 nM, and 0.0 nM. Medium was removed and cell were lysed and assay was performed according to Cisbio protocol (phospho-CREB (Ser133) catalog #64CREPEG) and the plate was read using Envision instrument (PerkinElmer).

Data Analysis.

Data were analyzed with a 4-parameter fit (log(agonist) vs. response–variable slope) using GraphPad Prism Software v.7. The $EC_{50}$ was interpolated from the curve fit and is defined as the concentration at which Compound I-1 elicits 50% of its maximal response.

Results.

Phosphorylation of CREB at Ser133 stimulated by Compound I-1 was concentration-dependent, with an $EC_{53}$ of 3.0 nM. The 95% confidence interval ranged from 0.5 nM to 17.8 nM.

Example 13—Evaluation of Compounds of the Invention in Pain Models and Tests

Objective.

To evaluate the efficacy of compounds of the invention in acute and tonic pain, inflammatory pain, post-operative pain, and visceral pain.

Materials and Methods: Acute and Tonic Pain

Paw Pressure Test.

Static mechanical hyperalgesia is measured. This test requires the application of an increasing pressure on the hind paws between a flat surface and a blunt pointer. To evaluate the analgesic action of a compound, one hind paw of the animal was inflamed by an injection or injured by ligation, while the other hind paw was not injured or inflamed. The apparatus exerted a steadily increasing force on the hind paws. The reaction threshold was determined as the pressure (g) required to elicit paw withdrawal and/or vocalization. The animals were gently handled by the experimenter and static mechanical hyperalgesia were assessed two times for both hind paws.

Tail Flick Test.

A radiant heat was applied on the tail. When the rat felt discomfort, it reacted by a sudden tail movement (tail flick) which automatically stopped the stimulation and the timer for the measurement by the animal reaction time or nociceptive reaction latency (period from the beginning of the stimulation until detection of the response of the animal). A cut-off was previously fixed at 10 sec in order to prevent tissue damage.

Acetic Acid Test.

Abdominal contraction was induced by intraperitoneal injection of 0.6% acetic acid solution in rats (10 mL/kg). The number of writhing (a twisting or contorting of the body due to pain) was recorded from the $5^{th}$ to the $15^{th}$ minute after injection.

Formalin Test.

2.5% formalin solution was injected by subplantar route into the right hind paw. Scoring of pain behavior was performed in rats for 36 minutes every 3 minutes according to the following scores:
0=normal behavior of the injected hind limb to support the body
1=slight touching of the injected paw on the floor to lightly support or not support the body
2=total withdrawal of the injected paw
3=licking, biting or shaking of the injected paw Materials and Methods: Inflammatory Pain Carrageenan.

Induction: Three hours before assessment of the nociceptive threshold using the paw pressure test 100 μL of a 2% carrageenan suspension was injected into the plantar aspect of the right hind paw. The Paw Pressure test was then conducted as described above.

Kaolin.

Induction: In rats, unilateral arthritis was induced by an intra-articular injection of a 10% kaolin suspension into the knee joint of the right hind paw under gas anesthesia (3.5% isoflurane/3 L/min). Gait score: The gait score will be evaluated 3 h 30 min after kaolin administration by:
0: normal gait
1: mid disability
2: intermittent raising of the paw
3: elevated paw Materials and Methods. Post-Operative Pain: Brennan Model.

Surgery:

Surgery was done under gas anesthesia (2.5% isoflurane/3 L/min). For all rats, the plantar aspect of the left hind paw was exposed and a 1 cm longitudinal incision was made using a surgical blade, through the skin and fascia of the plantar aspect of the foot, starting 0.5 cm from the proximal edge of the heel and extending toward the toes. The plantaris muscle was elevated and incised longitudinally whereas the insertions remained intact. After hemostasis with gentle pressure, the skin was stitched up with two sutures. After surgery, animals recovered in their cages.

Electronic Von Frey Test:

Tactile allodynia was assessed using the electronic Von Frey test 24 h after surgery. The test requires the application of an increasing pressure onto the plantar aspect of the hind paws. The apparatus exerted a steady force on the hind paws. Reaction thresholds were determined as the pressure (g) required to elicit paw withdrawal. Each reaction threshold measurement was repeated three times for both hind paws with intervals of approximately 2 to 3 mins.

The results for acute and tonic pain, inflammatory pain, and post-operative pain models and test for animals treated with 10 mg/kg of Compound I-1 PO were significant and are presented below.

Results.

| Pain Model | Model-test | Compound I-1, p.o., 10 mg/kg % of activity vs. vehicle | Internal Reference Reference ID | % of activity vs. vehicle |
|---|---|---|---|---|
| Acute and Tonic Pain | Healthy rats-paw pressure test | −6% | Morphine 4 mg/kg s.c. | 69% |

-continued

| Pain Model | Model-test | Compound I-1, p.o., 10 mg/kg % of activity vs. vehicle | Internal Reference Reference ID | % of activity vs. vehicle |
|---|---|---|---|---|
| | Healthy rats-tail flick test | 25% | Morphine 4 mg/kg s.c. | 66% |
| | Acetic acid test-Abdominal cramps | 7% | (—) U50, 488 H 3 mg/kg s.c. | 100% |
| | Formalin test-Score (early phase) | 57% | Morphine 4 mg/kg s.c. | 57% |
| | Formalin test-Score (late phase) | 32% | Morphine 4 mg/kg s.c. | 38% |
| Inflammatory Pain | Carrageenan-paw pressure test | 38% | Indomethacin 30 mg/kg p.o. | 100% |
| | Kaolin-gait score | 40% | Indomethacin 30 mg/kg p.o. | 58% |
| Post-operative Pain | Brennan model-Electronic Von Frey test | 31% | Morphine 4 mg/kg s.c. | 88% |

Testing: 120 minutes after treatment. N=4/model/test. Results are expressed for each group as a percentage of activity calculated from the mean value of the vehicle-treated animals and compared to naïve animals, control paw, or cut-off value, depending on the test.

Conclusions.

Compound I-1 demonstrated effects in the formalin test for acute pain. Compound I-1 demonstrated effects in the carrageenan and kaolin models of inflammatory pain. Compound I-1 demonstrated effects in the test for post-operative pain.

Example 14. Antihyperalgesic Effects of Single and Repeated Administrations of Compound I—in a Rat Model of Diabetic Neuropathy (STZ Model)

Objective.

To assess the antihyperalgesic effects of single and repeated administrations of a compound of the invention in a model of diabetic neuropathy (streptozotocin model) using the paw pressure test in rats. Gabapentin will be used as internal comparator. Morphine HCl will be used as a reference substance to validate the assay.

In humans, one of the leading causes of neuropathic pain is diabetic neuropathy. Several diabetic animal models are available but the most commonly used for the study of pain is the streptozotocin model. In this experimental model, neuropathy is reproduced in rats using a single intraperitoneal injection of streptozotocin which induces diabetes and consequently hyperalgesia and allodynia (See Rakieten N et al., Cancer Chemother, 1963 (Rep.29):91). Seven days later (D7), diabetic animals present a significant increase in glycemia associated with weight loss, polydipsia and polyuria. Animals develop a mechanical hyperalgesia which can be measured after Day 18 using a mechanical nociceptive stimulation (paw pressure test) (See Randall L O and Selitto J J, Arch Int Pharmacodyn, 1957(111):409-419).

Materials

Animals.

Seventy (70) male Sprague-Dawley rats (SPF status, Janvier, France), weighing 210-300 g the day of diabetes induction were used. Rats were housed in a temperature (20-24° C.) and relative humidity (45%-65%) controlled room and acclimated to an artificial day/night cycle of 12 hours light (6.30 a.m. to 6.30 p.m.)/12 hours darkness. Rats had free access to tap water and were fed ad libitum with pelleted complete diet (reference A04, S.A.F.E.). Animals were housed 3 per cage (cages Type E) and were acclimated for a period of at least 5 days before any testing. Each rat was identified by tail markings. Based on the SPF status of the animal facilities, there was no reason to expect that contaminants were present in the food, water or bedding, at levels capable of interfering with the results of the tests.

Reagents.

Streptozotocin (STZ, Sigma-Aldrich) was extemporaneously prepared as a solution in Citrate (Citric acid trisodium salt, Sigma-Aldrich) buffer 1 mM pH 4-4.5 (in water for injection). 0.9% NaCl was used as vehicle for Gabapentin (Zhejiang Excel pharma Co. Ltd.), Morphine HCl (Francopia) and Compound I-1. Insulin (Sanofi-Aventis) was prepared at 10 UI/ml in 0.9% NaCl Equipment.

Accu-Chek© (Roche Diagnostics S.A., France) and Accu-Chek® tests strips (Roche Diagnostics S.A., France) was used to measure the glycemia. Ugo Basile Analgesimeter (Ugo Basile, Italy) will be used for the paw pressure test.

Data Processing.

SigmaStat software version 3.5 (SPSS Science Software, Erkrath, Germany) Lab X direct software version 2.4 (Mettler Toledo, France)

Methods.

Pain Test.

Static mechanical hyperalgesia was assessed using the Paw Pressure test or Randall & Selitto test (See Randall L O and Selitto J J, Arch Int Pharmacodyn, 1957(111):409-419, the teaching of which are incorporated herein by reference). This test requires the application of an increasing pressure on the hind paws between a flat surface and a blunt pointer. This test is usually used with animals with one hind paw inflamed by an injection or injured by ligation, and one normal hindpaw, to evaluate compounds for analgesic action. The apparatus exerts a steadily increasing force and reaction threshold is determined as the pressure (g) required to elicit paw withdrawal and/or vocalization. In the experiment, animals were gently handled by the experimenter and static mechanical hyperalgesia will be assessed. Each reaction threshold was measured for both hind paws.

Experimental Design.

Seven experimental groups of 10 rats each will be used:
Group 1: Sham animals (Citrate buffer)/Vehicle, p.o., solution, daily from Day 18 to Day 21 (D18 to D21)
Group 2: STZ (75 mg/kg, i.p.)/Vehicle, p.o., solution, daily from D18 to D21
Group 3: STZ (75 mg/kg, i.p.)/Compound I-1 (1 mg/kg, p.o.), solution, daily from D18 to D21
Group 4: STZ (75 mg/kg, i.p.)/Compound I-1 (3 mg/kg, p.o.), solution, daily from D18 to D21
Group 5: STZ (75 mg/kg, i.p.)/Compound I-1 (10 mg/kg, p.o.), solution, daily from D18 to D21
Group 6: STZ (75 mg/kg, i.p.)/Gabapentin (100 mg/kg, p.o.) in 0.9% NaCl, solution, acute on testing days (D18 and D21)
Group 7: STZ (75 mg/kg, i.p.)/Morphine (4 mg/kg, s.c.) in 0.9% NaCl, solution, acute on testing days (D18 and D21)
Vehicle, Compound I-1 were orally administered at 5 ml/kg. Gabapentin was orally administered at 10 ml/kg. Morphine HCl was subcutaneously administered (5 ml/kg). Doses are expressed in terms of free active substance. Dosing and testing were performed in a random order by a blinded experimenter except for the Sham and the Morphine-treated groups.

Procedure.

Induction.

Chronic peripheral neuropathy was induced by a single intraperitoneal injection of Streptozotocin (75 mg/kg, i.p.) on D0. Six experimental groups were treated with streptozotocin and one will be treated with Citrate buffer 1 mM (vehicle of streptozotocin) after Glycemia measurement. On D7, glycemia was measured and rats having level>250 mg/dl were treated subcutaneously with Insulin (Lantus®, 2 IU/rat), three times a week with injections every two days from D7-8 to D14, on D18 at the end of the day and on D20 to prevent excessive cachexia. On D7, animals with a glycemia<250 mg/dl were treated again with Streptozotocin (75 mg/kg, i.p.). Glycemia was measured on D14 and rats having level>250 mg/dl were treated subcutaneously with Insulin (Lantus®, 2 IU/rat), three times a week with injections every two days from D14 to D19.

Behavioral Testing.

STZ animals are selected (baseline) on D18 and tested (animal dosing and behavioral test) on D18 and D21. The time course was as follows:

On Day 0 (D0), glycemia was measured before diabetes induction by injection of streptozotocin (75 mg/kg, i.p.) to select animals meeting the inclusion criteria (glycemia<150 mg/dl).

On D7 and on D18, glycemia was measured in to select animals with a glycemia higher than 250 mg/dl (except for the Group #1 sham animals).

On D18, nociceptive reaction thresholds (vocalization or paw withdrawal) was measured in all groups in order to select diabetic animals meeting the inclusion criteria: 20 g<paw withdrawal threshold<240 g. Sham animals with a paw withdrawal threshold included between 280 g and 520 g for both hind paws were selected. Animals having a body weight<200 g or >400 g were excluded from the study.

On D18 vehicle, Compound I-1, gabapentin and morphine will be given (T0). The antihyperalgesic effect of the vehicle, Compound I-1, gabapentin and morphine were evaluated on both hind paws using the Paw pressure test 60, 120, 180, and 240 min post drug administration. Morphine-treated animals were also tested 30 min after administration, but these data were not used as morphine showed significant antihyperalgesic effects 60 min after treatment.

Rats from groups 1 to 5 received a daily treatment on D19, D20 and D21.

On D21, glycemia and nociceptive thresholds were measured before the daily treatment in all groups. Vehicle, Compound I-1 gabapentin and morphine were given (T0). The antihyperalgesic effect of the morphine was evaluated 30 min post administration using the Paw pressure test and 120 min post vehicle, Compound I-1, gabapentin and morphine administration.

Data Presentation and Statistical analysis. Results are expressed as:

The paw withdrawal threshold (mean±s.e.m.) in grams of contact pressure for each group, calculated from individual paw withdrawal thresholds. The percentage of variation of the paw withdrawal threshold calculated from the mean value of the vehicle-treated group.

To determine a statistical effect of the test substance(s) and the reference substance, data was analyzed by a parametrical or non-parametrical test depending on the normal distribution of the results. The significance level is indicted below.

Results.

On D18, at 0 minutes all the groups treated with STZ had hyperalgesia with nociceptive threshold around 200 g as compared to normal rats with nociceptive threshold approximately 350 g. At 60 min following administration of the substance (i.e., vehicle, Compound I-1 at 1, 3, or 10 mg/kg, gabapentin, or morphine), the nociceptive threshold for gabapentin (272±6.6, $p<0.01$), morphine (420±35 $p<0.001$) and Compound I-1 at 10 mg/kg (328±32.6 $p<0.001$) were statistically different demonstrating efficacy as compared to the vehicle-only treated group. Similarly, at 120 min, the nociceptive threshold for gabapentin (302±17.7, $p<0.001$), morphine (317±27.6 $p<0.001$) and Compound I-1 at 10 mg/kg (387±30.2 $p<0.001$) were statistically different and efficacious as compared to the vehicle-only treated group. By 180 min, only the nociceptive threshold for Compound I-1 at 10 mg/kg (319±23.1 $p<0.001$) was efficacious and statistically different as compared to the vehicle-only treated group. By 240 minutes post-administration, no group was statistically significant from the vehicle. On D21, at baseline prior to the administration of the substance, only the nociceptive threshold for Compound I-1 at 10 mg/kg (259±25.6 $p<0.01$) was statistically different as compared to the vehicle-only treated group indicating anti-hyperalgesic efficacy was still present at Cmin. By 120 min, after dosing at D21, the nociceptive threshold for gabapentin (274±19.2, $p<0.01$), morphine (283±16.7 $p<0.001$) and Compound I-1 at 10 mg/kg (346±20.5 $p<0.001$) were statistically different and efficacious as compared to the vehicle-only treated group.

Conclusion.

Compound I-1 demonstrated an anti-hyperalgesic response when tested at 10 mg/kg in the STZ model of diabetic neuropathy. The effect in pain was observed acutely for up to 3 hours at levels at least comparable to morphine or gabapentin. After 3-days of dosing compound I-1 demonstrated efficacy in pain when tested at Cmin indicating a long-term effect. Also, when tested after 4-days of dosing, compound I-1 maintained its efficacy in the STZ model of neuropathic pain.

Various embodiments of the invention can be described in the text below. As explained supra, it is to be understood that pharmaceutically acceptable salts are included in these embodiments, even though the phrase "pharmaceutically acceptable salt" is not written.

[1]. A compound of Formula I.

[2]. A compound of [1] above, or according to other embodiments of the invention, wherein W is a ring B and the compound is one of Formula IIB.

[3]. A compound of [1] or [2] above, or according to other embodiments of the invention, wherein n is an integer selected from 1 or 2 and each $J^B$ is independently selected from halogen, a $C_{1-4}$ alkyl, $—OR^B$ or $—OR^{B1}$.

[4]. A compound of [1], [2] or [3] above, or according to other embodiments of the invention, wherein n is 1.

[5]. A compound of [1], [2] or [3] above, or according to other embodiments of the invention, wherein n is 2.

[6]. A compound of [1], [2], [3], [4] or [5] above, or according to other embodiments of the invention, wherein each $J^B$ is independently selected from halogen atoms.

[7]. A compound of [1], [2], [3], [4], [5] or [6] above, or according to other embodiments of the invention, wherein each $J^B$ is independently selected from fluoro or chloro.

[8]. A compound of [1], [2], [3], [4], [5], [6] or [7] above, or according to other embodiments of the invention, wherein each $J^B$ is fluoro.

[9]. A compound of [1], [2], [3], [4] or [5] above, or according to other embodiments of the invention, wherein each $J^B$ is a $C_{1-4}$ alkyl.

[10]. A compound of [1], [2], [3], [4], [5] or [9] above, or according to other embodiments of the invention, wherein each $J^B$ is selected from ethyl or methyl.

[11]. A compound of [1], [2], [3], [4], [5], [9] or [10] above, or according to other embodiments of the invention, wherein each $J^B$ is methyl.

[12]. A compound of [1], [2], [3], [5], [6] or [7] above, or according to other embodiments of the invention, wherein one $J^B$ is fluoro and the other $J^B$ is chloro.

[13]. A compound of [1] or [2] above, or according to other embodiments of the invention, wherein n is 0.

[14]. A compound of any one of [1] to [13] above, or according to other embodiments of the invention, wherein ring B is phenyl.

[15]. A compound of [1] to [3], [6] to [12], or [14] above, or according to other embodiments of the invention, wherein n is 1 or 2.

[16]. A compound of [1] to [12], [14] or [15] above, or according to other embodiments of the invention, wherein a $J^B$ is ortho to the attachment of the methylene linker between ring B and the core of the molecule, and the $J^B$ is halogen.

[17]. A compound of [1] to [13], [15] or [16] above, or according to other embodiments of the invention, wherein ring B is a 6-membered heteroaryl ring.

[18]. A compound of [1] to [13], or [15] to [17] above, or according to other embodiments of the invention, wherein ring B is a pyridyl ring.

[19]. A compound of [1] to [13], or [15] to [17] above, or according to other embodiments of the invention, wherein ring B is a pyrimidinyl ring.

[20]. A compound of [1] above, or according to other embodiments of the invention, wherein W is absent and the compound is one of Formula IIA.

[21]. A compound of [1] or [20] above, or according to other embodiments of the invention, wherein $J^B$ is a $C_{1-4}$ alkyl chain, optionally substituted by up to 5 instances of fluorine.

[22]. A compound of [1], [20] or [21] above, or according to other embodiments of the invention, wherein $J^B$ is a $C_{1-2}$ alkyl chain, optionally substituted by up to 5 instances of fluorine.

[23]. A compound of [1], [20], [21] or [22] above, or according to other embodiments of the invention, wherein $J^B$ is an ethyl chain, optionally substituted by 3 instances of fluorine.

[24]. A compound of [1], [20], [21] or [22] above, or according to other embodiments of the invention, wherein $J^B$ is an ethyl chain, optionally substituted by 5 instances of fluorine.

[25]. A compound of any one of [1] to [24] above, or according to other embodiments of the invention, wherein G, Z and Q are each N.

[26]. A compound of [1] to [19], or [25] above, or according to other embodiments of the invention, wherein the compound is one of Formula III, or any of its tautomers thereof.

[27]. A compound of any one of [1] to [26] above, or according to other embodiments of the invention, wherein $R^{11}$ is H, $NR^{a2}R^{b2}$, $—C(O)NR^{a2}R^{b2}$, $—C(O)R^{15a}$, $—SO_2R^{b2}$, $—SR^{b2}$, halo, $—OCF_3$, $—CN$, hydroxyl, $C_{2-6}$ alkenyl optionally and independently substituted with 0-2 occurrences of $R^{b2}$, $C_{2-6}$ alkynyl optionally and independently substituted with 0-2 occurrences of $R^{b2}$, $C_{1-6}$ alkyl optionally and independently substituted with 0-5 occurrences of $R^{15}$, $C_{1-6}$ alkoxy optionally and independently substituted with 0-3 occurrences of $R^{15}$, phenyl optionally and independently substituted with 0-3 occurrences of $R^{15}$, 5- or 6-membered heteroaryl optionally and independently substituted with 0-3 occurrences of $R^{15}$, $C_{3-8}$ cycloalkyl optionally and independently substituted with 0-3 occurrences of $R^{15}$ or 3-8 membered heterocyclyl optionally and independently substituted with 0-3 occurrences of $R^{15}$.

[28]. A compound of any one of [1] to [27] above, or according to other embodiments of the invention, wherein $R^{11}$ is H or $C_{1-6}$ alkyl optionally and independently substituted with 0-5 occurrences of $R^{15}$.

[29]. A compound of any one of [1] to [28] above, or according to other embodiments of the invention, wherein $R^{11}$ is $C_{1-6}$ alkyl optionally and independently substituted with 0-5 occurrences of $R^{15}$.

[30]. A compound of any one of [1] to [29] above, or according to other embodiments of the invention, wherein $R^{11}$ is methyl optionally and independently substituted with 0-3 occurrences of $R^{15}$.

[31]. A compound of any one of [1] to [30] above, or according to other embodiments of the invention, wherein $R^{15}$ is halo in each instance.

[32]. A compound of any one of [1] to [31] above, or according to other embodiments of the invention, wherein $R^{15}$ is fluoro in each instance.

[33]. A compound of any one of [1] to [30] above, or according to other embodiments of the invention, wherein $R^{11}$ is unsubstituted methyl.

[34]. A compound of any one of [1] to [32] above, or according to other embodiments of the invention, wherein $R^{11}$ is methyl substituted with 2 occurrences of $R^{15}$.

[35]. A compound of any one of [1] to [32], or [34] above, or according to other embodiments of the invention, wherein $R^{11}$ is $—CF_2H$.

[36]. A compound of any one of [1] to [32] above, or according to other embodiments of the invention, wherein $R^{11}$ is methyl independently substituted with 3 occurrences of $R^{15}$.

[37]. A compound of any one of [1] to [32], or [36] above, or according to other embodiments of the invention, wherein $R^{11}$ is $—CF_3$.

[38]. A compound of any one of [1] to [29] above, or according to other embodiments of the invention, wherein $R^{11}$ is ethyl optionally and independently substituted with 0-5 occurrences of $R^{15}$.

[39]. A compound of any one of [1] to [38] above, or according to other embodiments of the invention, wherein q is 0.

[40]. A compound of any one of [1] to [39] above, or according to other embodiments of the invention, wherein the core formed by rings E and A is selected from:

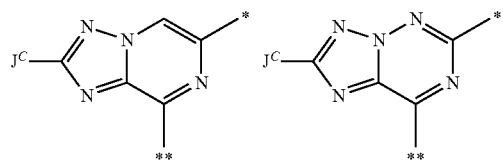
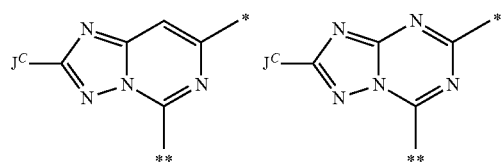
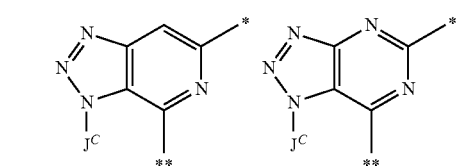
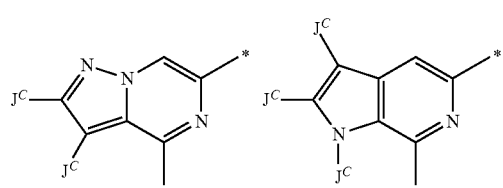
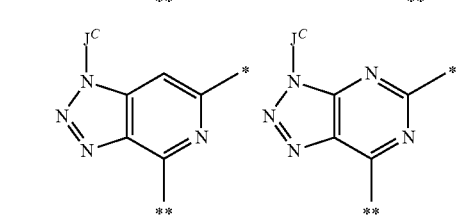
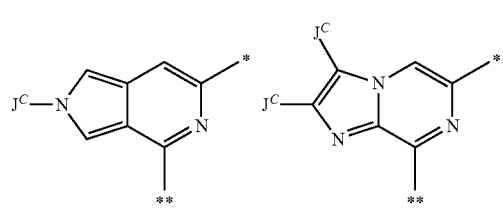
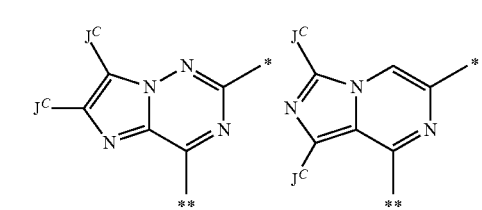

-continued

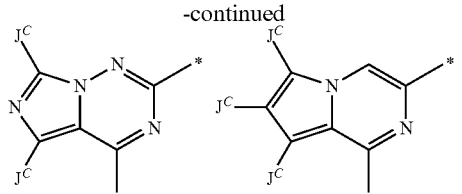
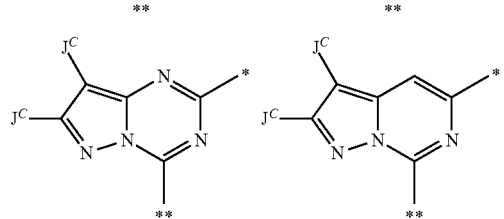
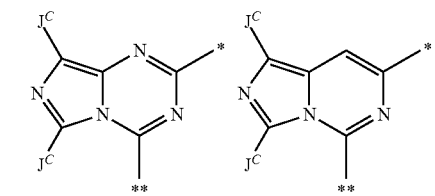
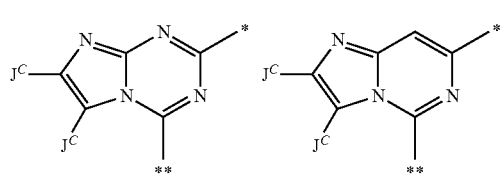
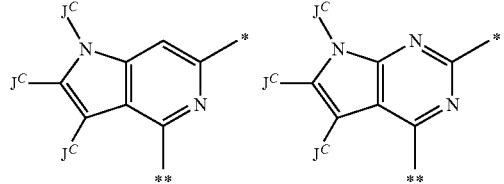
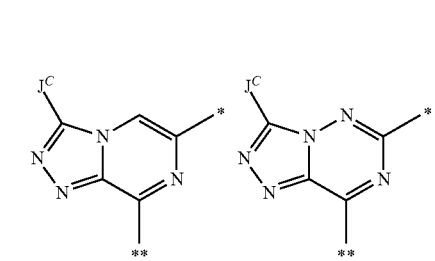
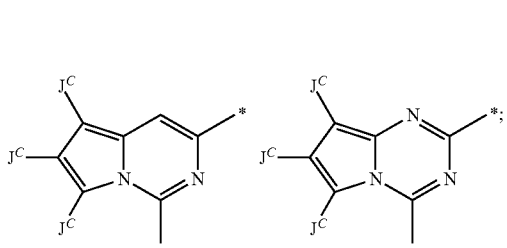

wherein the C atom with a symbol * represents the attachment point to the ring containing G, Z, and Q; and the C atom with a symbol ** represents the point of attachment of the 2 instances of J.

[41]. A compound of any one of [1] to [40] above, or according to other embodiments of the invention, wherein the core formed by rings E and A is selected from:

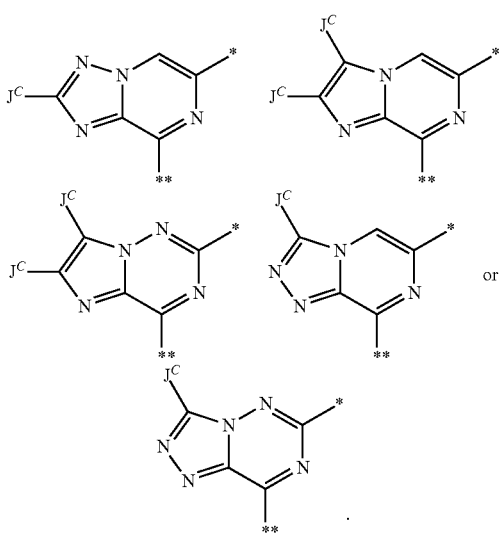

[42]. A compound of any one of [1] to [41] above, or according to other embodiments of the invention, wherein each instance of $J^C$ is hydrogen.

[43]. A compound of any one of [1] to [42] above, or according to other embodiments of the invention, wherein the compound is selected from those listed in Table I.

[44]. A pharmaceutical composition comprising at least one pharmaceutically acceptable excipient or carrier and a compound of any one of [1] to [42] above, or according to other embodiments of the invention.

[45]. A method for treating a disease, health condition or disorder selected from a CNS disease, health condition or disorder, the method comprising administering to a subject in need of treatment a therapeutically effective amount of a compound of any of [1] to [43] above, or a pharmaceutical composition of [44] above, or according to other embodiments of the invention, wherein the disease, health condition or disorder is selected from:

Alzheimer's disease, amyotrophic lateral sclerosis (ALS or Lou Gehrig's disease), Down syndrome, dementia, vascular dementia, mixed dementia, vascular cognitive impairment, Binswanger's dementia (subcortical arteriosclerotic encephalopathy), Cerebral Autosomal-Dominant Arteriopathy with Subcortical Infarcts and Leukoencephalopathy (CADASIL or CADASIL syndrome), frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia (mild cognitive impairment, MCI), glaucoma, Huntington's diseases (or chorea, HD), or a cognitive defect associated with HD; multiple sclerosis (MS), multiple system atrophy (MSA), Parkinson's disease, Parkinsonism Plus, spinocerebellar ataxias, Steel-Richardson-Olszewski disease (progressive supranuclear palsy), attention deficit disorder (ADD) and attention deficit hyperactivity disorder (ADHD);

neuropathic pain;

a psychiatric, mental, mood or affective disorder selected from a bipolar disorder, schizophrenia, general psychosis, drug-induced psychosis, a delusional disorder, schizoaffective disorder, obsessive compulsive disorder (OCD), a depressive disorder, an anxiety disorder, a panic disorder, or post-traumatic stress disorder (PTSD);

traumatic (closed or open, penetrating head injuries, including concussion and CTE) or non-traumatic (stroke (in particular, ischemic stroke), aneurism, hypoxia) injury to the brain or cognitive impairment or dysfunction resulting from brain injuries or neurodegenerative disorders;

dystonias, including generalized, focal, segmental, sexual, intermediate, acute dystonic reaction, and genetic/primary dystonia; and dyskinesias, including acute, chronic/tardive, and non-motor and levo-dopa induced dyskinesia (LID);

disorders characterized by a relative reduction in synaptic plasticity and synaptic processes including, Fragile X, Rhett's disorder, Williams syndrome, Renpenning's syndrome, autism spectrum disorders, including autism, Asperger's syndrome, pervasive development disorder and childhood disintegrative disorder;

chemo brain, levo-dopa induced addictive behavior, alcoholism, narcotic dependence (including to amphetamine, opiates or other substances) and substance abuse.

[46]. A method according to [45] above, or according to other embodiments of the invention, wherein the disease, health condition or disorder is selected from Alzheimer's disease, amyotrophic lateral sclerosis (ALS or Lou Gehrig's disease), Down syndrome, dementia, vascular dementia, mixed dementia, vascular cognitive impairment, Binswanger's dementia (subcortical arteriosclerotic encephalopathy), Cerebral Autosomal-Dominant Arteriopathy with Subcortical Infarcts and Leukoencephalopathy (CADASIL or CADASIL syndrome), frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia (mild cognitive impairment, MCI), glaucoma, Huntington's diseases (or chorea, HD), or a cognitive defect associated with HD; multiple sclerosis (MS), multiple system atrophy (MSA), Parkinson's disease, Parkinsonism Plus, spinocerebellar ataxias, Steel-Richardson-Olszewski disease (progressive supranuclear palsy), attention deficit disorder (ADD) or attention deficit hyperactivity disorder (ADHD).

[47]. A method according to [45] above, or according to other embodiments of the invention, wherein the disease, health condition or disorder is neuropathic pain.

[48]. A method according to [45] above, or according to other embodiments of the invention, wherein the disease, health condition or disorder is selected from a psychiatric, mental, mood or affective disorder selected from a bipolar disorder, schizophrenia, general psychosis, drug-induced psychosis, a delusional disorder, schizoaffective disorder, obsessive compulsive disorder (OCD), a depressive disorder, an anxiety disorder, a panic disorder, or post-traumatic stress disorder (PTSD).

[49]. A method according to [45] above, or according to other embodiments of the invention, wherein the disease, health condition or disorder is selected from traumatic or non-traumatic injury to the brain or cognitive impairment or dysfunction resulting from brain injuries or neurodegenerative disorders.

[50]. A method according to [45] above, or according to other embodiments of the invention, wherein the disease, health condition or disorder is selected from Alzheimer's disease or pre-Alzheimer's disease, mild to moderate Alzheimer's disease or moderate to severe Alzheimer's disease.

[51]. A method according to [45] above, or according to other embodiments of the invention, wherein the disease, health condition or disorder is selected from a dystonia or a dyskinesia.

[52]. A method according to [45] above, or according to other embodiments of the invention, wherein the disease, health condition or disorder is selected from a disorder characterized by a relative reduction in synaptic plasticity and synaptic processes, including Fragile X, Rhett's disorder, Williams syndrome, Renpenning's syndrome, autism spectrum disorders, including autism, Asperger's syndrome, pervasive development disorder and childhood disintegrative disorder.

[53]. A method according to [45] above, or according to other embodiments of the invention, wherein the disease, health condition or disorder is selected from chemo brain, levo-dopa induced addictive behavior, alcoholism, narcotic dependence (including to amphetamine, opiates or other substances) and substance abuse.

[54]. A method for treating a disease, health condition or disorder the method comprising administering to a subject in need of treatment a therapeutically effective amount of a compound of any of [1] to [43] above, or a pharmaceutical composition of [44] above, or according to other embodiments of the invention, wherein the disease, health condition or disorder is selected from:

disorders related to high blood pressure and decreased coronary blood flow, increased acute and chronic coronary blood pressure, arterial hypertension, vascular disorder resulting from cardiac and renal complications, heart disease, stroke, cerebral ischemia, renal failure, resistant hypertension, diabetic hypertension, congestive heart failure, diastolic or systolic dysfunction, coronary insufficiency, arrhythmia, reduction of ventricular preload, cardiac hypertrophy, heart failure/cardiorenal syndrome, portal hypertension, endothelial dysfunction or injury;

thromboembolic disorder, ischemia, myocardial infarction, stroke, transient ischemic attack (TIA), obstructive thromboanginitis, stable or unstable angina pectoris, coronary spasms, variant angina, Prinzmetal's angina, prevention of restenosis after thrombolysis therapies, thrombogenic disorders;

a CNS disease, health condition or disorder selected from Alzheimer's disease, amyotrophic lateral sclerosis, Down syndrome, dementia, vascular dementia, mixed dementia, vascular cognitive impairment, Binswanger's dementia, Cerebral Autosomal-Dominant Arteriopathy with Subcortical Infarcts and Leukoencephalopathy, frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia, glaucoma, Huntington's diseases, or a cognitive defect associated with HD; multiple sclerosis, multiple system atrophy, Parkinson's disease, Parkinsonism Plus, spinocerebellar ataxies, Steel-Richardson-Olszewski disease, attention deficit disorder and attention deficit hyperactivity disorder, Alzheimer's disease or pre-Alzheimer's disease, mild to moderate Alzheimer's disease or moderate to severe Alzheimer's disease, traumatic (closed or open, penetrating head injuries) brain injury (TBI), nontraumatic (stroke, aneurism, hypoxia) injury to the brain, cognitive impairment or dysfunction resulting from brain injuries or neurodegenerative disorder, dystonia, dyskinesia, a disorder characterized by a relative reduction in synaptic plasticity and synaptic processes, Fragile X, Rhett's disorder, Williams syndrome, Renpenning's syndrome, autism spectrum disorders, including autism, Asperger's syndrome, pervasive development disorder, childhood disintegrative disorder, neuropathic pain, bipolar disorder, schizophrenia, general psychosis, drug-induced psychosis, a delusional disorder, schizoaffective disorder, obsessive compulsive disorder, a depressive disorder, an anxiety disorder, a panic disorder, post-traumatic stress disorder, chemo brain, levo-dopa induced addictive behavior, alcoholism, narcotic dependence or substance abuse;

peripheral arterial disease, peripheral occlusive arterial disease, peripheral vascular disease, hypertonia, Raynaud's syndrome or phenomenon, critical limb ischemia, vasculitis, peripheral embolism, intermittent claudication, vaso-occlusive crisis, Duchenne muscular dystrophy, Becker muscular dystrophy, microcirculation abnormalities, control of vascular leakage or permeability;

shock, sepsis, cardiogenic shock, control of leukocyte activation, inhibition or modulation of platelet aggregation;

pulmonary hypertension, pulmonary arterial hypertension, associated pulmonary vascular remodeling, localized thrombosis, right heart hypertrophy, pulmonary hypertonia, primary pulmonary hypertension, secondary pulmonary hypertension, familial pulmonary hypertension, sporadic pulmonary hypertension, precapillary pulmonary hypertension, idiopathic pulmonary hypertension, thrombotic pulmonary arteriopathy, plexogenic pulmonary arteriopathy, cystic fibrosis, bronchoconstriction or pulmonary bronchoconstriction, acute respiratory distress syndrome, lung fibrosis, lung transplant;

pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary venooclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, other coagulation disorders, chronic thromboembolism, pulmonary embolism (due to tumor, parasites or foreign material), connective tissue disease, lupus, schistosomiasis, sarcoidosis, chronic obstructive pulmonary disease, asthma, emphysema, chronic bronchitis, pulmonary capillary hemangiomatosis, histiocytosis X, lymphangiomatosis and compressed pulmonary vessels (such as due to adenopathy, tumor or fibrosing mediastinitis);

atherosclerosis (e.g., associated with endothelial injury, platelet and monocyte adhesion and aggregation, smooth muscle proliferation and migration), restenosis (e.g., developed after thrombolysis therapies, percutaneous transluminal angioplasties (PTAs), percutaneous transluminal coronary angioplasties (PTCAs) and bypass), inflammation;

cardiovascular disease associated with metabolic syndrome (e.g., obesity, dyslipidemia, diabetes, high blood pressure), dyslipidemia, hypercholesterolemia, hypertriglyceridemia, sitosterolemia, fatty liver disease, hepatitis, preeclampsia, polycystic kidney disease progression, subcutaneous fat, obesity;

liver cirrhosis associated with chronic liver disease, hepatic fibrosis, hepatic stellate cell activation, hepatic fibrous collagen and total collagen accumulation; liver disease of necro-inflammatory and/or of immunological origin; renal fibrosis and renal failure resulting from chronic kidney diseases or insufficiency (e.g. due to accumulation/deposition and tissue injury, progressive sclerosis, glomerulonephritis); prostate hypertrophy systemic sclerosis; cardiac interstitial fibrosis; cardiac remodeling and fibrosis; cardiac hypertrophy; non-alcoholic steatohepatitis or NASH;

ischemia, reperfusion damage; ischemia/reperfusion associated with organ transplant, lung transplant, pulmonary transplant, cardiac transplant; conserving blood substituents in trauma patients;

erectile dysfunction; impotence; premature ejaculation; female sexual dysfunction, vaginal atrophy, dyspaneuria, atrophic vaginitis; benign prostatic hyperplasia (BPH) or hypertrophy or enlargement; bladder outlet obstruction; bladder pain syndrome (BPS), interstitial cystitis (IC), overactive bladder, neurogenic bladder and incontinence; diabetic nephropathy;

glaucoma, retinopathy, diabetic retinopathy (including proliferative and non-proliferative), blepharitis, dry eye syndrome, Sjögren's Syndrome;

hearing impairment, partial or total hearing loss; partial or total deafness; tinnitus; noise-induced hearing loss;

dermal fibrosis, scleroderma, skin fibrosis;

microvascular perfusion improvement (e.g., following injury, to counteract the inflammatory response in perioperative care), anal fissures, diabetic ulcers; and cancer metastasis, osteoporosis, gastroparesis; functional dyspepsia; diabetic complications, diseases associated with endothelial dysfunction, neurologic disorders associated with decreased nitric oxide production, achalasia or esophageal achalasia.

[55]. A method of treating or preventing a disease, health condition or disorder in a subject in need thereof, comprising administering, alone or in combination therapy, a therapeutically effective amount of a compound of any of [1] to [43] above, or a pharmaceutical composition of [44] above, or according to other embodiments of the invention, wherein the disease or disorder is one that benefits from sGC stimulation or from an increase in the concentration of NO or cGMP or both, or the upregulation of the NO pathway.

[56]. A method of any of [45] to [55] above, or according to other embodiments of the invention, further comprising a second amount of an additional suitable therapeutic agent.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

The invention claimed is:

1. A compound of Formula I-1, or a pharmaceutically acceptable salt thereof,

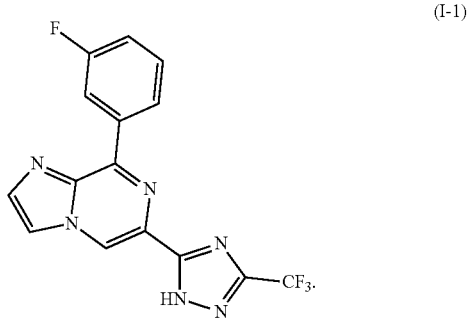 [SMILES: Fc1cccc(-c2nc(-c3nc(C(F)(F)F)n[nH]3)cn3ccnc23)c1]

(I-1)

2. A pharmaceutical composition comprising a compound according to claim 1, or a pharmaceutically acceptable salt thereof, and at least one pharmaceutically acceptable excipient or carrier.

* * * * *

UNITED STATES PATENT AND TRADEMARK OFFICE
CERTIFICATE OF CORRECTION

PATENT NO. : 10,472,363 B2
APPLICATION NO. : 15/693758
DATED : November 12, 2019
INVENTOR(S) : Glen Robert Rennie et al.

Page 1 of 1

It is certified that error appears in the above-identified patent and that said Letters Patent is hereby corrected as shown below:

In the Claims

At Column 154, Claim number 1, Line number 25-39, delete the following formula:

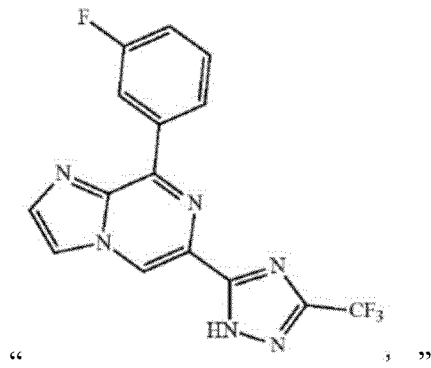

" , "

And replace with the formula as shown below:

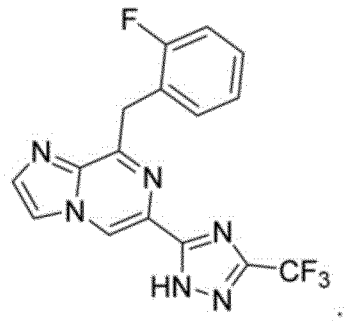

Signed and Sealed this
Fourth Day of February, 2020

Andrei Iancu
*Director of the United States Patent and Trademark Office*